(12) United States Patent
Bonnet et al.

(10) Patent No.: US 10,343,963 B2
(45) Date of Patent: Jul. 9, 2019

(54) COMPOSITION COMPRISING HF AND E-3,3,3-TRIFLUORO-1-CHLOROPROPENE

(71) Applicant: Arkema France, Colombes (FR)

(72) Inventors: Philippe Bonnet, Lyons (FR); Bertrand Collier, Saint-Genis-Laval (FR); Dominque Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/102,320

(22) Filed: Aug. 13, 2018

(65) Prior Publication Data

US 2018/0354875 A1 Dec. 13, 2018

Related U.S. Application Data

(63) Continuation of application No. 14/774,161, filed as application No. PCT/FR2014/050364 on Feb. 21, 2014, now Pat. No. 10,077,221.

(30) Foreign Application Priority Data

Mar. 20, 2013 (FR) .................................... 13 52483

(51) Int. Cl.
*C07C 21/18* (2006.01)
*C01B 7/19* (2006.01)
*C09K 3/30* (2006.01)
*C09K 5/04* (2006.01)

(52) U.S. Cl.
CPC .............. *C07C 21/18* (2013.01); *C01B 7/191* (2013.01); *C09K 3/30* (2013.01); *C09K 5/044* (2013.01)

(58) Field of Classification Search
None
See application file for complete search history.

(56) References Cited

U.S. PATENT DOCUMENTS

| | | | | |
|---|---|---|---|---|
| 6,013,846 A * | 1/2000 | Wismer | .................. | C07C 17/00 570/164 |
| 6,646,020 B2 | 11/2003 | Nyberg et al. | | |
| 6,814,884 B2 | 11/2004 | Jannick et al. | | |
| 7,438,826 B1 | 10/2008 | Chen et al. | | |
| 7,442,321 B1 | 10/2008 | Chen et al. | | |
| 8,323,524 B2 | 12/2012 | Flynn et al. | | |
| 8,450,537 B2 * | 5/2013 | Rao | .................. | C07C 17/10 570/156 |
| 8,541,478 B2 | 9/2013 | Singh et al. | | |
| 8,754,272 B2 | 6/2014 | Zhai et al. | | |
| 9,255,045 B2 | 2/2016 | Pigamo et al. | | |
| 9,834,499 B2 | 12/2017 | Pigamo et al. | | |
| 10,077,221 B2 * | 9/2018 | Bonnet | .................. | C07C 21/18 |
| 2004/0180978 A1 | 9/2004 | Dreier | | |
| 2005/0156135 A1 | 7/2005 | Minor et al. | | |
| 2005/0285079 A1 | 12/2005 | Minor | | |
| 2006/0106263 A1 | 5/2006 | Miller et al. | | |
| 2006/0142173 A1 | 6/2006 | Johnson et al. | | |
| 2006/0266976 A1 | 11/2006 | Minor et al. | | |
| 2007/0100173 A1 * | 5/2007 | Miller | .................. | C01B 7/191 570/178 |
| 2007/0100175 A1 * | 5/2007 | Miller | .................. | C01B 7/196 570/178 |
| 2007/0145325 A1 | 6/2007 | Minor | | |
| 2008/0051612 A1 * | 2/2008 | Knapp | .................. | C07C 17/25 570/178 |
| 2008/0098755 A1 | 5/2008 | Singh et al. | | |
| 2008/0125505 A1 | 5/2008 | Bowman et al. | | |
| 2009/0095014 A1 | 4/2009 | Sun et al. | | |
| 2009/0099274 A1 | 4/2009 | Van Der Puy et al. | | |
| 2009/0127496 A1 * | 5/2009 | Rao | .................. | B01J 27/125 252/67 |
| 2009/0253820 A1 | 10/2009 | Bowman et al. | | |
| 2009/0305876 A1 | 12/2009 | Singh et al. | | |
| 2009/0318323 A1 | 12/2009 | Johnson et al. | | |
| 2010/0004155 A1 | 1/2010 | Ishihara et al. | | |

(Continued)

FOREIGN PATENT DOCUMENTS

EP  0 940 382 A1  9/1999
JP  S62-225860 A  10/1987

(Continued)

OTHER PUBLICATIONS

U.S. Appl. No. 14/615,900, Wissam Rached, filed Feb. 6, 2015.
U.S. Appl. No. 16/027,743, Laurent Abbas and Wissam Rached, filed Jul. 5, 2018.
U.S. Appl. No. 15/809,477, Anne Pigamo, John Wismer, Bertrand Collier and Philippe Bonnet, filed Nov. 10, 2017.
U.S. Appl. No. 15/575,980, Anne Pigamo and Bertrand Collier, filed Nov. 21, 2017.
U.S. Appl. No. 16/027,743, Abbas, et al.
International Search Report issued in PCT/FR2014/050364, dated Jun. 6, 2014, 5 pages, European Patent Office, Rijswijk, NL (English and French versions).
Forane Blowing Agents by Arkema, Technical Profile Forane® 1233zd, copyright 2013, Arkema, King of Prussia, PA, www.forane.com, retrieved Jun. 2017, 6 pages.

(Continued)

*Primary Examiner* — Joseph D Anthony
(74) *Attorney, Agent, or Firm* — Buchanan Ingersoll & Rooney P.C.

(57) ABSTRACT

An azeotropic or quasi-azeotropic composition including hydrogen fluoride, E-3,3,3-trifluoro-1-chloropropene and optionally one or more (hydro)halogen-carbon compounds including between 1 and 3 carbon atoms. Also, a preferred azeotropic or quasi-azeotropic composition including hydrogen fluoride, E-3,3,3-trifluoro-1-chloropropene, and optionally one or more compounds selected from among 1,1,1,2,2-pentafluoropropane, 2,3,3,3-tetrafluoropropene, 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropane, 1,1,1,3,3-pentafluoropropene, 1,1,1,2,3-pentafluoropropene and 2-chloro,1,1,1,2-tetrafluoropropane.

10 Claims, No Drawings

(56) References Cited

U.S. PATENT DOCUMENTS

| | | | |
|---|---|---|---|
| 2010/0072415 A1* | 3/2010 | Rao | B01J 23/26 252/67 |
| 2010/0102273 A1 | 4/2010 | Basu et al. | |
| 2010/0105788 A1 | 4/2010 | Chen et al. | |
| 2010/0113629 A1 | 5/2010 | Van Horn et al. | |
| 2010/0187088 A1* | 7/2010 | Merkel | B01D 3/36 203/50 |
| 2010/0237279 A1* | 9/2010 | Hulse | C07C 17/206 252/182.12 |
| 2011/0041529 A1 | 2/2011 | Chen et al. | |
| 2011/0112340 A1* | 5/2011 | Smith | C07C 17/04 570/169 |
| 2011/0197602 A1 | 8/2011 | Abbas et al. | |
| 2011/0218369 A1* | 9/2011 | Elsheikh | C07C 17/206 570/151 |
| 2011/0309287 A1 | 12/2011 | Chen et al. | |
| 2011/0309288 A1 | 12/2011 | Chen et al. | |
| 2011/0315915 A1 | 12/2011 | Abbas et al. | |
| 2012/0041239 A1* | 2/2012 | Suzuki | C07C 17/206 570/160 |
| 2012/0053369 A1* | 3/2012 | Hulse | C07C 17/206 570/135 |
| 2012/0053372 A1 | 3/2012 | Hulse et al. | |
| 2012/0056122 A1* | 3/2012 | Hulse | C01B 7/191 252/67 |
| 2012/0138841 A1* | 6/2012 | Hulse | A62D 1/0057 252/2 |
| 2012/0138847 A1 | 6/2012 | Van Horn et al. | |
| 2012/0145955 A1 | 6/2012 | Abbas et al. | |
| 2012/0222448 A1* | 9/2012 | Chaki | C07C 17/383 62/617 |
| 2012/0329893 A1 | 12/2012 | Abbas | |
| 2013/0037058 A1 | 2/2013 | Abbas | |
| 2013/0105296 A1* | 5/2013 | Chaki | C01B 7/196 203/60 |
| 2013/0231399 A9 | 9/2013 | Basu et al. | |
| 2014/0012052 A1* | 1/2014 | Pham | C07C 17/38 570/160 |
| 2015/0152235 A1 | 6/2015 | Abbas | |
| 2015/0197467 A1 | 7/2015 | Pigamo et al. | |
| 2016/0009555 A1* | 1/2016 | Bonnet | C07C 21/18 252/182.12 |
| 2016/0023176 A1* | 1/2016 | Bonnet | C01B 7/191 51/307 |
| 2016/0023974 A1* | 1/2016 | Bonnet | C07C 21/18 252/182.12 |
| 2016/0031773 A1* | 2/2016 | Bonnet | C01B 7/195 252/182.12 |
| 2016/0046548 A1* | 2/2016 | Bonnet | C01B 7/19 252/182.12 |
| 2016/0115104 A1 | 4/2016 | Pigamo et al. | |
| 2018/0093934 A1 | 4/2018 | Pigamo et al. | |
| 2018/0148394 A1 | 5/2018 | Pigamo et al. | |
| 2018/0194703 A1* | 7/2018 | Chiu | B01D 3/009 |
| 2019/0048241 A1 | 2/2019 | Abbas et al. | |

FOREIGN PATENT DOCUMENTS

| | | |
|---|---|---|
| JP | H03-168566 A | 7/1991 |
| JP | H04-110388 A | 4/1992 |
| JP | H06-272978 A | 9/1994 |
| JP | H 07-6707 B2 | 1/1995 |
| JP | 2002-501035 A | 1/2002 |
| JP | 2008-133438 A | 6/2008 |
| JP | 2008-524433 A | 7/2008 |
| JP | 2011-037912 A | 2/2011 |
| JP | 2011-510119 A | 3/2011 |
| JP | 2012-506944 A | 3/2012 |
| WO | WO 99/37598 A1 | 7/1999 |
| WO | WO 02/40613 A1 | 5/2002 |
| WO | WO 2004/037913 A2 | 5/2004 |
| WO | WO 2004/037913 A3 | 5/2004 |
| WO | WO 2006/069362 A2 | 6/2006 |
| WO | WO 2006/069362 A3 | 6/2006 |
| WO | WO 2007/002625 A2 | 1/2007 |
| WO | WO 2007/002625 A3 | 1/2007 |
| WO | WO 2007/053736 A2 | 5/2007 |
| WO | WO 2008/002500 A1 | 1/2008 |
| WO | WO 2009/089511 A2 | 7/2009 |
| WO | WO 2009/089511 A3 | 7/2009 |
| WO | WO 2009/140231 A2 | 11/2009 |
| WO | WO 2010/043807 A1 | 4/2010 |
| WO | WO 2010/059493 A1 | 5/2010 |
| WO | WO 2010/062572 A2 | 6/2010 |
| WO | WO 2010/062572 A3 | 6/2010 |
| WO | WO 2010/085397 A1 | 7/2010 |
| WO | WO 2010/088196 A2 | 8/2010 |
| WO | WO 2010/088196 A3 | 8/2010 |
| WO | WO 2012/075283 A2 | 6/2012 |
| WO | WO 2014/147310 A1 | 9/2014 |
| WO | WO 2014/147311 A1 | 9/2014 |
| WO | WO 2014/147312 A1 | 9/2014 |
| WO | WO 2014/147313 A1 | 9/2014 |
| WO | WO 2014/147314 A1 | 9/2014 |

OTHER PUBLICATIONS

Official Action issued in JP 2011-531537, dated Jan. 20, 2016, 7 pages, Japan Patent Office, JP.

Official Action issued in JP 2015-026010, dated Mar. 1, 2016, 6 pages (3 pages JP OA; 3 pages Machine English-language translation), Japanese Patent Office, JP.

**Abbas, Laurent, et al., U.S. Appl. No. 16/027,743 entitled "Heat Transfer Method," filed in the U.S. Patent and Trademark Office on Jul. 5, 2018.

Rached, Wissam, U.S. Appl. No. 16/333,003 entitled "Composition Comprising 1-Chloro-3,3,3-Trifluoropropene," filed in the U.S. Patent and Trademark Office on Mar. 13, 2019.

\* cited by examiner

COMPOSITION COMPRISING HF AND E-3,3,3-TRIFLUORO-1-CHLOROPROPENE

CROSS REFERENCE TO RELATED APPLICATIONS

The present application is a continuation of U.S. application Ser. No. 14/774,161, filed on Sep. 10, 2015, which is a U.S. national stage of International Application No. PCT/FR2014/05034, filed on Feb. 21, 2014, which claims the benefit of French Application No. 13-52483, filed on Mar. 20, 2013. The entire contents of each of U.S. application Ser. No. 14/774,161, International Application No. PCT/FR2014/05034, and French Application No. 13-52483 are hereby incorporated herein by reference in their entirety.

TECHNICAL FIELD

The present invention relates to azeotropic or quasi-azeotropic compositions comprising E-3,3,3-trifluoro-1-chloropropene and hydrogen fluoride. These compositions may originate from intermediate compositions in the production of E-3,3,3-trifluoro-1-chloropropene and are generally useful in processes for recycling hydrogen fluoride.

BACKGROUND

The manufacture of E-3,3,3-trifluoro-1-chloropropene accompanied by a multitude of by-products, having a boiling point close to HCFO-1233zdE, leads to relatively complex and expensive purification steps. The difficulty encountered during the purification of HCFO-1233zdE generally implies an appreciable loss of desired product. Furthermore, these by-products may form azeotropic compositions with E-3,3,3-trifluoro-1-chloropropene, making separation by distillation simple, very difficult, or even impossible.

Fluids based on E-3,3,3-trifluoro-1-chloropropene have found numerous applications in varied industrial fields, especially as heat-transfer fluid, propellants, foaming agents, swelling agents, gaseous dielectrics, polymerization medium or monomer, support fluids, abrasive agents, drying agents and fluids for power production units.

Particular importance is given to fluids that have a low impact on the environment.

DETAILED DESCRIPTION

Following various experiments and trials, the Applicant has discovered that the compound E-3,3,3-trifluoro-1-chloropropene formed a heteroazeotropic or quasi-heteroazeotropic compound with hydrogen fluoride. It is difficult to identify novel fluids corresponding to these characteristics since azeotropes are not predictable.

The subject of the present invention is an azeotropic or quasi-azeotropic composition comprising hydrogen fluoride, E-3,3,3-trifluoro-1-chloropropene and optionally one or more (hydro)halocarbon compounds comprising between 1 and 3 carbon atoms.

According to one embodiment of the invention, the composition is heteroazeotropic or quasi-heteroazeotropic.

A heteroazeotropic or quasi-heteroazeotropic mixture is an azeotropic or quasi-azeotropic mixture in which the condensed liquid forms two immiscible solutions that can be readily separated, for example by decantation. This property is a considerable advantage for the recovery of HF.

The term "quasi-azeotropic" or "quasi-heteroazeotropic" has a broad meaning and is intended to include compositions that are strictly azeotropic or strictly heteroazeotropic and those that behave like an azeotropic or heteroazeotropic mixture.

A mixture is azeotropic when the pressure at the dew point is equal to that at the bubble formation point, which means that the vapor composition is equal to that of the condensed liquid.

A mixture is considered as quasi-azeotropic when the pressure at the dew point is substantially equal to that at the bubble formation point, which means that the vapor composition is substantially equal to that of the condensed liquid.

Another way of characterizing a mixture as quasi-azeotropic when the pressure difference between the pressure at the dew point and the pressure at the bubble formation point is low, preferentially less than or equal to 5%, on the basis of the pressure at the bubble formation point.

Compositions according to the invention especially concern the following compounds, the acronyms of which represent:

HF: hydrogen fluoride
HCC-40: chloromethane, or $CH_3Cl$
HCFC-115: chloropentafluoroethane, or $C_2F_5Cl$
HCFC-124: chlorotetrafluoroethane, or $C_2HF_4Cl$
HFC-125: pentafluoroethane, or $C_2HF_5$
HCFC-133a: 1-chloro-2,2,2-trifluoroethane, or $C_2H_2F_3Cl$
HFC-134a: 1,1,1,2-tetrafluoroethane, or $C_2H_2F_4$
HCFC-142b: 1-chloro-1,1-difluoroethane, or $C_2H_3F_2Cl$
HFC-143a: 1,1,1-trifluoroethane, or $C_2H_3F_3$
HFC-152a: 1,1-difluoroethane, or $C_2H_4F_2$
HFO-1132: 1,2-difluoroethylene, or $C_2H_2F_2$
HFO-1141: fluoroethylene, or $C_2H_3F$
HFO-1234yf: 2,3,3,3-tetrafluoropropene or $CH_2=CF-CF_3$
HFC-245cb: 1,1,1,2,2-pentafluoropropane or $CF_3-CF_2-CH_3$
HFO-1234zeE: E-1,3,3,3-tetrafluoropropene or $E-CF_3-CH=CHF$
HFO-1234zeZ: Z-1,3,3,3-tetrafluoropropene or $Z-CF_3-CH=CHF$
HFO-1243zf: 3,3,3-trifluoropropene or $CF_3-CH=CH_2$
HCFO-1233xf: 3,3,3-trifluoro-2-chloropropene or $CF_3-CCl=CH_2$
HCFO-1233zdE: E-3,3,3-trifluoro-1-chloropropene or $E-CF_3-CH=CHCl$
HCFO-1233zdZ: Z-3,3,3-trifluoro-1-chloropropene or $Z-CF_3-CH=CHCl$
HFO-1225yeZ: Z-1,1,1,2,3-pentafluoropropene or $Z-CHF=CF-CF_3$
HFO-1225yeE: E-1,1,1,2,3-pentafluoropropene or $E-CHF=CF-CF_3$
HFO-1225zc: 1,1,3,3,3-pentafluoropropene or $CF_2=CH-CF_3$
HFO-1225yc: 1,1,2,3,3-pentafluoropropene or $CF_2=CF-CF_2$
HCFC-1214: dichlorotetrafluoropropene, or $C_3F_4Cl_2$
HCFO-1215: chloropentafluoropropene, or $C_3F_5Cl$
HFO-1216: hexafluoropropene, or $C_3F_6$
HCFO-1223: dichlorotrifluoropropene, or $C_3HF_3Cl_2$
HCFO-1224: chlorotetrafluoropropene, or $C_3HF_4Cl$
HCFO-1232: dichlorodifluoropropene, or $C_3H_2F_2Cl_2$
HCFO-1233xc: 1,1,3-trifluoro-2-chloropropene or $CH_2F-CCl=CF_2$
HCFO-1233xe: 1,3,3-trifluoro-2-chloropropene or $CHF_2-CCl=CHF$
HCFO-1233yb: 1,2,3-trifluoro-1-chloropropene or $CH_2F-CF=CFCl$ HCFO-1233yc: 1,1,2-trifluoro-3-chloropropene or CH$_2$Cl—CF=CF$_2$
HCFO-1233yd: 2,3,3-trifluoro-1-chloropropene or CHF$_2$—CF=CHCl
HCFO-1233ye: 1,2,3-trifluoro-3-chloropropene or CHClF—CF=CHF
HCFO-1233yl: 2,3,3-trifluoro-3-chloropropene or CClF$_2$—CF=CH$_2$
HCFO-1233zb: 1,3,3-trifluoro-1-chloropropene or CHF$_2$—CH=CFCl
HCFO-1233zc: 1,1,3-trifluoro-3-chloropropene or CHClF—CH=CF$_2$
HCFO-1233ze: 1,3,3-trifluoro-3-chloropropene or CClF$_2$—CH=CHF
HFO-1234yc: 1,1,2,3-tetrafluoropropene or CF$_2$=CF—CH$_2$F
HFO-1234ye: 1,2,3,3-tetrafluoropropene or CHF=CF—CHF$_2$
HFO-1234zc: 1,1,3,3-tetrafluoropropene or CF$_2$=CH—CHF$_2$
HCFO-1242: chlorodifluoropropene, or C$_3$H$_3$F$_2$Cl
HFO-1243yc: 1,1,2-trifluoropropene or CH$_3$—CF=CF$_2$
HFO-1243ye: 1,2,3-trifluoropropene or CH$_2$F—CF=CHF
HFO-1243yl: 2,3,3-trifluoropropene or CHF$_2$—CF=CH$_2$
HFO-1243zc: 1,1,3-trifluoropropene or CH$_2$F—CH=CF$_2$
HFO-1243ze: 1,3,3-trifluoropropene or CHF$_2$—CH=CHF
HCFO-1251: chlorofluoropropene, or C$_3$H$_4$FCl
HFO-1252: difluoropropene, or C$_3$H$_4$F$_2$
HFO-216: hexafluoropropene, or C$_3$F$_6$Cl$_2$
HCFO-217: chloroheptafluoropropane, or C$_3$F$_7$Cl
HFC-218: octafluoropropane, or C$_3$F$_8$
HCFC-225: dichloropentafluoropropane, or C$_3$HF$_5$Cl$_2$
HCFC-226: chlorohexafluoropropane, or C$_3$HF$_6$Cl
HFC-227: heptafluoropropane, or C$_3$HF$_7$
HCFC-234: dichlorotetrafluoropropane, or C$_3$H$_2$F$_4$Cl$_2$
HCFC-235: chloropentafluoropropane, or C$_3$H$_2$F$_5$Cl
HFC-236: hexafluoropropane, or C$_3$H$_2$F$_6$
HCFC-243: dichlorotrifluoropropane, or C$_3$H$_3$F$_3$Cl$_2$
HCFC-244: chlorotetrafluoropropane, or C$_3$H$_3$F$_4$Cl
HCFC-244bb: 2-chloro,1,1,1,2-tetrafluoropropane or CF$_3$—CFCl—CH$_3$
HFC-245fa: 1,1,1,3,3-pentafluoropropane or CF$_3$—CH$_2$—CHF$_2$
HFC-245ea: 1,1,2,3,3-pentafluoropropane or CHF$_2$—CHF—CHF$_2$
HFC-245eb: 1,1,1,2,3-pentafluoropropane or CF$_3$—CHF—CH$_2$F
HFC-245ca: 1,1,2,2,3-pentafluoropropane or CHF$_2$—CF$_2$—CH$_2$F
HCFC-253: chlorotrifluoropropane, or C$_3$H$_4$F$_3$Cl
HFC-254: tetrafluoropropane, or C$_3$H$_4$F$_4$
HCFC-262: Chlorodifluoropropane, or C$_3$H$_5$F$_2$Cl
HFC-263: trifluoropropane, or C$_3$H$_5$F$_3$
Trifluoropropyne: CF$_3$—C≡CH The composition according to the invention may optionally be a mixture of one or more azeotropes and/or heteroazeotropes of ternary, quaternary, pentenary systems, systems with six compounds, systems with seven compounds, systems with eight or more compounds.

The compound(s) containing 1 and/or 2 carbon atoms may be chosen especially from chloromethane, chloropentafluoroethane, 1-chloro-1,2,2,2-tetrafluoroethane, 1-chloro-1,1,2,2-tetrafluoroethane, pentafluoroethane, 1-chloro-1,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene.

The compound(s) containing 3 carbon atoms may be chosen especially from 1,2-dichloro-1,1,2,3,3,3-hexafluoropropane, 1,3-dichloro-1,1,2,2,3,3-hexafluoropropane, 1,1-dichloro-1,2,2,3,3,3-hexafluoropropane, 2,2-dichloro-1,1,1,3,3,3-hexafluoropropane, 1-chloro-1,1,2,2,3,3,3-heptafluoropropane, 2-chloro-1,1,1,2,3,3,3-heptafluoropropane, octafluoropropane, dichloropentafluoropropane, 2,2-dichloro-1,1,1,3,3-pentafluoropropane, 2,3-dichloro-1,1,1,2,3-pentafluoropropane, 1,2-dichloro-1,1,2,3,3-pentafluoropropane, 3,3-dichloro-1,1,1,2,2-pentafluoropropane, 1,3-dichloro-1,1,2,2,3-pentafluoropropane, 1,1-dichloro-1,2,2,3,3-pentafluoropropane, 1,2-dichloro-1,1,3,3,3-pentafluoropropane, 1,3-dichloro-1,1,2,3,3-pentafluoropropane, 1,1-dichloro-1,2,3,3,3-pentafluoropropane, chlorohexafluoropropane, 2-chloro-1,1,1,2,3,3-hexafluoropropane, 3-chloro-1,1,1,2,2,3-hexafluoropropane, 1-chloro-1,1,2,2,3,3-hexafluoropropane, 2-chloro-1,1,1,3,3,3-hexafluoropropane, 1-chloro-1,1,2,3,3,3-hexafluoropropane, 1,1,2,2,3,3,3-heptafluoropropane, 1,1,1,2,3,3,3-Heptafluoropropane, dichlorotetrafluoropropane, 2,2-dichloro-1,1,3,3-tetrafluoropropane, 2,2-dichloro-1,1,1,3-tetrafluoropropane, 1,2-dichloro-1,2,3,3-tetrafluoropropane, 2,3-dichloro-1,1,1,2-tetrafluoropropane, 1,2-dichloro-1,1,2,3-tetrafluoropropane, 1,3-dichloro-1,2,2,3-tetrafluoropropane, 1,1-dichloro-2,2,3,3-tetrafluoropropane, 1,3-dichloro-1,1,2,2-tetrafluoropropane, 1,1-dichloro-1,2,2,3-tetrafluoropropane, 2,3-dichloro-1,1,1,3-tetrafluoropropane, 1,3-dichloro-1,1,3,3-tetrafluoropropane, 1,3-dichloro-1,1,3,3-tetrafluoropropane, 1,1-dichloro-1,3,3,3-tetrafluoropropane, 1,1-dichloro-2,3,3,3-tetrafluoropropane, 1,3-dichloro-1,1,2,3-tetrafluoropropane, 1,1-dichloro-1,2,3,3-tetrafluoropropane, chloropentafluoropropane, 1-chloro-1,2,2,3,3-pentafluoropropane, 3-chloro-1,1,1,2,3-pentafluoropropane, 1-chloro-1,1,2,2,3-pentafluoropropane, 2-chloro-1,1,3,3,3-pentafluoropropane, 1-chloro-1,1,3,3,3-pentafluoropropane, 1-chloro-1,1,2,3,3-pentafluoropropane, 3-chloro-1,1,1,2,2-pentafluoropropane, 2-chloro-1,1,2,3,3-pentafluoropropane, 2-chloro-1,1,1,2,3-pentafluoropropane, 1,1,1,2,2,3-hexafluoropropane, 1,1,1,2,3,3-hexafluoropropane, 1,1,1,3,3,3-hexafluoropropane, 1,1,2,2,3,3-hexafluoropropane, dichlorotrifluoropropane, 1,1-dichloro-3,3,3-trifluoropropane, 1,3-dichloro-1,1,3-trifluoropropane, 1,1-dichloro-1,3,3-trifluoropropane, 1,3-dichloro-1,2,3-trifluoropropane, 1,1-dichloro-2,3,3-trifluoropropane, 1,3-dichloro-1,1,2-trifluoropropane, 1,1-dichloro-1,2,3-trifluoropropane, 1,2-dichloro-1,3,3-trifluoropropane, 2,3-dichloro-1,1,1-trifluoropropane, 1,2-dichloro-1,1,3-trifluoropropane, 1,3-dichloro-1,2,2-trifluoropropane, 1,1-dichloro-2,2,3-trifluoropropane, 1,1-dichloro-1,2,2-trifluoropropane, 2,3-dichloro-1,1,2-trifluoropropane, 1,2-dichloro-1,2,3-trifluoropropane, 1,2-dichloro-1,1,2-trifluoropropane, 2,2-dichloro-1,1,3-trifluoropropane, 2,2-dichloro-3,3,3-trifluoropropane, chlorotetrafluoropropane, 2-chloro-1,2,3,3-tetrafluoropropane, 2-chloro-1,1,1,2-tetrafluoropropane, 3-chloro-1,1,2,2-tetrafluoropropane, 1-chloro-1,2,2,3-tetrafluoropropane, 1-chloro-1,1,2,2-tetrafluoropropane, 2-chloro-1,1,3,3-tetrafluoropropane, 2-chloro-1,1,1,3-tetrafluoropropane, 3-chloro-1,1,2,3-tetrafluoropropane, 3-chloro-1,1,2-tetrafluoropropane, 1-chloro-1,1,2,3-tetrafluoropropane, 3-chloro-1,1,1,3-tetrafluoropropane, 1-chloro-1,1,3,3-tetrafluoropropane, pentafluoropropane, 1,1,2,2,3-pentafluoropropane, 1,1,2,3,3-pentafluoropropane, 1,1,1,2,3-pentafluoropropane, 1,1,1,3,3-pentafluoropropane, chlorotrifluoropropane, 2-chloro-1,2,3-trifluoropropane, 2-chloro-1,1,2-trifluoropropane, 1-chloro-2,2,3-trifluoropropane, 1-chloro-1,2,2-trifluoropropane, 3-chloro-1,1,2-trifluoropropane, 1-chloro-1,2,3-trifluoropropane, 1-chloro-1,1,2-trifluoropropane, 3-chloro-1,3,3-trifluoropropane, 3-chloro-1,1,1-trifluoropropane, 1-chloro-1,1,3-trifluoropropane, 2-chloro-1,1,3-trifluoropropane, 2-chloro-1,1,1-trifluoropropane, 1,1,2,2-tetrafluoropropane, 1,1,1,3-tetrafluoropropane, 1,1,2,3-tetrafluoropropane, 1,1,1,2-tetrafluoropropane, 1,2,2,3-tetrafluoropropane, 1,1,3,3-tetrafluoropropane, chlorodifluoropropane, 1-chloro-2,2-difluoropropane, 3-chloro-1,1-difluoropropane, 1-chloro-1,3-difluoropropane, 1-chloro-1,1-difluoropropane, 1-chloro-2,3-difluoropropane, 1-chloro-1,2-difluoropropane, 2-chloro-1,3-difluoropropane, 2-chloro-1,1-difluoropropane, 2-chloro-1,2-difluoropropane, trifluoropropane, 1,1,1-trifluoropropane, 1,1,3-trifluoropropane, 1,2,3-trifluoropropane, 1,1,2-trifluoropropane, 1,2,2-trifluoropropane, dichlorotetrafluoropropene, 1,2-dichloro-1,3,3,3-tetrafluoropropene, 1,1-dichloro-2,3,3,3-tetrafluoropropene, 1,3-dichloro-1,2,3,3-tetrafluoropropene, 2,3-dichloro-1,1,3,3-tetrafluoropropene, 3,3-dichloro-1,1,2,3-tetrafluoropropene, chloropentafluoropropene, 1-chloropentafluoropropene, 2-chloropentafluoropropene, 3-chloropentafluoropropene, hexafluoropropene, dichlorotrifluoropropene, 1,1-dichloro-3,3,3-trifluoropropene, 1,2-dichloro-3,3,3-trifluoropropene, 2,3-dichloro-1,3,3-trifluoropropene, 1,3-dichloro-2,3,3-trifluoropropene, 1,2-dichloro-1,3,3-trifluoropropene, 2,3-dichloro-1,1,3-trifluoropropene, 1,1-dichloro-2,3,3-trifluoropropene, 1,3-dichloro-1,2,3-trifluoropropene, 3,3-dichloro-1,1,2-trifluoropropene, 3,3-dichloro-1,2,3-trifluoropropene, 1,3-dichloro-1,3,3-trifluoropropene, 3,3-dichloro-1,1,3-trifluoropropene, 1-chloro-2,3,3,3-tetrafluoropropene, 1-chloro-1,3,3,3-tetrafluoropropene, 2-chloro-1,3,3,3-tetrafluoropropene, 3-chloro-1,2,3,3-tetrafluoropropene, 3-chloro-1,1,3,3-tetrafluoropropene, 2-chloro-1,1,3,3-tetrafluoropropene, 1-chloro-1,2,3,3-tetrafluoropropene, 3-chloro-1,1,2,3-tetrafluoropropene, 1,2,3,3,3-pentafluoropropene, 1,1,3,3,3-pentafluoropropene, 1,1,2,3,3-pentafluoropropene, dichlorodifluoropropene, 2,3-dichloro-3,3-difluoropropene, 1,2-dichloro-1,3-difluoropropene, 2,3-dichloro-1,1-difluoropropene, 1,2-dichloro-3,3-difluoropropene, 2,3-dichloro-1,3-difluoropropene, 1,1-dichloro-2,3-difluoropropene, 1,3-dichloro-1,2-difluoropropene, 1,3-dichloro-2,3-difluoropropene, 3,3-dichloro-1,2-difluoropropene, 3,3-dichloro-2,3-difluoropropene, 1,1-dichloro-3,3-difluoropropene, 1,3-dichloro-1,3-difluoropropene, 3,3-dichloro-1,1-difluoropropene, 1,3-dichloro-3,3-difluoropropene, 3,3-dichloro-1,3-difluoropropene, chlorotrifluoropropene, 2-chloro-1,1,3-trifluoropropene, 2-chloro-1,3,3-trifluoropropene, 1-chloro-1,2,3-trifluoropropene, 3-chloro-1,1,2-trifluoropropene, 1-chloro-2,3,3-trifluoropropene, 3-chloro-1,2,3-trifluoropropene, 3-chloro-2,3,3-trifluoropropene, 1-chloro-1,3,3-trifluoropropene, 3-chloro-1,1,3-trifluoropropene, 3-chloro-1,3,3-trifluoropropene, 1,1,2,3-tetrafluoropropene, 2,3,3,3-tetrafluoropropene, 1,2,3,3-tetrafluoropropene, 1,1,3,3-tetrafluoropropene, chlorodifluoropropene, 3-chloro-3,3-difluoropropene, 3-chloro-1,3-difluoropropene, 2-chloro-1,1-difluoropropene, 2-chloro-1,3-difluoropropene, 2-chloro-3,3-difluoropropene, 1-chloro-1,2-difluoropropene, 1-chloro-2,3-difluoropropene, 3-chloro-1,2-difluoropropene, 3-chloro-2,3-difluoropropene, 1-chloro-1,3-difluoropropene, 3-chloro-1,1-difluoropropene, 1-chloro-3,3-difluoropropene, trifluoropropene, 1,1,2-trifluoropropene, 1,2,3-trifluoropropene, 2,3,3-trifluoropropene, 1,1,3-trifluoropropene, 1,3,3-trifluoropropene, chlorofluoropropene, 1-chloro-3-fluoropropene, 1-chloro-1-fluoropropene, 1-chloro-2-fluoropropene, 2-chloro-1-fluoropropene, 2-chloro-3-fluoropropene, 3-chloro-2-fluoropropene, 3-chloro-1-fluoropropene, 3-chloro-3-fluoropropene, difluoropropene, 1,2-difluoropropene, 2,3-difluoropropene, 1,1-difluoropropene, 1,3-difluoropropene, 3,3-difluoropropene, 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, Z-3,3,3-trifluoro-1-chloropropene and trifluoropropyne.

Preferably, the ternary compositions consisting essentially of HF-HFCO-1233zdE-HFC-245fa are excluded from the present invention.

A subject of the present invention is also an azeotropic or quasi-azeotropic composition comprising hydrogen fluoride, E-3,3,3-trifluoro-1-chloropropene, and optionally one or more compounds chosen from 1,1,1,2,2-pentafluoropropane, 2,3,3,3-tetrafluoropropene, 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

A subject of the present invention is also an azeotropic or quasi-azeotropic composition comprising hydrogen fluoride, E-3,3,3-trifluoro-1-chloropropene and optionally at least one or more organic compounds chosen from 1,1,1,2,2-pentafluoropropane, 2,3,3,3-tetrafluoropropene, E-1,3,3,3-tetrafluoropropene, Z-1,3,3,3-tetrafluoropropene, 3,3,3-trifluoropropene, 3,3,3-trifluoro-2-chloropropene.

According to one embodiment, the composition according to the invention comprises hydrogen fluoride, E-3,3,3-trifluoro-1-chloropropene, 1,1,1,2,2-pentafluoropropane and optionally one or more compounds chosen from 2,3,3,3-tetrafluoropropene, 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, 2,3,3,3-tetrafluoropropene and optionally one or more compounds chosen from 3,3,3-trifluoropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, E-3,3,3-trifluoro-1-chloropropene, 3,3,3-trifluoropropene and optionally one or more compounds chosen from 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, 3,3,3-trifluoro-2-chloropropene and optionally one or more compounds chosen from 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, E-3,3,3-trifluoro-1-chloropropene, 1,3,3,3-tetrafluoropropene and optionally one or more compounds chosen from trifluoropropyne, 1,1,1,3,3-pentafluoropropane, 1,1,1,3,3-pentafluoropropene, 1,1,1,2,3-pentafluoropropene and 2-chloro-1,1,1,2-tetrafluropropane.

According to another embodiment, the composition according to the invention comprises hydrogen fluoride, E-3,3,3-trifluoro-1-chloropropene, trifluoropropyne and optionally one or more compounds chosen from 1,1,1,3,3-pentafluoropropane, 1,1,1,3,3-pentafluoropropene, 1,1,1,2,3-pentafluoropropene and 2-chloro,1,1,1,2-tetrafluoropropane.

According to one embodiment, the composition according to the invention comprises hydrogen fluoride, E-3,3,3-trifluoro-1-chloropropene, 1,1,1,3,3-pentafluoropropane and optionally one or more compounds chosen from 1,1,1,3,3-pentafluoropropene, 1,1,1,2,3-pentafluoropropene and 2-chloro,1,1,1,2-tetrafluoropropane.

According to another embodiment, the composition according to the invention comprises hydrogen fluoride, E-3,3,3-trifluoro-1-chloropropene, 1,1,1,3,3-pentafluoropropene and optionally one or more compounds chosen from 1,1,1,2,3-pentafluoropropene and 2-chloro,1,1,1,2-tetrafluoropropane.

According to one embodiment, the composition according to the invention comprises hydrogen fluoride, E-3,3,3-trifluoro-1-chloropropene, 1,1,1,3,3-pentafluoropropene and optionally 2-chloro-1,1,1,2-tetrafluoropropane.

According to another embodiment, the composition according to the invention comprises hydrogen fluoride, E-3,3,3-trifluoro-1-chloropropene and 2-chloro-1,1,1,2-tetrafluoropropane.

According to one embodiment, the composition according to the invention comprises hydrogen fluoride, E-3,3,3-trifluoro-1-chloropropene, 1,1,1,2,2-pentafluoropropane and optionally one or more compounds chosen from 2,3,3,3-tetrafluoropropene, E-1,3,3,3-tetrafluoropropene, Z-1,3,3,3-tetrafluoropropene, 3,3,3-trifluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, E-3,3,3-trifluoro-1-chloropropene, 2,3,3,3-tetrafluoropropene and optionally one or more compounds chosen from E-1,3,3,3-tetrafluoropropene, Z-1,3,3,3-tetrafluoropropene, 3,3,3-trifluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane. According to one embodiment, the composition according to the invention comprises hydrogen fluoride, E-3,3,3-trifluoro-1-chloropropene, E-1,3,3,3-tetrafluoropropene and optionally one or more compounds chosen from Z-1,3,3,3-tetrafluoropropene, 3,3,3-trifluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, Z-1,3,3,3-tetrafluoropropene and optionally one or more compounds chosen from 3,3,3-trifluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, E-3,3,3-trifluoro-1-chloropropene, 3,3,3-trifluoropropene and optionally one or more compounds chosen from 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrachloropropane.

According to one embodiment according to the invention, the composition comprises hydrogen fluoride, E-3,3,3-trifluoro-1-chloropropene, 3,3,3-trifluoro-2-chloropropene and optionally one or more compounds chosen from trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

Irrespective of the embodiment, the composition preferably comprises from 1% to 85% and advantageously from 5% to 80% by weight of hydrogen fluoride and from 99% to 15% and advantageously from 20% to 95% by weight of the sum of the organic compounds; more particularly, the composition comprises from 1% to 85% by weight of hydrogen fluoride and from 99% to 15% by weight of the sum of the organic compounds (HFO-1233zdE and the (hydro)halocarbon compounds).

Irrespective of the embodiment, the boiling point of the composition according to the invention is between −20° C. and 80° C. and at a pressure between 0.1 and 44 bar absolute, preferentially between 0° C. and 40° C. and preferentially at a pressure of between 0.7 and 18 bar absolute, advantageously between 0.9 and 12.5 bar absolute.

The Applicant has discovered that the compositions according to the invention have advantageous properties in particular for the recycling of HF in the reaction step. Thus, the condensed phase of these compositions, optionally when they are subjected to a distillation step and/or a liquid/liquid separation step, such as by decantation, form two immiscible liquid phases.

By way of example, for the ternary compounds containing hydrogen fluoride, E-3,3,3-trifluoro-1-chloropropene and a compound chosen from 1,1,1,2,2-pentafluoropropane, 2,3,3,3-tetrafluoropropene, 3,3,3-trifluoropropene, 1,3,3,3-tetrafluoropropene, 3,3,3-trifluoro-2-chloropropene, the appearance of a heteroazeotrope characterized by two liquid phases, one rich in HF and the other depleted in HF, depends on the amount of HF in the composition. These decantation ranges as a function of the HF content in the compositions were characterized for at least isotherms at 0° C., 25° C. and 40° C.

Similarly, the decantation ranges for the ternary compounds containing hydrogen fluoride, E-3,3,3-trifluoro-1-chloropropene and a compound chosen from trifluoropropyne, 1,1,1,3,3-pentafluoropropane, 1,1,1,3,3-pentafluoropropene, Z-1,1,1,2,3-pentafluoropropene and 2-chloro-1,1,1,2-tetrafluoropropane are characterized by a phase depleted in HF and a phase enriched in HF for at least isotherms at 0° C., 25° C. and 40° C.

The Applicant has observed the same phenomenon for compositions of hydrogen fluoride, E-3,3,3-trifluoro-1-chloropropene comprising several compounds chosen from 1,1,1,2,2-pentafluoropropane, 2,3,3,3-tetrafluoropropene, 3,3,3-trifluoropropene, 1,3,3,3-tetrafluoropropene, 3,3,3-trifluoro-2-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

An azeotropic or quasi-azeotropic composition that is preferred according to the invention comprises from 5% to 70% by weight of hydrogen fluoride and from 95% to 30% by weight of HCFO-1233zdE, the boiling point of this preferred composition is between 0 and 40° C. at a pressure of between 0.9 and 4 bar absolute.

An azeotropic or quasi-azeotropic composition that is preferred according to the invention preferably comprises from 10% to 65% by weight of hydrogen fluoride and from 90% to 35% by weight of HCFO-1233zdE, the boiling point of this preferred composition is between 0 and 40° C. at a pressure of between 0.9 and 4 bar absolute.

An azeotropic or quasi-azeotropic composition that is preferred according to the invention comprises from 1% to 85% by weight of hydrogen fluoride and from 99% to 15% by weight of the sum of HCFO-1233zdE and of HFC-245cb, the boiling point of this preferred composition is between 0 and 40° C. at a pressure of between 0.9 and 10.5 bar absolute.

An azeotropic or quasi-azeotropic composition that is preferred according to the invention preferably comprises from 10% to 80% by weight of hydrogen fluoride and from 90% to 20% by weight of the sum of HCFO-1233zdE and of HFO-245b, the boiling point of this preferred composition is between 0 and 40° C. at a pressure of between 0.9 and 10.5 bar absolute.

An azeotropic or quasi-azeotropic composition that is preferred according to the invention comprises from 1% to 80% by weight of hydrogen fluoride and from 99% to 20% by weight of the sum of HCFO-1233zdE and of HFO-1243zf, the boiling point of this preferred composition is between 0 and 40° C. at a pressure of between 0.9 and 10.5 bar absolute.

An azeotropic or quasi-azeotropic composition that is preferred according to the invention preferably comprises from 5% to 75% by weight of hydrogen fluoride and from 95% to 25% by weight of the sum of HCFO-1233zdE and of HFO-1243zf, the boiling point of this preferred composition is between 0 and 40° C. at a pressure of between 0.9 and 10.5 bar absolute.

An azeotropic or quasi-azeotropic composition that is preferred according to the invention comprises from 1% to 85% by weight of hydrogen fluoride and from 99% to 15% by weight of the sum of HCFO-1233zdE, of HFC-245cb and of HFO-1243zf, the boiling point of this preferred composition is between 0 and 40° C. at a pressure of between 0.9 and 10.5 bar absolute.

An azeotropic or quasi-azeotropic composition that is preferred according to the invention preferably comprises from 5% to 80% by weight of hydrogen fluoride and from 95% to 20% by weight of the sum of HCFO-1233zdE, of HFC-245cb and of HFO-1243zf, the boiling point of this preferred composition is between 0 and 40° C. at a pressure of between 0.9 and 10.5 bar absolute.

An azeotropic or quasi-azeotropic composition that is preferred according to the invention comprises from 1% to 80% by weight of hydrogen fluoride and from 99% to 20% by weight of the sum of HCFO-1233zd, of HCFC-244bb, of HFC-245a, of trifluoropropyne, of HFO-1225yeZ and of HFO-1225zc, the boiling point of this preferred composition is between 0 and 40° C. at a pressure of between 0.7 and 18 bar absolute.

An azeotropic or quasi-azeotropic composition that is preferred according to the invention preferably comprises from 5% to 75% by weight of hydrogen fluoride and from 95% to 25% by weight of the sum of HCFO-1233zd, of HCFC-244bb, of HFC-245a, of trifluoropropyne, of HFO-1225yeZ and of HFO-1225zc, the boiling point of this preferred composition is between 0 and 40° C. at a pressure of between 0.7 and 18 bar absolute.

The pressure characteristics of the mixtures in Examples 1, 4, 7, 10, 13, 16, 19 and 22 have been calculated for an isotherm at 25° C.

Examples 2, 5, 8, 11, 14, 17, 20 and 23 represent the boiling points and pressure ranges of the mixtures and Examples 3, 6, 9, 12, 15, 18, 21 and 23 represent the decantation ranges of the mixtures of Examples 1, 4, 7, 10, 13, 16, 19 and 22 as a function of the mass percentage of HF characterized for isotherms at 0° C., 25° C. and 40° C. The decantation ranges of Examples 3, 6, 9, 12, 15, 18, 21 and 23 are calculated for mixtures of organic compounds having equal-mass contents. By way of example, for a ternary mixture, a mixture containing 50% by weight of each of the two organic compounds is considered; for a pentenary mixture, a mixture containing 25% by weight of each of the four organic compounds is considered, the mass fraction of HF ranging from 0 to 1. These calculations are performed at the liquid-vapor equilibrium, under azeotropic conditions.

Example 1: Binary Mixture

| | HF-HCFO-1233zdE | | |
|---|---|---|---|
| | Binary HF-F1233zdE | | |
| HF massfrac | Isotherm 0° C. Pressure bar | Isotherm 25° C. Pressure bar | Isotherm 40° C. Pressure bar |
| 0 | 0.5 | 1.3 | 2.2 |
| 0.05 | 0.9 | 2.4 | 4.0 |
| 0.1 | 0.9 | 2.4 | 4.0 |
| 0.15 | 0.9 | 2.4 | 4.0 |
| 0.2 | 0.9 | 2.4 | 4.0 |
| 0.25 | 0.9 | 2.4 | 4.0 |
| 0.3 | 0.9 | 2.4 | 4.0 |
| 0.35 | 0.9 | 2.4 | 4.0 |
| 0.4 | 0.9 | 2.4 | 4.0 |
| 0.45 | 0.9 | 2.4 | 4.0 |
| 0.5 | 0.9 | 2.4 | 4.0 |
| 0.55 | 0.9 | 2.4 | 4.0 |
| 0.6 | 0.9 | 2.4 | 4.0 |
| 0.65 | 0.9 | 2.4 | 4.0 |
| 0.7 | 0.9 | 2.4 | 4.0 |
| 0.75 | 0.9 | 2.4 | 3.9 |
| 0.8 | 0.9 | 2.3 | 3.8 |
| 0.85 | 0.9 | 2.2 | 3.5 |
| 0.9 | 0.8 | 1.9 | 3.2 |
| 0.95 | 0.6 | 1.6 | 2.7 |
| 1 | 0.5 | 1.2 | 1.9 |

Example 2: Temperature and Pressure Range of the Binary Mixture

| | Boiling point range | |
|---|---|---|
| Binary | Temperature ° C. | Pressure bar abs |
| HF-HCFO-1233zdE-HFC-245cb | 0 to 40 | ~0.9 to ~4.0 |

Example 3: Decantation Range of the Binary Mixture

| | Decantation ranges Mass percentage of HF Temperature | | |
|---|---|---|---|
| Binary system | 0° C. | 25° C. | 40° C. |
| HF-HCFO-1233zdE | 5-80% | 5-75% | 5-70% |

Example 4: Ternary Mixtures, Isotherm at 25° C.

| HF-HCFO-1233zdE-HFC-245cb | | | | | | HF-HCFO-1233xf-HCFO-1233zdE | | | | | |
|---|---|---|---|---|---|---|---|---|---|---|---|
| Organics 0.95 F1233zdE + 0.05 F245cb | | Organics 0.5 F1233zdE + 0.5 F245cb | | Organics 0.05 F1233zdE + 0.95 F245cb | | Organics 0.95 F1233zdE + 0.05 F1233xf | | Organics 0.5 F1233zdE + 0.5 F1233xf | | Organics 0.05 F1233zdE + 0.95 F1233xf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 3.0 | 0 | 4.5 | 0 | 1.3 | 0 | 1.4 | 0 | 1.5 |
| 0.05 | 2.6 | 0.05 | 4.2 | 0.05 | 5.7 | 0.05 | 2.4 | 0.05 | 2.5 | 0.05 | 2.6 |
| 0.1 | 2.6 | 0.1 | 4.2 | 0.1 | 5.7 | 0.1 | 2.4 | 0.1 | 2.5 | 0.1 | 2.6 |
| 0.15 | 2.6 | 0.15 | 4.2 | 0.15 | 5.7 | 0.15 | 2.4 | 0.15 | 2.5 | 0.15 | 2.6 |
| 0.2 | 2.6 | 0.2 | 4.2 | 0.2 | 5.7 | 0.2 | 2.4 | 0.2 | 2.5 | 0.2 | 2.6 |
| 0.25 | 2.6 | 0.25 | 4.2 | 0.25 | 5.7 | 0.25 | 2.4 | 0.25 | 2.5 | 0.25 | 2.6 |
| 0.3 | 2.6 | 0.3 | 4.2 | 0.3 | 5.7 | 0.3 | 2.4 | 0.3 | 2.5 | 0.3 | 2.6 |
| 0.35 | 2.6 | 0.35 | 4.2 | 0.35 | 5.7 | 0.35 | 2.4 | 0.35 | 2.5 | 0.35 | 2.6 |
| 0.4 | 2.6 | 0.4 | 4.2 | 0.4 | 5.7 | 0.4 | 2.4 | 0.4 | 2.5 | 0.4 | 2.6 |
| 0.45 | 2.6 | 0.45 | 4.2 | 0.45 | 5.7 | 0.45 | 2.4 | 0.45 | 2.5 | 0.45 | 2.6 |
| 0.5 | 2.6 | 0.5 | 4.2 | 0.5 | 5.7 | 0.5 | 2.4 | 0.5 | 2.5 | 0.5 | 2.6 |
| 0.55 | 2.6 | 0.55 | 4.2 | 0.55 | 5.7 | 0.55 | 2.4 | 0.55 | 2.5 | 0.55 | 2.6 |
| 0.6 | 2.6 | 0.6 | 4.3 | 0.6 | 5.7 | 0.6 | 2.4 | 0.6 | 2.5 | 0.6 | 2.6 |
| 0.65 | 2.6 | 0.65 | 4.3 | 0.65 | 5.7 | 0.65 | 2.4 | 0.65 | 2.5 | 0.65 | 2.6 |
| 0.7 | 2.6 | 0.7 | 4.3 | 0.7 | 5.7 | 0.7 | 2.4 | 0.7 | 2.5 | 0.7 | 2.6 |
| 0.75 | 2.6 | 0.75 | 4.4 | 0.75 | 5.7 | 0.75 | 2.4 | 0.75 | 2.5 | 0.75 | 2.6 |
| 0.8 | 2.5 | 0.8 | 4.4 | 0.8 | 5.7 | 0.8 | 2.3 | 0.8 | 2.4 | 0.8 | 2.5 |
| 0.85 | 2.4 | 0.85 | 4.1 | 0.85 | 5.7 | 0.85 | 2.2 | 0.85 | 2.3 | 0.85 | 2.3 |
| 0.9 | 2.1 | 0.9 | 3.5 | 0.9 | 4.9 | 0.9 | 1.9 | 0.9 | 2.0 | 0.9 | 2.1 |
| 0.95 | 1.7 | 0.95 | 2.6 | 0.95 | 3.5 | 0.95 | 1.6 | 0.95 | 1.7 | 0.95 | 1.7 |
| 1 | 1.2 | 1 | 1.2 | 1 | 1.2 | 1 | 1.2 | 1 | 1.2 | 1 | 1.2 |

| HF-HFO-1234zeE-HCFO-1233zdE | | | | | | HF-HFO-1234zeZ-HCFO-1233zdE | | | | | |
|---|---|---|---|---|---|---|---|---|---|---|---|
| Organics 0.95 F1233zdE + 0.05 F1234zeE | | Organics 0.5 F1233zdE + 0.5 F1234zeE | | Organics 0.05 F1233zdE + 0.95 F1234zeE | | Organics 0.95 F1233zdE + 0.05 F1234zeZ | | Organics 0.5 F1233zdE + 0.5 F1234zeZ | | Organics 0.05 F1233zdE + 0.95 F1234zeZ | |
| MASSFRAC HF | TOTAL PRES bar | MASSFRAC HF | TOTAL PRES bar | MASSFRAC HF | TOTAL PRES bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 3.2 | 0 | 4.7 | 0 | 1.3 | 0 | 1.6 | 0 | 1.8 |
| 0.05 | 2.6 | 0.05 | 4.2 | 0.05 | 5.7 | 0.05 | 2.4 | 0.05 | 2.7 | 0.05 | 2.9 |
| 0.1 | 2.6 | 0.1 | 4.2 | 0.1 | 5.7 | 0.1 | 2.4 | 0.1 | 2.7 | 0.1 | 2.9 |
| 0.15 | 2.6 | 0.15 | 4.2 | 0.15 | 5.7 | 0.15 | 2.4 | 0.15 | 2.7 | 0.15 | 2.9 |
| 0.2 | 2.6 | 0.2 | 4.2 | 0.2 | 5.7 | 0.2 | 2.4 | 0.2 | 2.7 | 0.2 | 2.9 |
| 0.25 | 2.6 | 0.25 | 4.2 | 0.25 | 5.7 | 0.25 | 2.4 | 0.25 | 2.7 | 0.25 | 2.9 |
| 0.3 | 2.6 | 0.3 | 4.2 | 0.3 | 5.7 | 0.3 | 2.4 | 0.3 | 2.7 | 0.3 | 2.9 |
| 0.35 | 2.6 | 0.35 | 4.2 | 0.35 | 5.7 | 0.35 | 2.4 | 0.35 | 2.7 | 0.35 | 2.9 |
| 0.4 | 2.6 | 0.4 | 4.2 | 0.4 | 5.7 | 0.4 | 2.4 | 0.4 | 2.7 | 0.4 | 2.9 |
| 0.45 | 2.6 | 0.45 | 4.2 | 0.45 | 5.7 | 0.45 | 2.4 | 0.45 | 2.7 | 0.45 | 2.9 |
| 0.5 | 2.6 | 0.5 | 4.1 | 0.5 | 5.6 | 0.5 | 2.4 | 0.5 | 2.7 | 0.5 | 2.9 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0.55 | 2.6 | 0.55 | 4.1 | 0.55 | 5.6 | 0.55 | 2.4 | 0.55 | 2.7 | 0.55 | 2.9 |
| 0.6 | 2.6 | 0.6 | 4.1 | 0.6 | 5.5 | 0.6 | 2.4 | 0.6 | 2.7 | 0.6 | 2.9 |
| 0.65 | 2.6 | 0.65 | 4.1 | 0.65 | 5.4 | 0.65 | 2.4 | 0.65 | 2.7 | 0.65 | 2.9 |
| 0.7 | 2.6 | 0.7 | 4.0 | 0.7 | 5.2 | 0.7 | 2.4 | 0.7 | 2.7 | 0.7 | 2.9 |
| 0.75 | 2.6 | 0.75 | 3.8 | 0.75 | 5.0 | 0.75 | 2.4 | 0.75 | 2.7 | 0.75 | 2.9 |
| 0.8 | 2.4 | 0.8 | 3.6 | 0.8 | 4.7 | 0.8 | 2.3 | 0.8 | 2.6 | 0.8 | 2.8 |
| 0.85 | 2.3 | 0.85 | 3.2 | 0.85 | 4.2 | 0.85 | 2.2 | 0.85 | 2.4 | 0.85 | 2.6 |
| 0.9 | 2.0 | 0.9 | 2.8 | 0.9 | 3.5 | 0.9 | 2.0 | 0.9 | 2.1 | 0.9 | 2.3 |
| 0.95 | 1.7 | 0.95 | 2.1 | 0.95 | 2.5 | 0.95 | 1.6 | 0.95 | 1.7 | 0.95 | 1.8 |
| 1 | 1.2 | 1 | 1.2 | 1 | 1.2 | 1 | 1.2 | 1 | 1.2 | 1 | 1.2 |

| HF-HFO-1234yf-HCFO-1233zdE | | | | | | HF-HCFO-1233zdE-HFO-1243zf | | | | | |
|---|---|---|---|---|---|---|---|---|---|---|---|
| Organics 0.95 F1233zdE + 0.05 F1234yf | | Organics 0.5 F1233zdE + 0.5 F1234yf | | Organics 0.05 F1233zdE + 0.95 F1234yf | | Organics 0.95 F1243zf + 0.05 F1233zdE | | Organics 0.5 F1243zf + 0.5 F1233zdE | | Organics 0.05 F1243zf + 0.95 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.6 | 0 | 4.2 | 0 | 6.5 | 0 | 5.7 | 0 | 3.9 | 0 | 1.6 |
| 0.05 | 2.7 | 0.5 | 5.3 | 0.5 | 7.5 | 0.05 | 6.6 | 0.05 | 5.0 | 0.05 | 2.7 |
| 0.1 | 2.7 | 0.1 | 5.3 | 0.1 | 7.5 | 0.1 | 6.6 | 0.1 | 4.9 | 0.1 | 2.7 |
| 0.15 | 2.7 | 0.15 | 5.3 | 0.15 | 7.5 | 0.15 | 6.6 | 0.15 | 4.9 | 0.15 | 2.7 |
| 0.2 | 2.7 | 0.2 | 5.3 | 0.2 | 7.5 | 0.2 | 6.6 | 0.2 | 4.9 | 0.2 | 2.7 |
| 0.25 | 2.7 | 0.25 | 5.3 | 0.25 | 7.5 | 0.25 | 6.6 | 0.25 | 4.9 | 0.25 | 2.7 |
| 0.3 | 2.7 | 0.3 | 5.3 | 0.3 | 7.5 | 0.3 | 6.6 | 0.3 | 4.9 | 0.3 | 2.7 |
| 0.35 | 2.7 | 0.35 | 5.3 | 0.35 | 7.5 | 0.35 | 6.6 | 0.35 | 4.9 | 0.35 | 2.7 |
| 0.4 | 2.7 | 0.4 | 5.3 | 0.4 | 7.5 | 0.4 | 6.6 | 0.4 | 4.9 | 0.4 | 2.7 |
| 0.45 | 2.7 | 0.45 | 5.3 | 0.45 | 7.5 | 0.45 | 6.6 | 0.45 | 4.9 | 0.45 | 2.7 |
| 0.5 | 2.7 | 0.5 | 5.3 | 0.5 | 7.5 | 0.5 | 6.6 | 0.5 | 4.9 | 0.5 | 2.7 |
| 0.55 | 2.7 | 0.55 | 5.3 | 0.55 | 7.5 | 0.55 | 6.6 | 0.55 | 4.9 | 0.55 | 2.7 |
| 0.6 | 2.7 | 0.6 | 5.3 | 0.6 | 7.5 | 0.6 | 6.6 | 0.6 | 4.9 | 0.6 | 2.7 |
| 0.65 | 2.7 | 0.65 | 5.3 | 0.65 | 7.5 | 0.65 | 6.5 | 0.65 | 4.8 | 0.65 | 2.7 |
| 0.7 | 2.7 | 0.7 | 5.3 | 0.7 | 7.5 | 0.7 | 6.4 | 0.7 | 4.8 | 0.7 | 2.7 |
| 0.75 | 2.7 | 0.75 | 5.2 | 0.75 | 7.4 | 0.75 | 6.3 | 0.75 | 4.6 | 0.75 | 2.7 |
| 0.8 | 2.6 | 0.8 | 4.9 | 0.8 | 7.0 | 0.8 | 6.0 | 0.8 | 4.4 | 0.8 | 2.5 |
| 0.85 | 2.4 | 0.85 | 4.5 | 0.85 | 6.5 | 0.85 | 5.5 | 0.85 | 4.0 | 0.85 | 2.4 |
| 0.9 | 2.1 | 0.9 | 3.8 | 0.9 | 5.4 | 0.9 | 4.6 | 0.9 | 3.4 | 0.9 | 2.1 |
| 0.95 | 1.7 | 0.95 | 2.8 | 0.95 | 3.8 | 0.95 | 3.3 | 0.95 | 2.5 | 0.95 | 1.7 |
| 1 | 1.2 | 1 | 1.2 | 1 | 1.2 | 1 | 1.2 | 1 | 1.2 | 1 | 1.2 |

Example 5: Temperature and Pressure Range of Ternary Mixtures

| Ternary | Boiling point range | |
|---|---|---|
| | Temperature °C. | Pressure bar abs |
| HF-HCFO-1233zdE-HFC-245cb | 0 to 40 | ~1.0 to ~8.9 |
| HF-HCFO-1233xf-HCFO-1233zdE | 0 to 40 | ~0.9 to ~4.0 |
| HF-HFO-1234zeE-HCFO-1233zdE | 0 to 40 | ~1.0 to ~8.8 |
| HF-HFO-1234zeZ-HCFO-1233zdE | 0 to 40 | ~0.9 to ~4.8 |
| HF-HCFO-1233zdE-HFO-1243zf | 0 to 40 | ~1.1 to ~10.2 |
| HF-HFO-1234yf-HCFO-1233zdE | 0 to 40 | ~1.0 to ~11.4 |

Example 6: Decantation Range of Ternary Mixtures

| Ternary | Decantation ranges Mass percentage of HF | | |
|---|---|---|---|
| | Isotherm 0° C. | Isotherm 25° C. | Isotherm 40° C. |
| HF-HCFO-1233zdE-HFC-245cb | 5-80 | 5-75 | 5-75 |
| HF-HCFO-1233xf-HCFO-1233zdE | 5-80 | 5-75 | 5-65 |
| HF-HFO-1234zeE-HCFO-1233zdE | 5-70 | 5-65 | 10-50 |
| HF-HFO-1234zeZ-HCFO-1233zdE | 5-80 | 5-75 | 5-65 |
| HF-HCFO-1233zdE-HFO-124zf | 5-75 | 5-65 | 15-45 |
| HF-HFO-1234yf-HCFO-1233zdE | 5-75 | 5-70 | 15-55 |

Example 7: Quaternary Mixtures, Isotherm at 25° C.

| HF-HCFO-1233xf-HCFO-1233zdE-HFC-245cb ||||||||
|---|---|---|---|---|---|---|---|
| Organics 0.9 F1233xf + 0.05 F1233zdE + 0.05 F245cb || Organics 0.4 F1233xf + 0.3 F1233zdE + 0.3 F245cb || Organics 0.05 F1233xf + 0.9 F1233zdE + 0.05 F245cb || Organics 0.05 F1233xf + 0.05 F1233zdE + 0.9 F245cb ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 2.4 | 0 | 1.5 | 0 | 4.3 |
| 0.05 | 2.8 | 0.05 | 3.6 | 0.05 | 2.6 | 0.05 | 5.5 |
| 0.1 | 2.8 | 0.1 | 3.6 | 0.1 | 2.6 | 0.1 | 5.5 |
| 0.15 | 2.8 | 0.15 | 3.6 | 0.15 | 2.6 | 0.15 | 5.5 |
| 0.2 | 2.8 | 0.2 | 3.6 | 0.2 | 2.6 | 0.2 | 5.5 |
| 0.25 | 2.8 | 0.25 | 3.6 | 0.25 | 2.6 | 0.25 | 5.5 |
| 0.3 | 2.8 | 0.3 | 3.6 | 0.3 | 2.6 | 0.3 | 5.5 |
| 0.35 | 2.8 | 0.35 | 3.6 | 0.35 | 2.6 | 0.35 | 5.5 |
| 0.4 | 2.8 | 0.4 | 3.6 | 0.4 | 2.6 | 0.4 | 5.5 |
| 0.45 | 2.8 | 0.45 | 3.6 | 0.45 | 2.6 | 0.45 | 5.5 |
| 0.5 | 2.8 | 0.5 | 3.6 | 0.5 | 2.6 | 0.5 | 5.5 |
| 0.55 | 2.8 | 0.55 | 3.6 | 0.55 | 2.6 | 0.55 | 5.5 |
| 0.6 | 2.8 | 0.6 | 3.7 | 0.6 | 2.6 | 0.6 | 5.5 |
| 0.65 | 2.8 | 0.65 | 3.7 | 0.65 | 2.6 | 0.65 | 5.5 |
| 0.7 | 2.8 | 0.7 | 3.7 | 0.7 | 2.6 | 0.7 | 5.6 |
| 0.75 | 2.8 | 0.75 | 3.7 | 0.75 | 2.6 | 0.75 | 5.6 |
| 0.8 | 2.7 | 0.8 | 3.7 | 0.8 | 2.5 | 0.8 | 5.6 |
| 0.85 | 2.5 | 0.85 | 3.4 | 0.85 | 2.4 | 0.85 | 5.5 |
| 0.9 | 2.2 | 0.9 | 2.9 | 0.9 | 2.1 | 0.9 | 4.8 |
| 0.95 | 1.8 | 0.95 | 2.2 | 0.95 | 1.7 | 0.95 | 3.4 |
| 1 | 1.2 | 1 | 1.2 | 1 | 1.2 | 1 | 1.2 |

| HF-HCFO-1233xf-HCFO-1233zdE-HFO-1234zeE ||||||||
|---|---|---|---|---|---|---|---|
| Organics 0.9 F1233xf + 0.05 F1233zdE + 0.05 F1234zeE || Organics 0.05 F1233xf + 0.9 F1233zdE + 0.05 F1234zeE || Organics 0.05 F1233xf + 0.05 F1233zdE + 0.9 F1234zeE || Organics 0.4 F1233xf + 0.3 F1233zdE + 0.3 F1234zeE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.6 | 0 | 2.5 |
| 0.05 | 2.8 | 0.05 | 2.6 | 0.05 | 5.5 | 0.05 | 3.6 |
| 0.1 | 2.8 | 0.1 | 2.6 | 0.1 | 5.5 | 0.1 | 3.6 |
| 0.15 | 2.8 | 0.15 | 2.6 | 0.15 | 5.5 | 0.15 | 3.6 |
| 0.2 | 2.8 | 0.2 | 2.6 | 0.2 | 5.5 | 0.2 | 3.6 |
| 0.25 | 2.8 | 0.25 | 2.6 | 0.25 | 5.5 | 0.25 | 3.6 |
| 0.3 | 2.8 | 0.3 | 2.6 | 0.3 | 5.5 | 0.3 | 3.6 |
| 0.35 | 2.8 | 0.35 | 2.6 | 0.35 | 5.5 | 0.35 | 3.6 |
| 0.4 | 2.8 | 0.4 | 2.6 | 0.4 | 5.5 | 0.4 | 3.6 |
| 0.45 | 2.8 | 0.45 | 2.6 | 0.45 | 5.5 | 0.45 | 3.6 |
| 0.5 | 2.8 | 0.5 | 2.6 | 0.5 | 5.5 | 0.5 | 3.6 |
| 0.55 | 2.8 | 0.55 | 2.6 | 0.55 | 5.4 | 0.55 | 3.5 |
| 0.6 | 2.8 | 0.6 | 2.6 | 0.6 | 5.4 | 0.6 | 3.5 |
| 0.65 | 2.8 | 0.65 | 2.6 | 0.65 | 5.3 | 0.65 | 3.5 |
| 0.7 | 2.8 | 0.7 | 2.6 | 0.7 | 5.1 | 0.7 | 3.5 |
| 0.75 | 2.8 | 0.75 | 2.6 | 0.75 | 4.9 | 0.75 | 3.3 |
| 0.8 | 2.6 | 0.8 | 2.5 | 0.8 | 4.6 | 0.8 | 3.2 |
| 0.85 | 2.4 | 0.85 | 2.3 | 0.85 | 4.1 | 0.85 | 2.9 |

| | | | | | | | |
|---|---|---|---|---|---|---|---|
| 0.9 | 2.2 | 0.9 | 2.0 | 0.9 | 3.4 | 0.9 | 2.5 |
| 0.95 | 1.7 | 0.95 | 1.7 | 0.95 | 2.5 | 0.95 | 1.9 |
| 1 | 1.2 | 1 | 1.2 | 1 | 1.2 | 1 | 1.2 |

HF-HCFO-1233xf-HCFO-1233zdE-HFO-1234zeZ

| Organics 0.9 F1233xf + 0.05 F1233zdE + 0.05 F1234zeZ | | Organics 0.05 F1233xf + 0.9 F1233zdE + 0.05 F1234zeZ | | Organics 0.05 F1233xf + 0.05 F1233zdE + 0.9 F1234zeZ | | Organics 0.4 F1233xf + 0.3 F1233zdE + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 1.4 | 0 | 1.8 | 0 | 1.6 |
| 0.05 | 2.7 | 0.05 | 2.5 | 0.05 | 2.9 | 0.05 | 2.7 |
| 0.1 | 2.7 | 0.1 | 2.5 | 0.1 | 2.9 | 0.1 | 2.7 |
| 0.15 | 2.7 | 0.15 | 2.5 | 0.15 | 2.9 | 0.15 | 2.7 |
| 0.2 | 2.7 | 0.2 | 2.5 | 0.2 | 2.9 | 0.2 | 2.7 |
| 0.25 | 2.7 | 0.25 | 2.5 | 0.25 | 2.9 | 0.25 | 2.7 |
| 0.3 | 2.7 | 0.3 | 2.5 | 0.3 | 2.9 | 0.3 | 2.7 |
| 0.35 | 2.7 | 0.35 | 2.5 | 0.35 | 2.9 | 0.35 | 2.7 |
| 0.4 | 2.7 | 0.4 | 2.5 | 0.4 | 2.9 | 0.4 | 2.7 |
| 0.45 | 2.7 | 0.45 | 2.5 | 0.45 | 2.9 | 0.45 | 2.7 |
| 0.5 | 2.7 | 0.5 | 2.5 | 0.5 | 2.9 | 0.5 | 2.7 |
| 0.55 | 2.7 | 0.55 | 2.5 | 0.55 | 2.9 | 0.55 | 2.7 |
| 0.6 | 2.7 | 0.6 | 2.5 | 0.6 | 2.9 | 0.6 | 2.7 |
| 0.65 | 2.7 | 0.65 | 2.5 | 0.65 | 2.9 | 0.65 | 2.7 |
| 0.7 | 2.7 | 0.7 | 2.5 | 0.7 | 2.9 | 0.7 | 2.7 |
| 0.75 | 2.7 | 0.75 | 2.5 | 0.75 | 2.9 | 0.75 | 2.7 |
| 0.8 | 2.5 | 0.8 | 2.4 | 0.8 | 2.8 | 0.8 | 2.6 |
| 0.85 | 2.4 | 0.85 | 2.2 | 0.85 | 2.6 | 0.85 | 2.4 |
| 0.9 | 2.1 | 0.9 | 2.0 | 0.9 | 2.3 | 0.9 | 2.1 |
| 0.95 | 1.7 | 0.95 | 1.6 | 0.95 | 1.8 | 0.95 | 1.7 |
| 1 | 1.2 | 1 | 1.2 | 1 | 1.2 | 1 | 1.2 |

HF-HCFO-1233xf-HCFO-1233zdE-HFO-1243zf

| Organics 0.9 F1233xf + 0.05 F1233zdE + 0.05 F1243zf | | Organics 0.05 F1233xf + 0.9 F1233zdE + 0.05 F1243zf | | Organics 0.05 F1233xf + 0.05 F1233zdE + 0.9 F1243zf | | Organics 0.4 F1233xf + 0.3 F1233zdE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 5.5 | 0 | 3.0 |
| 0.05 | 2.9 | 0.05 | 2.7 | 0.05 | 6.4 | 0.05 | 4.1 |
| 0.1 | 2.9 | 0.1 | 2.7 | 0.1 | 6.5 | 0.1 | 4.1 |
| 0.15 | 2.9 | 0.15 | 2.7 | 0.15 | 6.5 | 0.15 | 4.1 |
| 0.2 | 2.9 | 0.2 | 2.7 | 0.2 | 6.5 | 0.2 | 4.1 |
| 0.25 | 2.9 | 0.25 | 2.7 | 0.25 | 6.5 | 0.25 | 4.1 |
| 0.3 | 2.9 | 0.3 | 2.7 | 0.3 | 6.5 | 0.3 | 4.1 |
| 0.35 | 2.9 | 0.35 | 2.7 | 0.35 | 6.5 | 0.35 | 4.1 |
| 0.4 | 2.9 | 0.4 | 2.7 | 0.4 | 6.5 | 0.4 | 4.1 |
| 0.45 | 2.9 | 0.45 | 2.7 | 0.45 | 6.5 | 0.45 | 4.1 |
| 0.5 | 2.9 | 0.5 | 2.7 | 0.5 | 6.4 | 0.5 | 4.1 |
| 0.55 | 2.9 | 0.55 | 2.7 | 0.55 | 6.4 | 0.55 | 4.1 |
| 0.6 | 2.9 | 0.6 | 2.7 | 0.6 | 6.4 | 0.6 | 4.0 |
| 0.65 | 2.9 | 0.65 | 2.7 | 0.65 | 6.4 | 0.65 | 4.0 |
| 0.7 | 2.9 | 0.7 | 2.7 | 0.7 | 6.3 | 0.7 | 4.0 |
| 0.75 | 2.9 | 0.75 | 2.7 | 0.75 | 6.1 | 0.75 | 3.9 |
| 0.8 | 2.7 | 0.8 | 2.6 | 0.8 | 5.8 | 0.8 | 3.7 |
| 0.85 | 2.5 | 0.85 | 2.4 | 0.85 | 5.3 | 0.85 | 3.4 |
| 0.9 | 2.2 | 0.9 | 2.1 | 0.9 | 4.5 | 0.9 | 2.9 |
| 0.95 | 1.8 | 0.95 | 1.7 | 0.95 | 3.2 | 0.95 | 2.2 |
| 1 | 1.2 | 1 | 1.2 | 1 | 1.2 | 1 | 1.2 |

-continued

| \multicolumn{8}{c}{HF-HFC-245cb-HCFO-1233zdE-HFO-1234zeE} |
|---|---|---|---|---|---|---|---|
| \multicolumn{2}{c}{Organics 0.9 F245cb + 0.05 F1233zdE + 0.05 F1234zeE} | \multicolumn{2}{c}{Organics 0.05 F245cb + 0.9 F1233zdE + 0.05 F1234zeE} | \multicolumn{2}{c}{Organics 0.05 F245cb + 0.05 F1233zdE + 0.9 F1234zeE} | \multicolumn{2}{c}{Organics 0.4 F245cb + 0.3 F1233zdE + 0.3 F1234zeE} |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 1.7 | 0 | 4.7 | 0 | 3.8 |
| 0.05 | 5.7 | 0.05 | 2.8 | 0.05 | 5.7 | 0.05 | 4.9 |
| 0.1 | 5.7 | 0.1 | 2.8 | 0.1 | 5.7 | 0.1 | 4.9 |
| 0.15 | 5.7 | 0.15 | 2.8 | 0.15 | 5.7 | 0.15 | 4.9 |
| 0.2 | 5.7 | 0.2 | 2.8 | 0.2 | 5.7 | 0.2 | 4.9 |
| 0.25 | 5.7 | 0.25 | 2.8 | 0.25 | 5.7 | 0.25 | 4.9 |
| 0.3 | 5.7 | 0.3 | 2.8 | 0.3 | 5.7 | 0.3 | 4.9 |
| 0.35 | 5.7 | 0.35 | 2.8 | 0.35 | 5.7 | 0.35 | 4.9 |
| 0.4 | 5.7 | 0.4 | 2.8 | 0.4 | 5.7 | 0.4 | 4.9 |
| 0.45 | 5.7 | 0.45 | 2.8 | 0.45 | 5.7 | 0.45 | 4.9 |
| 0.5 | 5.7 | 0.5 | 2.8 | 0.5 | 5.7 | 0.5 | 4.9 |
| 0.55 | 5.7 | 0.55 | 2.8 | 0.55 | 5.6 | 0.55 | 4.9 |
| 0.6 | 5.7 | 0.6 | 2.8 | 0.6 | 5.5 | 0.6 | 4.9 |
| 0.65 | 5.7 | 0.65 | 2.8 | 0.65 | 5.5 | 0.65 | 4.9 |
| 0.7 | 5.7 | 0.7 | 2.8 | 0.7 | 5.3 | 0.7 | 4.9 |
| 0.75 | 5.7 | 0.75 | 2.8 | 0.75 | 5.1 | 0.75 | 4.9 |
| 0.8 | 5.7 | 0.8 | 2.7 | 0.8 | 4.8 | 0.8 | 4.7 |
| 0.85 | 5.6 | 0.85 | 2.5 | 0.85 | 4.3 | 0.85 | 4.3 |
| 0.9 | 4.8 | 0.9 | 2.2 | 0.9 | 3.6 | 0.9 | 3.7 |
| 0.95 | 3.4 | 0.95 | 1.8 | 0.95 | 2.6 | 0.95 | 2.7 |
| 1 | 1.2 | 1 | 1.2 | 1 | 1.2 | 1 | 1.2 |

| \multicolumn{8}{c}{HF-HFC-245cb-HCFO-1233zdE-HFO-1234zeZ} |
|---|---|---|---|---|---|---|---|
| \multicolumn{2}{c}{Organics 0.9 F245cb + 0.05 F1233zdE + 0.05 F1234zeZ} | \multicolumn{2}{c}{Organics 0.05 F245cb + 0.9 F1233zdE + 0.05 F1234zeZ} | \multicolumn{2}{c}{Organics 0.05 F245cb + 0.05 F1233zdE + 0.9 F1234zeZ} | \multicolumn{2}{c}{Organics 0.4 F245cb + 0.3 F1233zdE + 0.3 F1234zeZ} |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.5 | 0 | 1.9 | 0 | 2.8 |
| 0.05 | 5.5 | 0.05 | 2.6 | 0.05 | 3.0 | 0.05 | 3.9 |
| 0.1 | 5.5 | 0.1 | 2.6 | 0.1 | 3.0 | 0.1 | 3.9 |
| 0.15 | 5.5 | 0.15 | 2.6 | 0.15 | 3.0 | 0.15 | 3.9 |
| 0.2 | 5.5 | 0.2 | 2.6 | 0.2 | 3.0 | 0.2 | 3.9 |
| 0.25 | 5.5 | 0.25 | 2.6 | 0.25 | 3.0 | 0.25 | 3.9 |
| 0.3 | 5.5 | 0.3 | 2.6 | 0.3 | 3.0 | 0.3 | 4.0 |
| 0.35 | 5.5 | 0.35 | 2.6 | 0.35 | 3.0 | 0.35 | 4.0 |
| 0.4 | 5.5 | 0.4 | 2.6 | 0.4 | 3.0 | 0.4 | 4.0 |
| 0.45 | 5.5 | 0.45 | 2.6 | 0.45 | 3.0 | 0.45 | 4.0 |
| 0.5 | 5.5 | 0.5 | 2.6 | 0.5 | 3.0 | 0.5 | 4.0 |
| 0.55 | 5.5 | 0.55 | 2.6 | 0.55 | 3.0 | 0.55 | 4.0 |
| 0.6 | 5.5 | 0.6 | 2.6 | 0.6 | 3.0 | 0.6 | 4.0 |
| 0.65 | 5.5 | 0.65 | 2.7 | 0.65 | 3.1 | 0.65 | 4.0 |
| 0.7 | 5.6 | 0.7 | 2.7 | 0.7 | 3.1 | 0.7 | 4.1 |
| 0.75 | 5.6 | 0.75 | 2.7 | 0.75 | 3.1 | 0.75 | 4.1 |
| 0.8 | 5.6 | 0.8 | 2.6 | 0.8 | 2.9 | 0.8 | 4.1 |
| 0.85 | 5.5 | 0.85 | 2.4 | 0.85 | 2.7 | 0.85 | 3.8 |
| 0.9 | 4.8 | 0.9 | 2.1 | 0.9 | 2.4 | 0.9 | 3.3 |
| 0.95 | 3.4 | 0.95 | 1.7 | 0.95 | 1.9 | 0.95 | 2.5 |
| 1 | 1.2 | 1 | 1.2 | 1 | 1.2 | 1 | 1.2 |

| \multicolumn{8}{c}{HF-HFC-245cb-HCFO-1233zdE-HFO-1243zf} |
|---|---|---|---|---|---|---|---|
| \multicolumn{2}{c}{Organics 0.9 F245cb + 0.05 F1233zdE + 0.05 F1243zf} | \multicolumn{2}{c}{Organics 0.05 F245cb + 0.9 F1233zdE + 0.05 F1243zf} | \multicolumn{2}{c}{Organics 0.05 F245cb + 0.05 F1233zdE + 0.9 F1243zf} | \multicolumn{2}{c}{Organics 0.4 F245cb + 0.3 F1233zdE + 0.3 F1243zf} |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 1.8 | 0 | 5.6 | 0 | 4.2 |
| 0.05 | 5.7 | 0.05 | 2.9 | 0.05 | 6.6 | 0.05 | 5.3 |
| 0.1 | 5.7 | 0.1 | 2.9 | 0.1 | 6.6 | 0.1 | 5.3 |

-continued

| | | | | | | | |
|---|---|---|---|---|---|---|---|
| 0.15 | 5.7 | 0.15 | 2.9 | 0.15 | 6.6 | 0.15 | 5.3 |
| 0.2 | 5.7 | 0.2 | 2.9 | 0.2 | 6.6 | 0.2 | 5.3 |
| 0.25 | 5.7 | 0.25 | 2.9 | 0.25 | 6.6 | 0.25 | 5.3 |
| 0.3 | 5.7 | 0.3 | 2.9 | 0.3 | 6.6 | 0.3 | 5.3 |
| 0.35 | 5.7 | 0.35 | 2.9 | 0.35 | 6.6 | 0.35 | 5.3 |
| 0.4 | 5.7 | 0.4 | 2.9 | 0.4 | 6.6 | 0.4 | 5.3 |
| 0.45 | 5.7 | 0.45 | 2.9 | 0.45 | 6.6 | 0.45 | 5.3 |
| 0.5 | 5.7 | 0.5 | 2.9 | 0.5 | 6.6 | 0.5 | 5.3 |
| 0.55 | 5.7 | 0.55 | 2.9 | 0.55 | 6.6 | 0.55 | 5.3 |
| 0.6 | 5.7 | 0.6 | 2.9 | 0.6 | 6.5 | 0.6 | 5.3 |
| 0.65 | 5.7 | 0.65 | 2.9 | 0.65 | 6.5 | 0.65 | 5.3 |
| 0.7 | 5.8 | 0.7 | 2.9 | 0.7 | 6.4 | 0.7 | 5.3 |
| 0 | 5.8 | 0.75 | 2.9 | 0.75 | 6.2 | 0.75 | 5.3 |
| 0.8 | 5.8 | 0.8 | 2.8 | 0.8 | 6.0 | 0.8 | 5.1 |
| 0.85 | 5.7 | 0.85 | 2.6 | 0.85 | 5.5 | 0.85 | 4.7 |
| 0.9 | 4.9 | 0.9 | 2.3 | 0.9 | 4.7 | 0.9 | 4.1 |
| 0.95 | 3.5 | 0.95 | 1.8 | 0.95 | 3.3 | 0.95 | 2.9 |
| 1 | 1.2 | 1 | 1.2 | 1 | 1.2 | 1 | 1.2 |

HF-HCFO-1233zdE-HFO-1234zeE-HFO-1234zeZ

| Organics 0.9 1233zdE + 0.05 1234zeE + 0.05 1234zeZ | | Organics 0.05 1233zdE + 0.9 1234zeE + 0.05 1234zeZ | | Organics 0.05 1233zdE + 0.05 1234zeE + 0.9 1234zeZ | | Organics 0.4 1233zdE + 0.3 1234zeE + 0.3 1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 4.5 | 0 | 1.9 | 0 | 2.6 |
| 0.05 | 2.6 | 0.05 | 5.5 | 0.05 | 3.0 | 0.05 | 3.7 |
| 0.1 | 2.6 | 0.1 | 5.5 | 0.1 | 3.0 | 0.1 | 3.6 |
| 0.15 | 2.6 | 0.15 | 5.5 | 0.15 | 3.0 | 0.15 | 3.6 |
| 0.2 | 2.6 | 0.2 | 5.5 | 0.2 | 3.0 | 0.2 | 3.6 |
| 0.25 | 2.6 | 0.25 | 5.5 | 0.25 | 3.0 | 0.25 | 3.6 |
| 0.3 | 2.6 | 0.3 | 5.5 | 0.3 | 3.0 | 0.3 | 3.6 |
| 0.35 | 2.6 | 0.35 | 5.5 | 0.35 | 3.0 | 0.35 | 3.6 |
| 0.4 | 2.6 | 0.4 | 5.5 | 0.4 | 3.0 | 0.4 | 3.6 |
| 0.45 | 2.6 | 0.45 | 5.5 | 0.45 | 3.0 | 0.45 | 3.6 |
| 0.5 | 2.6 | 0.5 | 5.5 | 0.5 | 3.0 | 0.5 | 3.6 |
| 0.55 | 2.6 | 0.55 | 5.4 | 0.55 | 3.0 | 0.55 | 3.6 |
| 0.6 | 2.6 | 0.6 | 5.4 | 0.6 | 3.0 | 0.6 | 3.6 |
| 0.65 | 2.6 | 0.65 | 5.3 | 0.65 | 3.0 | 0.65 | 3.5 |
| 0.7 | 2.6 | 0.7 | 5.1 | 0.7 | 3.0 | 0.7 | 3.5 |
| 0.75 | 2.6 | 0.75 | 4.9 | 0.75 | 3.0 | 0.75 | 3.4 |
| 0.8 | 2.5 | 0.8 | 4.6 | 0.8 | 2.9 | 0.8 | 3.2 |
| 0.85 | 2.3 | 0.85 | 4.1 | 0.85 | 2.7 | 0.85 | 2.9 |
| 0.9 | 2.0 | 0.9 | 3.4 | 0.9 | 2.3 | 0.9 | 2.5 |
| 0.95 | 1.7 | 0.95 | 2.5 | 0.95 | 1.9 | 0.95 | 2.0 |
| 1 | 1.2 | 1 | 1.2 | 1 | 1.2 | 1 | 1.2 |

HF-HCFO-1233zdE-HFO-1234zeE-HFO-1243zf

| Organics 0.9 F1233zdE + 0.05 F1234zeE + 0.05 F1243zf | | Organics 0.05 F1233zdE + 0.9 F1234zeE + 0.05 F1243zf | | Organics 0.05 F1233zdE + 0.05 F1234zeE + 0.9 F1243zf | | Organics 0.4 F1233zdE + 0.3 F1234zeE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 4.8 | 0 | 5.6 | 0 | 3.9 |
| 0.05 | 2.9 | 0.05 | 5.7 | 0.05 | 6.6 | 0.05 | 5.0 |
| 0.1 | 2.9 | 0.1 | 5.7 | 0.1 | 6.6 | 0.1 | 5.0 |
| 0.15 | 2.9 | 0.15 | 5.7 | 0.15 | 6.6 | 0.15 | 5.0 |
| 0.2 | 2.9 | 0.2 | 5.7 | 0.2 | 6.6 | 0.2 | 5.0 |
| 0.25 | 2.9 | 0.25 | 5.7 | 0.25 | 6.6 | 0.25 | 5.0 |
| 0.3 | 2.9 | 0.3 | 5.7 | 0.3 | 6.6 | 0.3 | 5.0 |
| 0.35 | 2.9 | 0.35 | 5.7 | 0.35 | 6.6 | 0.35 | 5.0 |
| 0.4 | 2.9 | 0.4 | 5.7 | 0.4 | 6.6 | 0.4 | 4.9 |
| 0.45 | 2.9 | 0.45 | 5.7 | 0.45 | 6.6 | 0.45 | 4.9 |
| 0.5 | 2.9 | 0.5 | 5.7 | 0.5 | 6.6 | 0.5 | 4.9 |
| 0.55 | 2.9 | 0.55 | 5.6 | 0.55 | 6.5 | 0.55 | 4.9 |
| 0.6 | 2.9 | 0.6 | 5.6 | 0.6 | 6.5 | 0.6 | 4.9 |
| 0.65 | 2.9 | 0.65 | 5.5 | 0.65 | 6.5 | 0.65 | 4.9 |
| 0.7 | 2.8 | 0.7 | 5.3 | 0.7 | 6.4 | 0.7 | 4.8 |
| 0.75 | 2.8 | 0.75 | 5.1 | 0.75 | 6.2 | 0.75 | 4.6 |
| 0.8 | 2.7 | 0.8 | 4.8 | 0.8 | 5.9 | 0.8 | 4.3 |
| 0.85 | 2.5 | 0.85 | 4.3 | 0.85 | 5.4 | 0.85 | 3.9 |

-continued

| | | | | | | | |
|---|---|---|---|---|---|---|---|
| 0.9 | 2.2 | 0.9 | 3.6 | 0.9 | 4.6 | 0.9 | 3.3 |
| 0.95 | 1.8 | 0.95 | 2.6 | 0.95 | 3.3 | 0.95 | 2.5 |
| 1 | 1.2 | 1 | 1.2 | 1 | 1.2 | 1 | 1.2 |

HF-HCFO-1233zdE-HFO-1234zeZ-HFO-1243zf

| Organics 0.9 F1233zdE + 0.05 F1234zeZ + 0.05 F1243zf | | Organics 0.05 F1233zdE + 0.9 F1234zeZ + 0.05 F1243zf | | Organics 0.05 F1233zdE + 0.05 F1234zeZ + 0.9 F1243zf | | Organics 0.4 F1233zdE + 0.3 F1234zeZ + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.6 | 0 | 2.0 | 0 | 5.5 | 0 | 3.0 |
| 0.05 | 2.7 | 0.05 | 3.1 | 0.05 | 6.4 | 0.05 | 4.1 |
| 0.1 | 2.7 | 0.1 | 3.1 | 0.1 | 6.5 | 0.1 | 4.1 |
| 0.15 | 2.7 | 0.15 | 3.1 | 0.15 | 6.5 | 0.15 | 4.1 |
| 0.2 | 2.7 | 0.2 | 3.1 | 0.2 | 6.5 | 0.2 | 4.1 |
| 0.25 | 2.7 | 0.25 | 3.1 | 0.25 | 6.5 | 0.25 | 4.1 |
| 0.3 | 2.7 | 0.3 | 3.1 | 0.3 | 6.4 | 0.3 | 4.1 |
| 0.35 | 2.7 | 0.35 | 3.1 | 0.35 | 6.4 | 0.35 | 4.1 |
| 0.4 | 2.7 | 0.4 | 3.1 | 0.4 | 6.4 | 0.4 | 4.1 |
| 0.45 | 2.7 | 0.45 | 3.1 | 0.45 | 6.4 | 0.45 | 4.1 |
| 0.5 | 2.7 | 0.5 | 3.1 | 0.5 | 6.4 | 0.5 | 4.1 |
| 0.55 | 2.7 | 0.55 | 3.1 | 0.55 | 6.4 | 0.55 | 4.1 |
| 0.6 | 2.7 | 0.6 | 3.1 | 0.6 | 6.4 | 0.6 | 4.1 |
| 0.65 | 2.7 | 0.65 | 3.1 | 0.65 | 6.3 | 0.65 | 4.0 |
| 0.7 | 2.7 | 0.7 | 3.1 | 0.7 | 6.3 | 0.7 | 4.0 |
| 0.75 | 2.7 | 0.75 | 3.1 | 0.75 | 6.1 | 0.75 | 3.9 |
| 0.8 | 2.6 | 0.8 | 3.0 | 0.8 | 5.8 | 0.8 | 3.7 |
| 0.85 | 2.4 | 0.85 | 2.7 | 0.85 | 5.3 | 0.85 | 3.4 |
| 0.9 | 2.1 | 0.9 | 2.4 | 0.9 | 4.5 | 0.9 | 2.9 |
| 0.95 | 1.7 | 0.95 | 1.9 | 0.95 | 3.2 | 0.95 | 2.2 |
| 1 | 1.2 | 1 | 1.2 | 1 | 1.2 | 1 | 1.2 |

HF-HFO-1234yf-HCFO-1233zdE-HFC-245cb

| Organics 0.9 F1234yf + 0.05 F1233zdE + 0.05 F245cb | | Organics 0.4 F1234yf + 0.3 F1233zdE + 0.3 F245cb | | Organics 0.05 F1234yf + 0.9 F1233zdE + 0.05 F245cb | | Organics 0.05 F1234yf + 0.05 F1233zdE + 0.9 F245cb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.6 | 0 | 1.8 | 0 | 4.6 |
| 0.05 | 7.4 | 0.05 | 5.7 | 0.05 | 2.9 | 0.05 | 5.8 |
| 0.1 | 7.4 | 0.1 | 5.7 | 0.1 | 2.9 | 0.1 | 5.8 |
| 0.15 | 7.4 | 0.15 | 5.7 | 0.15 | 2.9 | 0.15 | 5.8 |
| 0.2 | 7.4 | 0.2 | 5.7 | 0.2 | 2.9 | 0.2 | 5.8 |
| 0.25 | 7.4 | 0.25 | 5.7 | 0.25 | 2.9 | 0.25 | 5.8 |
| 0.3 | 7.4 | 0.3 | 5.7 | 0.3 | 2.9 | 0.3 | 5.8 |
| 0.35 | 7.4 | 0.35 | 5.7 | 0.35 | 2.9 | 0.35 | 5.8 |
| 0.4 | 7.4 | 0.4 | 5.7 | 0.4 | 2.9 | 0.4 | 5.8 |
| 0.45 | 7.4 | 0.45 | 5.7 | 0.45 | 2.9 | 0.45 | 5.8 |
| 0.5 | 7.4 | 0.5 | 5.7 | 0.5 | 2.9 | 0.5 | 5.8 |
| 0.55 | 7.4 | 0.55 | 5.7 | 0.55 | 2.9 | 0.55 | 5.8 |
| 0.6 | 7.4 | 0.6 | 5.7 | 0.6 | 2.9 | 0.6 | 5.8 |
| 0.65 | 7.4 | 0.65 | 5.8 | 0.65 | 2.9 | 0.65 | 5.8 |
| 0.7 | 7.4 | 0.7 | 5.8 | 0.7 | 2.9 | 0.7 | 5.8 |
| 0.75 | 7.3 | 0.75 | 5.8 | 0.75 | 2.9 | 0.75 | 5.8 |
| 0.8 | 7.0 | 0.8 | 5.6 | 0.8 | 2.8 | 0.8 | 5.8 |
| 0.85 | 6.4 | 0.85 | 5.1 | 0.85 | 2.6 | 0.85 | 5.7 |
| 0.9 | 5.4 | 0.9 | 4.4 | 0.9 | 2.3 | 0.9 | 4.9 |
| 0.95 | 3.7 | 0.95 | 3.1 | 0.95 | 1.8 | 0.95 | 3.5 |
| 1 | 1.2 | 1 | 1.2 | 1 | 1.2 | 1 | 1.2 |

-continued

HF-HCFO-1233xf-HFO-1234yf-HCFO-1233zdE

| Organics 0.9 F1233xf + 0.05 F1234yf + 0.05 F1233zdE | | Organics 0.05 F1233xf + 0.9 F1234yf + 0.05 F1233zdE | | Organics 0.05 F1233xf + 0.05 F1234yf + 0.9 F1233zdE | | Organics 0.4 F1233xf + 0.3 F1234yf + 0.3 F1233zdE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 6.3 | 0 | 1.7 | 0 | 3.2 |
| 0.05 | 3.0 | 0.05 | 7.3 | 0.05 | 2.8 | 0.05 | 4.3 |
| 0.1 | 3.0 | 0.1 | 7.3 | 0.1 | 2.8 | 0.1 | 4.3 |
| 0.15 | 3.0 | 0.15 | 7.3 | 0.15 | 2.8 | 0.15 | 4.3 |
| 0.2 | 2.9 | 0.2 | 7.3 | 0.2 | 2.8 | 0.2 | 4.3 |
| 0.25 | 2.9 | 0.25 | 7.3 | 0.25 | 2.8 | 0.25 | 4.3 |
| 0.3 | 2.9 | 0.3 | 7.3 | 0.3 | 2.8 | 0.3 | 4.3 |
| 0.35 | 2.9 | 0.35 | 7.3 | 0.35 | 2.8 | 0.35 | 4.3 |
| 0.4 | 2.9 | 0.4 | 7.3 | 0.4 | 2.8 | 0.4 | 4.3 |
| 0.45 | 2.9 | 0.45 | 7.3 | 0.45 | 2.7 | 0.45 | 4.3 |
| 0.5 | 2.9 | 0.5 | 7.3 | 0.5 | 2.7 | 0.5 | 4.3 |
| 0.55 | 2.9 | 0.55 | 7.3 | 0.55 | 2.7 | 0.55 | 4.3 |
| 0.6 | 2.9 | 0.6 | 7.3 | 0.6 | 2.7 | 0.6 | 4.3 |
| 0.65 | 2.9 | 0.65 | 7.3 | 0.65 | 2.7 | 0.65 | 4.3 |
| 0.7 | 2.9 | 0.7 | 7.3 | 0.7 | 2.7 | 0.7 | 4.3 |
| 0.75 | 2.9 | 0.75 | 7.1 | 0.75 | 2.7 | 0.75 | 4.2 |
| 0.8 | 2.8 | 0.8 | 6.8 | 0.8 | 2.6 | 0.8 | 4.0 |
| 0.85 | 2.6 | 0.85 | 6.2 | 0.85 | 2.4 | 0.85 | 3.7 |
| 0.9 | 2.3 | 0.9 | 5.3 | 0.9 | 2.1 | 0.9 | 3.1 |
| 0.95 | 1.8 | 0.95 | 3.7 | 0.95 | 1.7 | 0.95 | 2.3 |
| 1 | 1.2 | 1 | 1.2 | 1 | 1.2 | 1 | 1.2 |

HF-HFO-1234yf-HFO-1234zeE-HCFO-1233zdE

| Organics 0.9 F1234yf + 0.05 F1234zeE + 0.05 F1233zdE | | Organics 0.05 F1234yf + 0.9 F1234zeE + 0.05 F1233zdE | | Organics 0.05 F1234yf + 0.05 F1234zeE + 0.9 F1233zdE | | Organics 0.4 F1234yf + 0.3 F1234zeE + 0.3 F1233zdE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.8 | 0 | 1.8 | 0 | 4.7 |
| 0.05 | 7.4 | 0.05 | 5.8 | 0.05 | 2.9 | 0.05 | 5.7 |
| 0.1 | 7.4 | 0.1 | 5.8 | 0.1 | 2.9 | 0.1 | 5.7 |
| 0.15 | 7.4 | 0.15 | 5.8 | 0.15 | 2.9 | 0.15 | 5.7 |
| 0.2 | 7.4 | 0.2 | 5.8 | 0.2 | 2.9 | 0.2 | 5.7 |
| 0.25 | 7.4 | 0.25 | 5.8 | 0.25 | 2.9 | 0.25 | 5.7 |
| 0.3 | 7.4 | 0.3 | 5.8 | 0.3 | 2.9 | 0.3 | 5.7 |
| 0.35 | 7.4 | 0.35 | 5.8 | 0.35 | 2.9 | 0.35 | 5.7 |
| 0.4 | 7.4 | 0.4 | 5.8 | 0.4 | 2.9 | 0.4 | 5.7 |
| 0.45 | 7.4 | 0.45 | 5.8 | 0.45 | 2.9 | 0.45 | 5.7 |
| 0.5 | 7.4 | 0.5 | 5.7 | 0.5 | 2.9 | 0.5 | 5.7 |
| 0.55 | 7.4 | 0.55 | 5.7 | 0.55 | 2.9 | 0.55 | 5.7 |
| 0.6 | 7.4 | 0.6 | 5.6 | 0.6 | 2.9 | 0.6 | 5.7 |
| 0.65 | 7.4 | 0.65 | 5.5 | 0.65 | 2.9 | 0.65 | 5.7 |
| 0.7 | 7.4 | 0.7 | 5.4 | 0.7 | 2.9 | 0.7 | 5.6 |
| 0.75 | 7.2 | 0.75 | 5.1 | 0.75 | 2.9 | 0.75 | 5.4 |
| 0.8 | 6.9 | 0.8 | 4.8 | 0.8 | 2.7 | 0.8 | 5.1 |
| 0.85 | 6.3 | 0.85 | 4.3 | 0.85 | 2.5 | 0.85 | 4.7 |
| 0.9 | 5.3 | 0.9 | 3.6 | 0.9 | 2.2 | 0.9 | 3.9 |
| 0.95 | 3.7 | 0.95 | 2.6 | 0.95 | 1.8 | 0.95 | 2.8 |
| 1 | 1.2 | 1 | 1.2 | 1 | 1.2 | 1 | 1.2 |

HF-HFO-1234yf-HFO-1234zeZ-HCFO-1233zdE

| Organics 0.9 F1234yf + 0.05 F1234zeZ + 0.05 F1233zdE | | Organics 0.05 F1234yf + 0.9 F1234zeZ + 0.05 F1233zdE | | Organics 0.05 F1234yf + 0.05 F1234zeZ + 0.9 F1233zdE | | Organics 0.4 F1234yf + 0.3 F1234zeZ + 0.3 F1233zdE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.3 | 0 | 2.0 | 0 | 1.7 | 0 | 3.8 |
| 0.05 | 7.3 | 0.05 | 3.2 | 0.05 | 2.8 | 0.05 | 4.8 |

-continued

| | | | | | | | |
|---|---|---|---|---|---|---|---|
| 0.1 | 7.3 | 0.1 | 3.2 | 0.1 | 2.8 | 0.1 | 4.8 |
| 0.15 | 7.3 | 0.15 | 3.2 | 0.15 | 2.8 | 0.15 | 4.8 |
| 0.2 | 7.3 | 0.2 | 3.2 | 0.2 | 2.8 | 0.2 | 4.8 |
| 0.25 | 7.3 | 0.25 | 3.2 | 0.25 | 2.8 | 0.25 | 4.8 |
| 0.3 | 7.3 | 0.3 | 3.2 | 0.3 | 2.8 | 0.3 | 4.8 |
| 0.35 | 7.3 | 0.35 | 3.1 | 0.35 | 2.8 | 0.35 | 4.8 |
| 0.4 | 7.3 | 0.4 | 3.1 | 0.4 | 2.8 | 0.4 | 4.8 |
| 0.45 | 7.3 | 0.45 | 3.1 | 0.45 | 2.8 | 0.45 | 4.8 |
| 0.5 | 7.3 | 0.5 | 3.1 | 0.5 | 2.8 | 0.5 | 4.8 |
| 0.55 | 7.3 | 0.55 | 3.1 | 0.55 | 2.8 | 0.55 | 4.8 |
| 0.6 | 7.3 | 0.6 | 3.1 | 0.6 | 2.8 | 0.6 | 4.8 |
| 0.65 | 7.3 | 0.65 | 3.1 | 0.65 | 2.8 | 0.65 | 4.8 |
| 0.7 | 7.3 | 0.7 | 3.1 | 0.7 | 2.7 | 0.7 | 4.8 |
| 0.75 | 7.1 | 0.75 | 3.1 | 0.75 | 2.7 | 0.75 | 4.7 |
| 0.8 | 6.8 | 0.8 | 3.0 | 0.8 | 2.6 | 0.8 | 4.5 |
| 0.85 | 6.2 | 0.85 | 2.8 | 0.85 | 2.4 | 0.85 | 4.1 |
| 0.9 | 5.3 | 0.9 | 2.4 | 0.9 | 2.2 | 0.9 | 3.5 |
| 0.95 | 3.7 | 0.95 | 1.9 | 0.95 | 1.7 | 0.95 | 2.6 |
| 1 | 1.2 | 1 | 1.2 | 1 | 1.2 | 1 | 1.2 |

HF-HFO-1234yf-HCFO-1233zdE-HFO-1243zf

| Organics 0.9 F1234yf + 0.05 F1233zdE + 0.05 F1243zf | | Organics 0.05 F1234yf + 0.9 F1233zdE + 0.05 F1243zf | | Organics 0.05 F1234yf + 0.05 F1233zdE + 0.9 F1243zf | | Organics 0.4 F1234yf + 0.3 F1233zdE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.9 | 0 | 5.7 | 0 | 5.0 |
| 0.05 | 7.5 | 0.05 | 3.0 | 0.05 | 6.7 | 0.05 | 6.0 |
| 0.1 | 7.5 | 0.1 | 3.0 | 0.1 | 6.7 | 0.1 | 6.0 |
| 0.15 | 7.5 | 0.15 | 3.0 | 0.15 | 6.7 | 0.15 | 6.0 |
| 0.2 | 7.4 | 0.2 | 3.0 | 0.2 | 6.7 | 0.2 | 6.0 |
| 0.25 | 7.4 | 0.25 | 3.0 | 0.25 | 6.7 | 0.25 | 6.0 |
| 0.3 | 7.5 | 0.3 | 3.0 | 0.3 | 6.7 | 0.3 | 6.0 |
| 0.35 | 7.5 | 0.35 | 3.0 | 0.35 | 6.7 | 0.35 | 6.0 |
| 0.4 | 7.5 | 0.4 | 3.0 | 0.4 | 6.7 | 0.4 | 6.0 |
| 0.45 | 7.5 | 0.45 | 3.0 | 0.45 | 6.7 | 0.45 | 6.0 |
| 0.5 | 7.5 | 0.5 | 3.0 | 0.5 | 6.6 | 0.5 | 6.0 |
| 0.55 | 7.5 | 0.55 | 3.0 | 0.55 | 6.6 | 0.55 | 6.0 |
| 0.6 | 7.5 | 0.6 | 3.0 | 0.6 | 6.6 | 0.6 | 6.0 |
| 0.65 | 7.5 | 0.65 | 3.0 | 0.65 | 6.6 | 0.65 | 6.0 |
| 0.7 | 7.4 | 0.7 | 3.0 | 0.7 | 6.5 | 0.7 | 6.0 |
| 0.75 | 7.3 | 0.75 | 3.0 | 0.75 | 6.3 | 0.75 | 5.8 |
| 0.8 | 7.0 | 0.8 | 2.8 | 0.8 | 6.0 | 0.8 | 5.5 |
| 0.85 | 6.4 | 0.85 | 2.6 | 0.85 | 5.5 | 0.85 | 5.1 |
| 0.9 | 5.4 | 0.9 | 2.3 | 0.9 | 4.7 | 0.9 | 4.3 |
| 0.95 | 3.7 | 0.95 | 1.8 | 0.95 | 3.3 | 0.95 | 3.1 |
| 1 | 1.2 | 1 | 1.2 | 1 | 1.2 | 1 | 1.2 |

Example 8: Temperature and Pressure Range of Quaternary Mixtures

| Quaternary | Boiling point range | |
|---|---|---|
| | Temperature ° C. | Pressure bar abs |
| HF-HCFO-1233xf-HFC-245cb-HCFO-1233zdE | 0 to 40 | ~1.0 to ~8.7 |
| HF-HCFO-1233xf-HCFO-1233zdE-HFO-1234zeE | 0 to 40 | ~1.0 to ~8.6 |
| HF-HCFO-1233xf-HCFO-1233zdE-HFO-1234zeZ | 0 to 40 | ~0.9 to ~4.8 |
| HF-HCFO-1233xf-HCFO-1233zdE-HFO-1243zf | 0 to 40 | ~1.0 to ~9.9 |
| HF-HFC-245cb-HCFO-1233zdE-HFO-1234zeE | 0 to 40 | ~1.0 to ~8.9 |
| HF-HFC-245cb-HCFO-1233zdE-HFO-1234zeZ | 0 to 40 | ~1.0 to ~8.9 |
| HF-HFC-245cb-HCFO-1233zdE-HFO-1243zf | 0 to 40 | ~1.1 to ~10.1 |
| HF-HCFO-1233zdE-HFO-1234zeE-HFO-1234zeZ | 0 to 40 | ~1.0 to ~8.6 |
| HF-HCFO-1233zdE-HFO-1234zeE-HFO-1243zf | 0 to 40 | ~1.1 to ~10.1 |
| HF-HCFO-1233zdE-HFO-1234zeZ-HFO-1243zf | 0 to 40 | ~1.0 to ~9.9 |
| HF-HFO-1234yf-HFC-245cb-HCFO-1233zdE | 0 to 40 | ~1.1 to ~11.3 |
| HF-HCFO-1233xf-HFO-1234yf-HCFO-1233zdE | 0 to 40 | ~1.0 to ~11.1 |
| HF-HFO-1234yf-HFO-1234zeE-HCFO-1233zdE | 0 to 40 | ~1.1 to ~11.3 |
| HF-HFO-1234yf-HFO-1234zeZ-HCFO-1233zdE | 0 to 40 | ~1.0 to ~11.0 |
| HF-HFO-1234yf-HCFO-1233zdE-HFO-1243zf | 0 to 40 | ~1.2 to ~11.3 |

Example 9: Decantation Range of Quaternary Mixtures

| Quaternary | Decantation ranges Mass percentage of HF | | |
|---|---|---|---|
| | Isotherm 0° C. | Isotherm 25° C. | Isotherm 40° C. |
| HF-HCFO-1233xf-HFC-245cb-HCFO-1233zdE | 5-80 | 5-75 | 5-70 |
| HF-HCFO-1233xf-HCFO-1233zdE-HFO-1234zeE | 5-75 | 5-65 | 5-55 |
| HF-HCFO-1233xf-HCFO-1233zdE-HFO-1234zeZ | 5-80 | 5-75 | 5-65 |
| HF-HCFO-1233xf-HCFO-1233zdE-HFO-1243zf | 5-75 | 5-70 | 10-60 |
| HF-HFC-245cb-HCFO-1233zdE-HFO-1234zeE | 5-75 | 5-70 | 10-65 |
| HF-HFC-245cb-HCFO-1233zdE-HFO-1234zeZ | 5-80 | 5-75 | 5-70 |
| HF-HFC-245cb-HCFO-1233zdE-HFO-1243zf | 5-75 | 5-70 | 15-65 |
| HF-HCFO-1233zdE-HFO-1234zeE-HFO-1234zeZ | 5-75 | 5-65 | 10-55 |
| HF-HCFO-1233zdE-HFO-1234zeE-HFO-1243zf | 5-70 | 10-60 | * |
| HF-HCFO-1233zdE-HFO-1234zeZ-HFO-1243zf | 5-75 | 5-70 | 10-55 |
| HF-HFO-1234yf-HFC-245cb-HCFO-1233zdE | 5-75 | 5-75 | 15-70 |
| HF-HCFO-1233xf-HFO-1234yf-HCFO-1233zdE | 5-75 | 5-70 | 10-60 |
| HF-HFO-1234yf-HFO-1234zeE-HCFO-1233zdE | 5-70 | 10-60 | * |
| HF-HFO-1234yf-HFO-1234zeZ-HCFO-1233zdE | 5-75 | 5-70 | 10-60 |
| HF-HFO-1234yf-HCFO-1233zdE-HFO-1243zf | 5-75 | 10-65 | * |

Example 10: Penternary Mixtures, Isotherm at 25° C.

| HF-HCFO-1233xf-HFC-245cb-HCFO-1233zdE-HFO-1234zeE | | | | | | | | | |
|---|---|---|---|---|---|---|---|---|---|
| Organics 0.9 F1233xf + 0.033 F1233zdE + 0.033 F245cb + 0.034 F1234zeE | | Organics 0.033 F1233xf + 0.9 F1233zdE + 0.033 F245cb + 0.034 F1234zeE | | Organics 0.033 F1233xf + 0.033 F1233zdE + 0.9 245cb + 0.034 F1234zeE | | Organics 0.034 F1233xf + 0.033 F1233zdE + 0.033 F245cb + 0.9 F1234zeE | | Organics 0.25 F1233xf + 0.25 F1233zdE + 0.25 F245cb + 0.25 F1234zeE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 4.4 | 0 | 4.7 | 0 | 3.2 |
| 0.05 | 2.9 | 0.05 | 2.7 | 0.05 | 5.6 | 0.05 | 5.6 | 0.05 | 4.3 |
| 0.1 | 2.9 | 0.1 | 2.7 | 0.1 | 5.6 | 0.1 | 5.6 | 0.1 | 4.3 |
| 0.15 | 2.9 | 0.15 | 2.7 | 0.15 | 5.6 | 0.15 | 5.6 | 0.15 | 4.3 |
| 0.2 | 2.9 | 0.2 | 2.7 | 0.2 | 5.6 | 0.2 | 5.6 | 0.2 | 4.3 |
| 0.25 | 2.9 | 0.25 | 2.7 | 0.25 | 5.6 | 0.25 | 5.6 | 0.25 | 4.3 |
| 0.3 | 2.9 | 0.3 | 2.7 | 0.3 | 5.6 | 0.3 | 5.6 | 0.3 | 4.3 |
| 0.35 | 2.9 | 0.35 | 2.7 | 0.35 | 5.6 | 0.35 | 5.6 | 0.35 | 4.3 |
| 0.4 | 2.9 | 0.4 | 2.7 | 0.4 | 5.6 | 0.4 | 5.6 | 0.4 | 4.3 |
| 0.45 | 2.9 | 0.45 | 2.7 | 0.45 | 5.6 | 0.45 | 5.6 | 0.45 | 4.3 |
| 0.5 | 2.9 | 0.5 | 2.7 | 0.5 | 5.6 | 0.5 | 5.6 | 0.5 | 4.3 |
| 0.55 | 2.9 | 0.55 | 2.7 | 0.55 | 5.6 | 0.55 | 5.6 | 0.55 | 4.3 |
| 0.6 | 2.9 | 0.6 | 2.7 | 0.6 | 5.6 | 0.6 | 5.5 | 0.6 | 4.3 |
| 0.65 | 2.9 | 0.65 | 2.7 | 0.65 | 5.6 | 0.65 | 5.4 | 0.65 | 4.3 |
| 0.7 | 2.9 | 0.7 | 2.7 | 0.7 | 5.7 | 0.7 | 5.2 | 0.7 | 4.3 |
| 0.75 | 2.9 | 0.75 | 2.7 | 0.75 | 5.7 | 0.75 | 5.0 | 0.75 | 4.2 |
| 0.8 | 2.7 | 0.8 | 2.6 | 0.8 | 5.7 | 0.8 | 4.7 | 0.8 | 4.0 |
| 0.85 | 2.5 | 0.85 | 2.4 | 0.85 | 5.6 | 0.85 | 4.2 | 0.85 | 3.7 |
| 0.9 | 2.2 | 0.9 | 2.1 | 0.9 | 4.8 | 0.9 | 3.5 | 0.9 | 3.2 |
| 0.95 | 1.8 | 0.95 | 1.7 | 0.95 | 3.4 | 0.95 | 2.5 | 0.95 | 2.4 |
| 1 | 1.2 | 1 | 1.2 | 1 | 1.2 | 1 | 1.2 | 1 | 1.2 |

| HF-HCFO-1233xf-HFC-245cb-HCFO-1233zdE-HFO-1234zeZ | | | | | | | | | |
|---|---|---|---|---|---|---|---|---|---|
| Organics 0.9 F1233xf + 0.033 F1233zdE + 0.033 F245cb + 0.034 F1234zeZ | | Organics 0.033 F1233xf + 0.9 F1233zdE + 0.033 F245cb + 0.034 F1234zeZ | | Organics 0.033 F1233xf + 0.033 F1233zdE + 0.9 F245cb + 0.034 F1234zeZ | | Organics 0.034 F1233xf + 0.033 F1233zdE + 0.033 F245cb + 0.9 F1234zeZ | | Organics 0.25 F1233xf + 0.25 F1233zdE + 0.25 F245cb + 0.25 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.3 | 0 | 1.9 | 0 | 2.3 |
| 0.05 | 2.8 | 0.05 | 2.6 | 0.05 | 5.5 | 0.05 | 3.0 | 0.05 | 3.5 |
| 0.1 | 2.8 | 0.1 | 2.6 | 0.1 | 5.5 | 0.1 | 3.0 | 0.1 | 3.5 |
| 0.15 | 2.8 | 0.15 | 2.6 | 0.15 | 5.5 | 0.15 | 3.0 | 0.15 | 3.5 |
| 0.2 | 2.8 | 0.2 | 2.6 | 0.2 | 5.5 | 0.2 | 3.0 | 0.2 | 3.5 |

| MASSFRAC | PRESSURE bar | MASSFRAC | PRESSURE bar | MASSFRAC | PRESSURE bar | MASSFRAC | PRESSURE bar | MASSFRAC | PRESSURE bar |
|---|---|---|---|---|---|---|---|---|---|
| 0.25 | 2.8 | 0.25 | 2.6 | 0.25 | 5.5 | 0.25 | 3.0 | 0.25 | 3.5 |
| 0.3 | 2.8 | 0.3 | 2.6 | 0.3 | 5.5 | 0.3 | 3.0 | 0.3 | 3.5 |
| 0.35 | 2.8 | 0.35 | 2.6 | 0.35 | 5.5 | 0.35 | 3.0 | 0.35 | 3.5 |
| 0.4 | 2.8 | 0.4 | 2.6 | 0.4 | 5.5 | 0.4 | 3.0 | 0.4 | 3.5 |
| 0.45 | 2.8 | 0.45 | 2.6 | 0.45 | 5.5 | 0.45 | 3.0 | 0.45 | 3.5 |
| 0.5 | 2.8 | 0.5 | 2.6 | 0.5 | 5.5 | 0.5 | 3.0 | 0.5 | 3.5 |
| 0.55 | 2.8 | 0.55 | 2.6 | 0.55 | 5.5 | 0.55 | 3.0 | 0.55 | 3.5 |
| 0.6 | 2.8 | 0.6 | 2.6 | 0.6 | 5.5 | 0.6 | 3.0 | 0.6 | 3.5 |
| 0.65 | 2.8 | 0.65 | 2.6 | 0.65 | 5.5 | 0.65 | 3.0 | 0.65 | 3.6 |
| 0.7 | 2.8 | 0.7 | 2.6 | 0.7 | 5.6 | 0.7 | 3.0 | 0.7 | 3.6 |
| 0.75 | 2.8 | 0.75 | 2.6 | 0.75 | 5.6 | 0.75 | 3.0 | 0.75 | 3.6 |
| 0.8 | 2.7 | 0.8 | 2.5 | 0.8 | 5.6 | 0.8 | 2.9 | 0.8 | 3.5 |
| 0.85 | 2.5 | 0.85 | 2.3 | 0.85 | 5.5 | 0.85 | 2.7 | 0.85 | 3.3 |
| 0.9 | 2.2 | 0.9 | 2.1 | 0.9 | 4.8 | 0.9 | 2.4 | 0.9 | 2.8 |
| 0.95 | 1.8 | 0.95 | 1.7 | 0.95 | 3.4 | 0.95 | 1.9 | 0.95 | 2.2 |
| 1 | 1.2 | 1 | 1.2 | 1 | 1.2 | 1 | 1.2 | 1 | 1.2 |

HF-HCFO-1233xf-HFC-245cb-HCFO-1233zdE-HFO-1243zf

| Organics 0.9 F1233xf + 0.033 F1233zdE + 0.033 F245cb + 0.034 F1243zf | | Organics 0.033 F1233xf + 0.9 F1233zdE + 0.033 F245cb + 0.034 F1243zf | | Organics 0.033 F1233xf + 0.033 F1233zdE + 0.9 F245cb + 0.034 F1243zf | | Organics 0.034 F1233xf + 0.033 F1233zdE + 0.033 F245cb + 0.9 F1243zf | | Organics 0.25 F1233xf + 0.25 F1233zdE + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 4.5 | 0 | 5.6 | 0 | 3.5 |
| 0.05 | 3.0 | 0.05 | 2.8 | 0.05 | 5.7 | 0.05 | 6.5 | 0.05 | 4.6 |
| 0.1 | 3.0 | 0.1 | 2.8 | 0.1 | 5.7 | 0.1 | 6.6 | 0.1 | 4.6 |
| 0.15 | 3.0 | 0.15 | 2.8 | 0.15 | 5.7 | 0.15 | 6.6 | 0.15 | 4.6 |
| 0.2 | 3.0 | 0.2 | 2.8 | 0.2 | 5.7 | 0.2 | 6.5 | 0.2 | 4.6 |
| 0.25 | 3.0 | 0.25 | 2.8 | 0.25 | 5.7 | 0.25 | 6.5 | 0.25 | 4.6 |
| 0.3 | 3.0 | 0.3 | 2.8 | 0.3 | 5.7 | 0.3 | 6.5 | 0.3 | 4.6 |
| 0.35 | 2.9 | 0.35 | 2.8 | 0.35 | 5.7 | 0.35 | 6.5 | 0.35 | 4.6 |
| 0.4 | 2.9 | 0.4 | 2.8 | 0.4 | 5.7 | 0.4 | 6.5 | 0.4 | 4.6 |
| 0.45 | 2.9 | 0.45 | 2.7 | 0.45 | 5.7 | 0.45 | 6.5 | 0.45 | 4.6 |
| 0.5 | 2.9 | 0.5 | 2.7 | 0.5 | 5.7 | 0.5 | 6.5 | 0.5 | 4.6 |
| 0.55 | 2.9 | 0.55 | 2.7 | 0.55 | 5.7 | 0.55 | 6.5 | 0.55 | 4.6 |
| 0.6 | 2.9 | 0.6 | 2.7 | 0.6 | 5.7 | 0.6 | 6.5 | 0.6 | 4.6 |
| 0.65 | 2.9 | 0.65 | 2.7 | 0.65 | 5.7 | 0.65 | 6.4 | 0.65 | 4.6 |
| 0.7 | 2.9 | 0.7 | 2.7 | 0.7 | 5.7 | 0.7 | 6.4 | 0.7 | 4.7 |
| 0.75 | 2.9 | 0.75 | 2.7 | 0.75 | 5.7 | 0.75 | 6.2 | 0.75 | 4.6 |
| 0.8 | 2.8 | 0.8 | 2.6 | 0.8 | 5.7 | 0.8 | 5.9 | 0.8 | 4.4 |
| 0.85 | 2.6 | 0.85 | 2.4 | 0.85 | 5.6 | 0.85 | 5.4 | 0.85 | 4.1 |
| 0.9 | 2.3 | 0.9 | 2.2 | 0.9 | 4.8 | 0.9 | 4.6 | 0.9 | 3.5 |
| 0.95 | 1.8 | 0.95 | 1.8 | 0.95 | 3.4 | 0.95 | 3.3 | 0.95 | 2.6 |
| 1 | 1.2 | 1 | 1.2 | 1 | 1.2 | 1 | 1.2 | 1 | 1.2 |

HF-HCFO-1233xf-HCFO-1233zdE-HFO-1234zeE-HFO-1234zeZ

| Organics 0.9 F1233xf + 0.033 F1234zeE + 0.033 F1233zdE + 0.034 F1234zeZ | | Organics 0.033 F1233xf + 0.9 F1234zeE + 0.033 F1233zdE + 0.034 F1234zeZ | | Organics 0.033 F1233xf + 0.033 F1234zeE + 0.9 F1233zdE + 0.034 F1234zeZ | | Organics 0.034 F1233xf + 0.033 F1234zeE + 0.033 F1233zdE + 0.9 F1234zeZ | | Organics 0.25 F1233xf + 0.25 F1234zeE + 0.25 F1233zdE 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.6 | 0 | 1.5 | 0 | 1.9 | 0 | 2.4 |
| 0.05 | 2.8 | 0.05 | 5.5 | 0.05 | 2.6 | 0.05 | 3.0 | 0.05 | 3.5 |
| 0.1 | 2.8 | 0.1 | 5.5 | 0.1 | 2.6 | 0.1 | 3.0 | 0.1 | 3.5 |
| 0.15 | 2.8 | 0.15 | 5.5 | 0.15 | 2.6 | 0.15 | 3.0 | 0.15 | 3.5 |
| 0.2 | 2.8 | 0.2 | 5.5 | 0.2 | 2.6 | 0.2 | 3.0 | 0.2 | 3.5 |
| 0.25 | 2.8 | 0.25 | 5.5 | 0.25 | 2.6 | 0.25 | 3.0 | 0.25 | 3.5 |
| 0.3 | 2.8 | 0.3 | 5.5 | 0.3 | 2.6 | 0.3 | 3.0 | 0.3 | 3.5 |
| 0.35 | 2.8 | 0.35 | 5.5 | 0.35 | 2.6 | 0.35 | 3.0 | 0.35 | 3.5 |
| 0.4 | 2.8 | 0.4 | 5.5 | 0.4 | 2.6 | 0.4 | 3.0 | 0.4 | 3.5 |
| 0.45 | 2.8 | 0.45 | 5.5 | 0.45 | 2.6 | 0.45 | 3.0 | 0.45 | 3.5 |
| 0.5 | 2.8 | 0.5 | 5.5 | 0.5 | 2.6 | 0.5 | 3.0 | 0.5 | 3.5 |
| 0.55 | 2.8 | 0.55 | 5.4 | 0.55 | 2.6 | 0.55 | 3.0 | 0.55 | 3.4 |
| 0.6 | 2.8 | 0.6 | 5.4 | 0.6 | 2.6 | 0.6 | 3.0 | 0.6 | 3.4 |
| 0.65 | 2.8 | 0.65 | 5.3 | 0.65 | 2.6 | 0.65 | 3.0 | 0.65 | 3.4 |
| 0.7 | 2.8 | 0.7 | 5.1 | 0.7 | 2.5 | 0.7 | 3.0 | 0.7 | 3.4 |
| 0.75 | 2.7 | 0.75 | 4.9 | 0.75 | 2.5 | 0.75 | 3.0 | 0.75 | 3.3 |

-continued

| | | | | | | | | | |
|---|---|---|---|---|---|---|---|---|---|
| 0.8 | 2.6 | 0.8 | 4.6 | 0.8 | 2.4 | 0.8 | 2.8 | 0.8 | 3.1 |
| 0.85 | 2.4 | 0.85 | 4.1 | 0.85 | 2.3 | 0.85 | 2.6 | 0.85 | 2.9 |
| 0.9 | 2.1 | 0.9 | 3.4 | 0.9 | 2.0 | 0.9 | 2.3 | 0.9 | 2.5 |
| 0.95 | 1.7 | 0.95 | 2.5 | 0.95 | 1.7 | 0.95 | 1.9 | 0.95 | 1.9 |
| 1 | 1.2 | 1 | 1.2 | 1 | 1.2 | 1 | 1.2 | 1 | 1.2 |

HF-HCFO-1233xf-HCFO-1233zdE-HFO-1234zeE-HFO-1243zf

| Organics 0.9 F1233xf + 0.033 F1234zeE + 0.033 F1233zdE + 0.034 F1243zf | | Organics 0.033 F1233xf + 0.9 F1234zeE + 0.033 F1233zdE + 0.034 F1243zf | | Organics 0.033 F1233xf + 0.033 F1234zeE + 0.9 F1233zdE + 0.034 F1243zf | | Organics 0.034 F1233xf + 0.033 F1234zeE + 0.033 F1233zdE + 0.9 F1243zf | | Organics 0.25 F1233xf + 0.25 1234zeE + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 5.6 | 0 | 3.6 |
| 0.05 | 3.0 | 0.05 | 5.7 | 0.05 | 2.8 | 0.05 | 6.5 | 0.05 | 4.7 |
| 0.1 | 3.0 | 0.1 | 5.7 | 0.1 | 2.8 | 0.1 | 6.6 | 0.1 | 4.7 |
| 0.15 | 3.0 | 0.15 | 5.7 | 0.15 | 2.8 | 0.15 | 6.6 | 0.15 | 4.7 |
| 0.2 | 3.0 | 0.2 | 5.7 | 0.2 | 2.8 | 0.2 | 6.5 | 0.2 | 4.7 |
| 0.25 | 3.0 | 0.25 | 5.7 | 0.25 | 2.8 | 0.25 | 6.5 | 0.25 | 4.6 |
| 0.3 | 2.9 | 0.3 | 5.7 | 0.3 | 2.7 | 0.3 | 6.5 | 0.3 | 4.6 |
| 0.35 | 2.9 | 0.35 | 5.7 | 0.35 | 2.7 | 0.35 | 6.5 | 0.35 | 4.6 |
| 0.4 | 2.9 | 0.4 | 5.7 | 0.4 | 2.7 | 0.4 | 6.5 | 0.4 | 4.6 |
| 0.45 | 2.9 | 0.45 | 5.7 | 0.45 | 2.7 | 0.45 | 6.5 | 0.45 | 4.6 |
| 0.5 | 2.9 | 0.5 | 5.6 | 0.5 | 2.7 | 0.5 | 6.5 | 0.5 | 4.6 |
| 0.55 | 2.9 | 0.55 | 5.6 | 0.55 | 2.7 | 0.55 | 6.5 | 0.55 | 4.6 |
| 0.6 | 2.9 | 0.6 | 5.5 | 0.6 | 2.7 | 0.6 | 6.5 | 0.6 | 4.6 |
| 0.65 | 2.9 | 0.65 | 5.4 | 0.65 | 2.7 | 0.65 | 6.4 | 0.65 | 4.5 |
| 0.7 | 2.9 | 0.7 | 5.3 | 0.7 | 2.7 | 0.7 | 6.3 | 0.7 | 4.5 |
| 0.75 | 2.9 | 0.75 | 5.0 | 0.75 | 2.7 | 0.75 | 6.2 | 0.75 | 4.3 |
| 0.8 | 2.7 | 0.8 | 4.7 | 0.8 | 2.6 | 0.8 | 5.9 | 0.8 | 4.1 |
| 0.85 | 2.5 | 0.85 | 4.2 | 0.85 | 2.4 | 0.85 | 5.4 | 0.85 | 3.7 |
| 0.9 | 2.2 | 0.9 | 3.5 | 0.9 | 2.1 | 0.9 | 4.6 | 0.9 | 3.1 |
| 0.95 | 1.8 | 0.95 | 2.5 | 0.95 | 1.7 | 0.95 | 3.3 | 0.95 | 2.3 |
| 1 | 1.2 | 1 | 1.2 | 1 | 1.2 | 1 | 1.2 | 1 | 1.2 |

HF-HCFO-1233xf-HCFO-1233zdE-HFO-1234zeZ-HFO-1243zf

| Organics 0.9 F1233xf + 0.033 F1234zeZ + 0.033 F1233zdE + 0.034 F1243zf | | Organics 0.033 F1233xf + 0.9 F1234zeZ + 0.033 F1233zdE + 0.034 F1243zf | | Organics 0.033 F1233xf + 0.033 F1234zeZ + 0.9 F1233zdE + 0.034 F1243zf | | Organics 0.034 F1233xf + 0.033 F1234zeZ + 0.033 F1233zdE + 0.9 F1243zf | | Organics 0.25 F1233xf + 0.25 F1234zeZ + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.9 | 0 | 1.5 | 0 | 5.5 | 0 | 2.8 |
| 0.05 | 2.8 | 0.05 | 3.0 | 0.05 | 2.6 | 0.05 | 6.4 | 0.05 | 3.9 |
| 0.1 | 2.8 | 0.1 | 3.0 | 0.1 | 2.6 | 0.1 | 6.5 | 0.1 | 3.9 |
| 0.15 | 2.8 | 0.15 | 3.0 | 0.15 | 2.6 | 0.15 | 6.5 | 0.15 | 3.9 |
| 0.2 | 2.8 | 0.2 | 3.0 | 0.2 | 2.6 | 0.2 | 6.5 | 0.2 | 3.9 |
| 0.25 | 2.8 | 0.25 | 3.0 | 0.25 | 2.6 | 0.25 | 6.5 | 0.25 | 3.9 |
| 0.3 | 2.8 | 0.3 | 3.0 | 0.3 | 2.6 | 0.3 | 6.5 | 0.3 | 3.9 |
| 0.35 | 2.8 | 0.35 | 3.0 | 0.35 | 2.6 | 0.35 | 6.5 | 0.35 | 3.9 |
| 0.4 | 2.8 | 0.4 | 3.0 | 0.4 | 2.6 | 0.4 | 6.5 | 0.4 | 3.9 |
| 0.45 | 2.8 | 0.45 | 3.0 | 0.45 | 2.6 | 0.45 | 6.4 | 0.45 | 3.9 |
| 0.5 | 2.8 | 0.5 | 3.0 | 0.5 | 2.6 | 0.5 | 6.4 | 0.5 | 3.9 |
| 0.55 | 2.8 | 0.55 | 3.0 | 0.55 | 2.6 | 0.55 | 6.4 | 0.55 | 3.9 |
| 0.6 | 2.8 | 0.6 | 3.0 | 0.6 | 2.6 | 0.6 | 6.4 | 0.6 | 3.9 |
| 0.65 | 2.8 | 0.65 | 3.0 | 0.65 | 2.6 | 0.65 | 6.4 | 0.65 | 3.8 |
| 0.7 | 2.8 | 0.7 | 3.0 | 0.7 | 2.6 | 0.7 | 6.3 | 0.7 | 3.8 |
| 0.75 | 2.8 | 0.75 | 3.0 | 0.75 | 2.6 | 0.75 | 6.1 | 0.75 | 3.7 |
| 0.8 | 2.7 | 0.8 | 2.9 | 0.8 | 2.5 | 0.8 | 5.8 | 0.8 | 3.6 |
| 0.85 | 2.5 | 0.85 | 2.7 | 0.85 | 2.3 | 0.85 | 5.3 | 0.85 | 3.3 |
| 0.9 | 2.2 | 0.9 | 2.4 | 0.9 | 2.1 | 0.9 | 4.5 | 0.9 | 2.8 |
| 0.95 | 1.8 | 0.95 | 1.9 | 0.95 | 1.7 | 0.95 | 3.2 | 0.95 | 2.2 |
| 1 | 1.2 | 1 | 1.2 | 1 | 1.2 | 1 | 1.2 | 1 | 1.2 |

HF-HFC-245cb-HCFO-1233zdE-HFO-1234zeE-HFO-1234zeZ

| Organics 0.9 F245cb + 0.033 F1234zeE + 0.033 F1233zdE + 0.034 F1234zeZ | | Organics 0.033 F245cb + 0.9 F1234zeE + 0.033 F1233zdE + 0.034 F1234zeZ | | Organics 0.033 F245cb + 0.033 F1234zeE + 0.9 F1233zdE + 0.034 F1234zeZ | | Organics 0.034 F245cb + 0.033 F1234zeE + 0.033 F1233zdE + 0.9 F1234zeZ | | Organics 0.25 F245cb + 0.25 F1234zeE + 0.25 F1233zdE + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 4.7 | 0 | 1.6 | 0 | 2.0 | 0 | 3.2 |
| 0.05 | 5.6 | 0.05 | 5.6 | 0.05 | 2.7 | 0.05 | 3.1 | 0.05 | 4.3 |
| 0.1 | 5.6 | 0.1 | 5.6 | 0.1 | 2.7 | 0.1 | 3.1 | 0.1 | 4.3 |
| 0.15 | 5.6 | 0.15 | 5.6 | 0.15 | 2.7 | 0.15 | 3.1 | 0.15 | 4.3 |
| 0.2 | 5.6 | 0.2 | 5.6 | 0.2 | 2.7 | 0.2 | 3.1 | 0.2 | 4.3 |
| 0.25 | 5.6 | 0.25 | 5.6 | 0.25 | 2.7 | 0.25 | 3.1 | 0.25 | 4.3 |
| 0.3 | 5.6 | 0.3 | 5.6 | 0.3 | 2.7 | 0.3 | 3.1 | 0.3 | 4.3 |
| 0.35 | 5.6 | 0.35 | 5.6 | 0.35 | 2.7 | 0.35 | 3.1 | 0.35 | 4.3 |
| 0.4 | 5.6 | 0.4 | 5.6 | 0.4 | 2.7 | 0.4 | 3.1 | 0.4 | 4.3 |
| 0.45 | 5.6 | 0.45 | 5.6 | 0.45 | 2.7 | 0.45 | 3.1 | 0.45 | 4.3 |
| 0.5 | 5.6 | 0.5 | 5.6 | 0.5 | 2.7 | 0.5 | 3.1 | 0.5 | 4.3 |
| 0.55 | 5.6 | 0.55 | 5.6 | 0.55 | 2.7 | 0.55 | 3.1 | 0.55 | 4.3 |
| 0.6 | 5.6 | 0.6 | 5.5 | 0.6 | 2.7 | 0.6 | 3.1 | 0.6 | 4.3 |
| 0.65 | 5.6 | 0.65 | 5.4 | 0.65 | 2.7 | 0.65 | 3.1 | 0.65 | 4.3 |
| 0.7 | 5.7 | 0.7 | 5.2 | 0.7 | 2.7 | 0.7 | 3.1 | 0.7 | 4.3 |
| 0.75 | 5.7 | 0.75 | 5.0 | 0.75 | 2.7 | 0.75 | 3.1 | 0.75 | 4.3 |
| 0.8 | 5.7 | 0.8 | 4.7 | 0.8 | 2.6 | 0.8 | 3.0 | 0.8 | 4.1 |
| 0.85 | 5.6 | 0.85 | 4.2 | 0.85 | 2.4 | 0.85 | 2.7 | 0.85 | 3.7 |
| 0.9 | 4.8 | 0.9 | 3.5 | 0.9 | 2.1 | 0.9 | 2.4 | 0.9 | 3.2 |
| 0.95 | 3.4 | 0.95 | 2.5 | 0.95 | 1.7 | 0.95 | 1.9 | 0.95 | 2.4 |
| 1 | 1.2 | 1 | 1.2 | 1 | 1.2 | 1 | 1.2 | 1 | 1.2 |

HF-HFC-245cb-HCFO-1233zdE-HFO-1234zeE-HFO-1243zf

| Organics 0.9 F245cb + 0.033 F1234zeE + 0.033 F1233zdE + 0.034 F1243zf | | Organics 0.033 F245cb + 0.9 F1234zeE + 0.033 F1233zdE + 0.034 F1243zf | | Organics 0.033 F245cb + 0.033 F1234zeE + 0.9 F1233zdE + 0.034 F1243zf | | Organics 0.034 F245cb + 0.033 F1234zeE + 0.033 F1233zdE + 0.9 F1243zf | | Organics 0.25 F245cb + 0.25 F1234zeE + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 1.8 | 0 | 5.7 | 0 | 4.3 |
| 0.05 | 5.8 | 0.05 | 5.8 | 0.05 | 2.9 | 0.05 | 6.6 | 0.05 | 5.4 |
| 0.1 | 5.8 | 0.1 | 5.8 | 0.1 | 2.9 | 0.1 | 6.6 | 0.1 | 5.4 |
| 0.15 | 5.8 | 0.15 | 5.8 | 0.15 | 2.9 | 0.15 | 6.6 | 0.15 | 5.4 |
| 0.2 | 5.8 | 0.2 | 5.8 | 0.2 | 2.9 | 0.2 | 6.6 | 0.2 | 5.4 |
| 0.25 | 5.8 | 0.25 | 5.8 | 0.25 | 2.9 | 0.25 | 6.6 | 0.25 | 5.4 |
| 0.3 | 5.8 | 0.3 | 5.8 | 0.3 | 2.9 | 0.3 | 6.6 | 0.3 | 5.4 |
| 0.35 | 5.8 | 0.35 | 5.8 | 0.35 | 2.9 | 0.35 | 6.6 | 0.35 | 5.4 |
| 0.4 | 5.8 | 0.4 | 5.8 | 0.4 | 2.9 | 0.4 | 6.6 | 0.4 | 5.4 |
| 0.45 | 5.8 | 0.45 | 5.8 | 0.45 | 2.9 | 0.45 | 6.6 | 0.45 | 5.4 |
| 0.5 | 5.8 | 0.5 | 5.7 | 0.5 | 2.9 | 0.5 | 6.6 | 0.5 | 5.4 |
| 0.55 | 5.8 | 0.55 | 5.7 | 0.55 | 2.9 | 0.55 | 6.6 | 0.55 | 5.4 |
| 0.6 | 5.8 | 0.6 | 5.6 | 0.6 | 2.9 | 0.6 | 6.6 | 0.6 | 5.4 |
| 0.65 | 5.8 | 0.65 | 5.5 | 0.65 | 2.8 | 0.65 | 6.5 | 0.65 | 5.4 |
| 0.7 | 5.8 | 0.7 | 5.4 | 0.7 | 2.8 | 0.7 | 6.4 | 0.7 | 5.4 |
| 0.75 | 5.8 | 0.75 | 5.2 | 0.75 | 2.8 | 0.75 | 6.3 | 0.75 | 5.2 |
| 0.8 | 5.8 | 0.8 | 4.8 | 0.8 | 2.7 | 0.8 | 6.0 | 0.8 | 5.0 |
| 0.85 | 5.7 | 0.85 | 4.3 | 0.85 | 2.5 | 0.85 | 5.5 | 0.85 | 4.5 |
| 0.9 | 4.9 | 0.9 | 3.6 | 0.9 | 2.2 | 0.9 | 4.7 | 0.9 | 3.9 |
| 0.95 | 3.5 | 0.95 | 2.6 | 0.95 | 1.8 | 0.95 | 3.3 | 0.95 | 2.8 |
| 1 | 1.2 | 1 | 1.2 | 1 | 1.2 | 1 | 1.2 | 1 | 1.2 |

-continued

| HF-HFC-245cb-HCFO-1233zdE-HFO-1234zeZ-HFO-1243zf | | | | | | | | | |
|---|---|---|---|---|---|---|---|---|---|
| Organics 0.9 F245cb + 0.033 F1234zeZ + 0.033 F1233zdE + 0.034 F1243zf | | Organics 0.033 F245cb + 0.9 F1234zeZ + 0.033 F1233zdE + 0.034 F1243zf | | Organics 0.033 F245cb + 0.033 F1234zeZ + 0.9 F1233zdE + 0.034 F1243zf | | Organics 0.034 F245cb + 0.033 F1234zeZ + 0.033 F1233zdE + 0.9 F1243zf | | Organics 0.25 F245cb + 0.25 F1234zeZ + 0.25 F1233zdE + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 2.0 | 0 | 1.7 | 0 | 5.6 | 0 | 3.5 |
| 0.05 | 5.7 | 0.05 | 3.2 | 0.05 | 2.8 | 0.05 | 6.5 | 0.05 | 4.6 |
| 0.1 | 5.7 | 0.1 | 3.2 | 0.1 | 2.8 | 0.1 | 6.6 | 0.1 | 4.6 |
| 0.15 | 5.7 | 0.15 | 3.2 | 0.15 | 2.8 | 0.15 | 6.6 | 0.15 | 4.6 |
| 0.2 | 5.7 | 0.2 | 3.2 | 0.2 | 2.8 | 0.2 | 6.5 | 0.2 | 4.6 |
| 0.25 | 5.7 | 0.25 | 3.2 | 0.25 | 2.8 | 0.25 | 6.5 | 0.25 | 4.6 |
| 0.3 | 5.7 | 0.3 | 3.2 | 0.3 | 2.8 | 0.3 | 6.5 | 0.3 | 4.6 |
| 0.35 | 5.7 | 0.35 | 3.2 | 0.35 | 2.8 | 0.35 | 6.5 | 0.35 | 4.6 |
| 0.4 | 5.7 | 0.4 | 3.2 | 0.4 | 2.8 | 0.4 | 6.5 | 0.4 | 4.6 |
| 0.45 | 5.7 | 0.45 | 3.2 | 0.45 | 2.8 | 0.45 | 6.5 | 0.45 | 4.6 |
| 0.5 | 5.7 | 0.5 | 3.2 | 0.5 | 2.8 | 0.5 | 6.5 | 0.5 | 4.7 |
| 0.55 | 5.7 | 0.55 | 3.2 | 0.55 | 2.8 | 0.55 | 6.5 | 0.55 | 4.7 |
| 0.6 | 5.7 | 0.6 | 3.2 | 0.6 | 2.8 | 0.6 | 6.5 | 0.6 | 4.7 |
| 0.65 | 5.7 | 0.65 | 3.2 | 0.65 | 2.8 | 0.65 | 6.4 | 0.65 | 4.7 |
| 0.7 | 5.7 | 0.7 | 3.2 | 0.7 | 2.8 | 0.7 | 6.4 | 0.7 | 4.7 |
| 0.75 | 5.7 | 0.75 | 3.1 | 0.75 | 2.8 | 0.75 | 6.2 | 0.75 | 4.7 |
| 0.8 | 5.7 | 0.8 | 3.0 | 0.8 | 2.6 | 0.8 | 5.9 | 0.8 | 4.5 |
| 0.85 | 5.6 | 0.85 | 2.8 | 0.85 | 2.4 | 0.85 | 5.4 | 0.85 | 4.1 |
| 0.9 | 4.8 | 0.9 | 2.5 | 0.9 | 2.2 | 0.9 | 4.6 | 0.9 | 3.5 |
| 0.95 | 3.4 | 0.95 | 1.9 | 0.95 | 1.8 | 0.95 | 3.3 | 0.95 | 2.6 |
| 1 | 1.2 | 1 | 1.2 | 1 | 1.2 | 1 | 1.2 | 1 | 1.2 |

| HF-HCFO-1233zdE-HFO-1234zeE-HFO-1234zeZ-HFO-1243zf | | | | | | | | | |
|---|---|---|---|---|---|---|---|---|---|
| Organics 0.9 F1234zeE + 0.033 F1234zeZ + 0.033 F1233zdE + 0.034 F1243zf | | Organics 0.033 F1234zeE + 0.9 F1234zeZ + 0.033 F1233zdE + 0.034 F1243zf | | Organics 0.033 F1234zeE + 0.033 F1234zeZ + 0.9 F1233zdE + 0.034 F1243zf | | Organics 0.034 F1234zeE + 0.033 F1234zeZ + 0.033 F1233zdE + 0.9 F1243zf | | Organics 0.25 F1234zeE + 0.25 F1234zeZ + 0.25 F1233zdE + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.7 | 0 | 2.1 | 0 | 1.7 | 0 | 5.6 | 0 | 3.6 |
| 0.05 | 5.7 | 0.05 | 3.2 | 0.05 | 2.8 | 0.05 | 6.5 | 0.05 | 4.7 |
| 0.1 | 5.7 | 0.1 | 3.2 | 0.1 | 2.8 | 0.1 | 6.6 | 0.1 | 4.7 |
| 0.15 | 5.7 | 0.15 | 3.2 | 0.15 | 2.8 | 0.15 | 6.5 | 0.15 | 4.7 |
| 0.2 | 5.7 | 0.2 | 3.2 | 0.2 | 2.8 | 0.2 | 6.5 | 0.2 | 4.7 |
| 0.25 | 5.7 | 0.25 | 3.2 | 0.25 | 2.8 | 0.25 | 6.5 | 0.25 | 4.7 |
| 0.3 | 5.7 | 0.3 | 3.2 | 0.3 | 2.8 | 0.3 | 6.5 | 0.3 | 4.6 |
| 0.35 | 5.7 | 0.35 | 3.1 | 0.35 | 2.8 | 0.35 | 6.5 | 0.35 | 4.6 |
| 0.4 | 5.7 | 0.4 | 3.1 | 0.4 | 2.8 | 0.4 | 6.5 | 0.4 | 4.6 |
| 0.45 | 5.7 | 0.45 | 3.1 | 0.45 | 2.7 | 0.45 | 6.5 | 0.45 | 4.6 |
| 0.5 | 5.6 | 0.5 | 3.1 | 0.5 | 2.7 | 0.5 | 6.5 | 0.5 | 4.6 |
| 0.55 | 5.6 | 0.55 | 3.1 | 0.55 | 2.7 | 0.55 | 6.5 | 0.55 | 4.6 |
| 0.6 | 5.5 | 0.6 | 3.1 | 0.6 | 2.7 | 0.6 | 6.5 | 0.6 | 4.6 |
| 0.65 | 5.4 | 0.65 | 3.1 | 0.65 | 2.7 | 0.65 | 6.4 | 0.65 | 4.6 |
| 0.7 | 5.3 | 0.7 | 3.1 | 0.7 | 2.7 | 0.7 | 6.3 | 0.7 | 4.5 |
| 0.75 | 5.0 | 0.75 | 3.1 | 0.75 | 2.7 | 0.75 | 6.2 | 0.75 | 4.3 |
| 0.8 | 4.7 | 0.8 | 3.0 | 0.8 | 2.6 | 0.8 | 5.9 | 0.8 | 4.1 |
| 0.85 | 4.2 | 0.85 | 2.7 | 0.85 | 2.4 | 0.85 | 5.4 | 0.85 | 3.7 |
| 0.9 | 3.5 | 0.9 | 2.4 | 0.9 | 2.1 | 0.9 | 4.6 | 0.9 | 3.2 |
| 0.95 | 2.5 | 0.95 | 1.9 | 0.95 | 1.7 | 0.95 | 3.3 | 0.95 | 2.4 |
| 1 | 1.2 | 1 | 1.2 | 1 | 1.2 | 1 | 1.2 | 1 | 1.2 |

| HF-HCFO-1233xF-HFO-1234yf-HFO-1234zeE-HCFO-1233zdE ||||||||||
| --- | --- | --- | --- | --- | --- | --- | --- | --- | --- |
| Organics 0.9 F1233xf + 0.033 F1234zeE + 0.033 F1233zdE + 0.034 F1234yf || Organics 0.033 F1233xf + 0.9 F1234zeE + 0.033 F1233zdE + 0.034 F1234yf || Organics 0.033 F1233xf + 0.033 F1234zeE + 0.9 F1233zdE + 0.034 F1234yf || Organics 0.034 F1233xf + 0.033 F1234zeE + 0.033 F1233zdE + 0.9 F1234yf || Organics 0.25 F1233xf + 0.25 F1234zeE + 0.25 F1233zdE + 0.25 F1234yf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 6.4 | 0 | 3.8 |
| 0.05 | 3.0 | 0.05 | 5.7 | 0.05 | 2.8 | 0.05 | 7.4 | 0.05 | 4.8 |
| 0.1 | 3.0 | 0.1 | 5.7 | 0.1 | 2.8 | 0.1 | 7.4 | 0.1 | 4.8 |
| 0.15 | 3.0 | 0.15 | 5.7 | 0.15 | 2.8 | 0.15 | 7.4 | 0.15 | 4.8 |
| 0.2 | 3.0 | 0.2 | 5.7 | 0.2 | 2.8 | 0.2 | 7.4 | 0.2 | 4.8 |
| 0.25 | 3.0 | 0.25 | 5.7 | 0.25 | 2.8 | 0.25 | 7.4 | 0.25 | 4.8 |
| 0.3 | 3.0 | 0.3 | 5.7 | 0.3 | 2.8 | 0.3 | 7.4 | 0.3 | 4.8 |
| 0.35 | 3.0 | 0.35 | 5.7 | 0.35 | 2.8 | 0.35 | 7.4 | 0.35 | 4.8 |
| 0.4 | 3.0 | 0.4 | 5.7 | 0.4 | 2.8 | 0.4 | 7.4 | 0.4 | 4.8 |
| 0.45 | 3.0 | 0.45 | 5.7 | 0.45 | 2.8 | 0.45 | 7.4 | 0.45 | 4.8 |
| 0.5 | 3.0 | 0.5 | 5.7 | 0.5 | 2.8 | 0.5 | 7.4 | 0.5 | 4.8 |
| 0.55 | 3.0 | 0.55 | 5.6 | 0.55 | 2.8 | 0.55 | 7.4 | 0.55 | 4.8 |
| 0.6 | 3.0 | 0.6 | 5.5 | 0.6 | 2.8 | 0.6 | 7.4 | 0.6 | 4.8 |
| 0.65 | 2.9 | 0.65 | 5.4 | 0.65 | 2.7 | 0.65 | 7.4 | 0.65 | 4.8 |
| 0.7 | 2.9 | 0.7 | 5.3 | 0.7 | 2.7 | 0.7 | 7.4 | 0.7 | 4.7 |
| 0.75 | 2.9 | 0.75 | 5.1 | 0.75 | 2.7 | 0.75 | 7.2 | 0.75 | 4.6 |
| 0.8 | 2.8 | 0.8 | 4.7 | 0.8 | 2.6 | 0.8 | 6.9 | 0.8 | 4.3 |
| 0.85 | 2.6 | 0.85 | 4.2 | 0.85 | 2.4 | 0.85 | 6.3 | 0.85 | 3.9 |
| 0.9 | 2.3 | 0.9 | 3.6 | 0.9 | 2.1 | 0.9 | 5.3 | 0.9 | 3.3 |
| 0.95 | 1.8 | 0.95 | 2.6 | 0.95 | 1.7 | 0.95 | 3.7 | 0.95 | 2.4 |
| 1 | 1.2 | 1 | 1.2 | 1 | 1.2 | 1 | 1.2 | 1 | 1.2 |

| HF-HCFO-1233xf-HFO-1234yf-HFO-1234zeZ-HCFO-1233zdE ||||||||||
| --- | --- | --- | --- | --- | --- | --- | --- | --- | --- |
| Organics 0.9 F1233xf + 0.033 F1234zeZ + 0.033 F1233zdE + 0.034 F1234yf || Organics 0.033 F1233xf + 0.9 F1234zeZ + 0.033 F1233zdE + 0.034 F1234zf || Organics 0.033 F1233xf + 0.033 F1234zeZ + 0.9 F1233zdE + 0.034 F1234yf || Organics 0.034 F1233xf + 0.033 F1234zeZ + 0.033 F1233zdE + 0.9 F1234yf || Organics 0.25 F1233xf + 0.25 F1234zeZ + 0.25 F1233zdE + 0.25 F1234yf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 2.0 | 0 | 1.6 | 0 | 6.3 | 0 | 3.0 |
| 0.05 | 2.9 | 0.05 | 3.1 | 0.05 | 2.7 | 0.05 | 7.3 | 0.05 | 4.1 |
| 0.1 | 2.9 | 0.1 | 3.1 | 0.1 | 2.7 | 0.1 | 7.3 | 0.1 | 4.1 |
| 0.15 | 2.9 | 0.15 | 3.1 | 0.15 | 2.7 | 0.15 | 7.3 | 0.15 | 4.1 |
| 0.2 | 2.9 | 0.2 | 3.1 | 0.2 | 2.7 | 0.2 | 7.3 | 0.2 | 4.1 |
| 0.25 | 2.9 | 0.25 | 3.1 | 0.25 | 2.7 | 0.25 | 7.3 | 0.25 | 4.1 |
| 0.3 | 2.9 | 0.3 | 3.1 | 0.3 | 2.7 | 0.3 | 7.3 | 0.3 | 4.1 |
| 0.35 | 2.9 | 0.35 | 3.1 | 0.35 | 2.7 | 0.35 | 7.3 | 0.35 | 4.1 |
| 0.4 | 2.9 | 0.4 | 3.1 | 0.4 | 2.7 | 0.4 | 7.3 | 0.4 | 4.1 |
| 0.45 | 2.9 | 0.45 | 3.1 | 0.45 | 2.7 | 0.45 | 7.3 | 0.45 | 4.1 |
| 0.5 | 2.9 | 0.5 | 3.1 | 0.5 | 2.7 | 0.5 | 7.3 | 0.5 | 4.1 |
| 0.55 | 2.9 | 0.55 | 3.1 | 0.55 | 2.7 | 0.55 | 7.3 | 0.55 | 4.1 |
| 0.6 | 2.9 | 0.6 | 3.1 | 0.6 | 2.7 | 0.6 | 7.3 | 0.6 | 4.1 |
| 0.65 | 2.9 | 0.65 | 3.1 | 0.65 | 2.7 | 0.65 | 7.3 | 0.65 | 4.1 |
| 0.7 | 2.9 | 0.7 | 3.1 | 0.7 | 2.7 | 0.7 | 7.3 | 0.7 | 4.0 |
| 0.75 | 2.8 | 0.75 | 3.1 | 0.75 | 2.6 | 0.75 | 7.1 | 0.75 | 4.0 |
| 0.8 | 2.7 | 0.8 | 2.9 | 0.8 | 2.5 | 0.8 | 6.8 | 0.8 | 3.8 |
| 0.85 | 2.5 | 0.85 | 2.7 | 0.85 | 2.4 | 0.85 | 6.2 | 0.85 | 3.5 |
| 0.9 | 2.2 | 0.9 | 2.4 | 0.9 | 2.1 | 0.9 | 5.3 | 0.9 | 3.0 |
| 0.95 | 1.8 | 0.95 | 1.9 | 0.95 | 1.7 | 0.95 | 3.7 | 0.95 | 2.3 |
| 1 | 1.2 | 1 | 1.2 | 1 | 1.2 | 1 | 1.2 | 1 | 1.2 |

HF-HCFO-1233xf-HFO-1234yf-HCFO-1233zdE-HFO-1243zf

| Organics 0.9 F1233xf + 0.033 F1243zf + 0.033 F1233zdE + 0.034 F1234yf | | Organics 0.033 F1233xf + 0.9 F1243zf + 0.033 F1233zdE + 0.034 F1234yf | | Organics 0.033 F1233xf + 0.033 F1243zf + 0.9 F1233zdE + 0.034 F1234yf | | Organics 0.034 F1233xf + 0.033 F1243zf + 0.033 F1233zdE + 0.9 F1234yf | | Organics 0.25 F1233xf + 0.25 F1243zf + 0.25 F1233zdE + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 5.6 | 0 | 1.7 | 0 | 6.4 | 0 | 4.1 |
| 0.05 | 3.0 | 0.05 | 6.6 | 0.05 | 2.8 | 0.05 | 7.4 | 0.05 | 5.2 |
| 0.1 | 3.0 | 0.1 | 6.6 | 0.1 | 2.8 | 0.1 | 7.4 | 0.1 | 5.2 |
| 0.15 | 3.0 | 0.15 | 6.6 | 0.15 | 2.8 | 0.15 | 7.4 | 0.15 | 5.2 |
| 0.2 | 3.0 | 0.2 | 6.6 | 0.2 | 2.8 | 0.2 | 7.4 | 0.2 | 5.2 |
| 0.25 | 3.0 | 0.25 | 6.6 | 0.25 | 2.8 | 0.25 | 7.4 | 0.25 | 5.2 |
| 0.3 | 3.0 | 0.3 | 6.6 | 0.3 | 2.8 | 0.3 | 7.4 | 0.3 | 5.2 |
| 0.35 | 3.0 | 0.35 | 6.6 | 0.35 | 2.8 | 0.35 | 7.4 | 0.35 | 5.2 |
| 0.4 | 3.0 | 0.4 | 6.6 | 0.4 | 2.8 | 0.4 | 7.4 | 0.4 | 5.2 |
| 0.45 | 3.0 | 0.45 | 6.6 | 0.45 | 2.8 | 0.45 | 7.4 | 0.45 | 5.2 |
| 0.5 | 3.0 | 0.5 | 6.6 | 0.5 | 2.8 | 0.5 | 7.4 | 0.5 | 5.1 |
| 0.55 | 3.0 | 0.55 | 6.6 | 0.55 | 2.8 | 0.55 | 7.4 | 0.55 | 5.1 |
| 0.6 | 3.0 | 0.6 | 6.5 | 0.6 | 2.8 | 0.6 | 7.4 | 0.6 | 5.1 |
| 0.65 | 3.0 | 0.65 | 6.5 | 0.65 | 2.8 | 0.65 | 7.4 | 0.65 | 5.1 |
| 0.7 | 3.0 | 0.7 | 6.4 | 0.7 | 2.8 | 0.7 | 7.4 | 0.7 | 5.1 |
| 0.75 | 3.0 | 0.75 | 6.2 | 0.75 | 2.8 | 0.75 | 7.2 | 0.75 | 4.9 |
| 0.8 | 2.8 | 0.8 | 6.0 | 0.8 | 2.7 | 0.8 | 6.9 | 0.8 | 4.7 |
| 0.85 | 2.6 | 0.85 | 5.5 | 0.85 | 2.5 | 0.85 | 6.3 | 0.85 | 4.3 |
| 0.9 | 2.3 | 0.9 | 4.6 | 0.9 | 2.2 | 0.9 | 5.3 | 0.9 | 3.7 |
| 0.95 | 1.8 | 0.95 | 3.3 | 0.95 | 1.8 | 0.95 | 3.7 | 0.95 | 2.7 |
| 1 | 1.2 | 1 | 1.2 | 1 | 1.2 | 1 | 1.2 | 1 | 1.2 |

HF-HFO-1234yf-HFO-1234zeE-HFO-1234zeZ-HCFO-1233zdE

| Organics 0.9 F1234yf + 0.033 F1233zdE + 0.033 F1234zeE + 0.034 F1234zeZ | | Organics 0.033 F1234yf + 0.9 F1233zdE + 0.033 F1234zeE + 0.034 F1234zeZ | | Organics 0.033 F1234yf + 0.033 F1233zdE + 0.9 F1234zeE + 0.034 F1234zeZ | | Organics 0.034 F1234yf + 0.033 F1233zdE + 0.033 F1234zeE + 0.9 F1234zeZ | | Organics 0.25 F1234yf + 0.25 F1233zdE + 0.25 F1234zeE + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 4.7 | 0 | 2.1 | 0 | 3.8 |
| 0.05 | 7.4 | 0.05 | 2.8 | 0.05 | 5.7 | 0.05 | 3.2 | 0.05 | 4.8 |
| 0.1 | 7.4 | 0.1 | 2.8 | 0.1 | 5.7 | 0.1 | 3.2 | 0.1 | 4.8 |
| 0.15 | 7.4 | 0.15 | 2.8 | 0.15 | 5.7 | 0.15 | 3.2 | 0.15 | 4.8 |
| 0.2 | 7.4 | 0.2 | 2.8 | 0.2 | 5.7 | 0.2 | 3.2 | 0.2 | 4.8 |
| 0.25 | 7.4 | 0.25 | 2.8 | 0.25 | 5.7 | 0.25 | 3.2 | 0.25 | 4.8 |
| 0.3 | 7.4 | 0.3 | 2.8 | 0.3 | 5.7 | 0.3 | 3.2 | 0.3 | 4.8 |
| 0.35 | 7.4 | 0.35 | 2.8 | 0.35 | 5.7 | 0.35 | 3.2 | 0.35 | 4.8 |
| 0.4 | 7.4 | 0.4 | 2.8 | 0.4 | 5.7 | 0.4 | 3.2 | 0.4 | 4.8 |
| 0.45 | 7.4 | 0.45 | 2.8 | 0.45 | 5.7 | 0.45 | 3.2 | 0.45 | 4.8 |
| 0.5 | 7.4 | 0.5 | 2.8 | 0.5 | 5.7 | 0.5 | 3.2 | 0.5 | 4.8 |
| 0.55 | 7.4 | 0.55 | 2.8 | 0.55 | 5.6 | 0.55 | 3.2 | 0.55 | 4.8 |
| 0.6 | 7.4 | 0.6 | 2.8 | 0.6 | 5.5 | 0.6 | 3.2 | 0.6 | 4.8 |
| 0.65 | 7.4 | 0.65 | 2.7 | 0.65 | 5.4 | 0.65 | 3.2 | 0.65 | 4.8 |
| 0.7 | 7.4 | 0.7 | 2.7 | 0.7 | 5.3 | 0.7 | 3.2 | 0.7 | 4.7 |
| 0.75 | 7.2 | 0.75 | 2.7 | 0.75 | 5.1 | 0.75 | 3.1 | 0.75 | 4.6 |
| 0.8 | 6.9 | 0.8 | 2.6 | 0.8 | 4.7 | 0.8 | 3.0 | 0.8 | 4.3 |
| 0.85 | 6.3 | 0.85 | 2.4 | 0.85 | 4.2 | 0.85 | 2.8 | 0.85 | 4.0 |
| 0.9 | 5.3 | 0.9 | 2.1 | 0.9 | 3.6 | 0.9 | 2.4 | 0.9 | 3.4 |
| 0.95 | 3.7 | 0.95 | 1.7 | 0.95 | 2.6 | 0.95 | 1.9 | 0.95 | 2.5 |
| 1 | 1.2 | 1 | 1.2 | 1 | 1.2 | 1 | 1.2 | 1 | 1.2 |

HF-HFO-1234yf-HFO-1234zeE-HCFO-1233zdE-HFO-1243zf

| Organics 0.9 F1234yf + 0.033 F1233zdE + 0.033 F1234zeE + 0.034 F1243zf | | Organics 0.033 F1234yf + 0.9 F1233zdE + 0.033 F1234zeE + 0.034 F1243zf | | Organics 0.033 F1234yf + 0.033 F1233zdE + 0.9 F1234zeE + 0.034 F1243zf | | Organics 0.034 F1234yf + 0.033 F1233zdE + 0.033 F1234zeE + 0.9 F1243zf | | Organics 0.25 F1234yf + 0.25 F1233zdE + 0.25 F1234zeE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.9 | 0 | 4.9 | 0 | 5.7 | 0 | 4.8 |
| 0.05 | 7.5 | 0.05 | 3.0 | 0.05 | 5.8 | 0.05 | 6.7 | 0.05 | 5.8 |
| 0.1 | 7.5 | 0.1 | 3.0 | 0.1 | 5.9 | 0.1 | 6.7 | 0.1 | 5.9 |
| 0.15 | 7.5 | 0.15 | 3.0 | 0.15 | 5.8 | 0.15 | 6.7 | 0.15 | 5.9 |
| 0.2 | 7.5 | 0.2 | 3.0 | 0.2 | 5.8 | 0.2 | 6.7 | 0.2 | 5.9 |
| 0.25 | 7.5 | 0.25 | 3.0 | 0.25 | 5.8 | 0.25 | 6.7 | 0.25 | 5.9 |
| 0.3 | 7.5 | 0.3 | 3.0 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.8 |
| 0.55 | 7.5 | 0.55 | 2.9 | 0.55 | 5.8 | 0.55 | 6.6 | 0.55 | 5.8 |
| 0.6 | 7.5 | 0.6 | 2.9 | 0.6 | 5.7 | 0.6 | 6.6 | 0.6 | 5.8 |
| 0.65 | 7.5 | 0.65 | 2.9 | 0.65 | 5.6 | 0.65 | 6.6 | 0.65 | 5.8 |
| 0.7 | 7.5 | 0.7 | 2.9 | 0.7 | 5.4 | 0.7 | 6.5 | 0.7 | 5.7 |
| 0.75 | 7.3 | 0.75 | 2.9 | 0.75 | 5.2 | 0.75 | 6.3 | 0.75 | 5.5 |
| 0.8 | 7.0 | 0.8 | 2.7 | 0.8 | 4.9 | 0.8 | 6.0 | 0.8 | 5.2 |
| 0.85 | 6.4 | 0.85 | 2.5 | 0.85 | 4.4 | 0.85 | 5.5 | 0.85 | 4.8 |
| 0.9 | 5.4 | 0.9 | 2.2 | 0.9 | 3.6 | 0.9 | 4.7 | 0.9 | 4.0 |
| 0.95 | 3.7 | 0.95 | 1.8 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

HF-HFO-1234yf-HFO-1234zeZ-HCFO-1233zdE-HFO-1243zf

| Organics 0.9 F1234yf + 0.033 F1233zdE + 0.033 F1234zeZ + 0.034 F1243zf | | Organics 0.033 F1234yf + 0.9 F1233zdE + 0.033 F1234zeZ + 0.034 F1243zf | | Organics 0.033 F1234yf + 0.033 F1233zdE + 0.9 F1234zeZ + 0.034 F1243zf | | Organics 0.034 F1234yf + 0.033 F1233zdE + 0.033 F1234zeZ + 0.9 F1243zf | | Organics 0.25 F1234yf + 0.25 F1233zdE + 0.25 F1234zeZ + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 2.1 | 0 | 5.6 | 0 | 4.1 |
| 0.05 | 7.4 | 0.05 | 2.9 | 0.05 | 3.2 | 0.05 | 6.6 | 0.05 | 5.2 |
| 0.1 | 7.4 | 0.1 | 2.9 | 0.1 | 3.2 | 0.1 | 6.6 | 0.1 | 5.2 |
| 0.15 | 7.4 | 0.15 | 2.9 | 0.15 | 3.2 | 0.15 | 6.6 | 0.15 | 5.2 |
| 0.2 | 7.4 | 0.2 | 2.9 | 0.2 | 3.2 | 0.2 | 6.6 | 0.2 | 5.2 |
| 0.25 | 7.4 | 0.25 | 2.8 | 0.25 | 3.2 | 0.25 | 6.6 | 0.25 | 5.2 |
| 0.3 | 7.4 | 0.3 | 2.8 | 0.3 | 3.2 | 0.3 | 6.6 | 0.3 | 5.2 |
| 0.35 | 7.4 | 0.35 | 2.8 | 0.35 | 3.2 | 0.35 | 6.6 | 0.35 | 5.1 |
| 0.4 | 7.4 | 0.4 | 2.8 | 0.4 | 3.2 | 0.4 | 6.6 | 0.4 | 5.1 |
| 0.45 | 7.4 | 0.45 | 2.8 | 0.45 | 3.2 | 0.45 | 6.6 | 0.45 | 5.1 |
| 0.5 | 7.4 | 0.5 | 2.8 | 0.5 | 3.2 | 0.5 | 6.6 | 0.5 | 5.1 |
| 0.55 | 7.4 | 0.55 | 2.8 | 0.55 | 3.2 | 0.55 | 6.6 | 0.55 | 5.1 |
| 0.6 | 7.4 | 0.6 | 2.8 | 0.6 | 3.2 | 0.6 | 6.5 | 0.6 | 5.1 |
| 0.65 | 7.4 | 0.65 | 2.8 | 0.65 | 3.2 | 0.65 | 6.5 | 0.65 | 5.1 |
| 0.7 | 7.4 | 0.7 | 2.8 | 0.7 | 3.2 | 0.7 | 6.4 | 0.7 | 5.1 |
| 0.75 | 7.2 | 0.75 | 2.8 | 0.75 | 3.2 | 0.75 | 6.2 | 0.75 | 5.0 |
| 0.8 | 6.9 | 0.8 | 2.7 | 0.8 | 3.0 | 0.8 | 5.9 | 0.8 | 4.7 |
| 0.85 | 6.3 | 0.85 | 2.5 | 0.85 | 2.8 | 0.85 | 5.5 | 0.85 | 4.3 |
| 0.9 | 5.3 | 0.9 | 2.2 | 0.9 | 2.5 | 0.9 | 4.6 | 0.9 | 3.7 |
| 0.95 | 3.7 | 0.95 | 1.8 | 0.95 | 2.0 | 0.95 | 3.3 | 0.95 | 2.7 |
| 1 | 1.2 | 1 | 1.2 | 1 | 1.2 | 1 | 1.2 | 1 | 1.2 |

HF-HFO-1234yf-HFC-245cb-HFO-1234zeE-HCFO-1233zdE

| Organics 0.9 F1234yf + 0.033 F1234zeE + 0.033 F245cb + 0.034 F1233zdE | | Organics 0.033 F1234yf + 0.9 F1234zeE + 0.033 F245cb + 0.034 F1233zdE | | Organics 0.033 F1234yf + 0.033 F1234zeE + 0.9 F245cb + 0.034 F1233zdE | | Organics 0.034 F1234yf + 0.033 F1234zeE + 0.033 F245cb + 0.9 F1233zdE | | Organics 0.25 F1234yf + 0.25 F1234zeE + 0.25 F245cb + 0.25 F1233zdE | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 4.8 | 0 | 4.6 | 0 | 1.8 | 0 | 4.5 |
| 0.05 | 7.5 | 0.05 | 5.8 | 0.05 | 5.8 | 0.05 | 2.9 | 0.05 | 5.6 |
| 0.1 | 7.5 | 0.1 | 5.8 | 0.1 | 5.8 | 0.1 | 2.9 | 0.1 | 5.6 |
| 0.15 | 7.5 | 0.15 | 5.8 | 0.15 | 5.8 | 0.15 | 2.9 | 0.15 | 5.6 |
| 0.2 | 7.5 | 0.2 | 5.8 | 0.2 | 5.8 | 0.2 | 2.9 | 0.2 | 5.6 |
| 0.25 | 7.5 | 0.25 | 5.8 | 0.25 | 5.8 | 0.25 | 2.9 | 0.25 | 5.6 |
| 0.3 | 7.5 | 0.3 | 5.8 | 0.3 | 5.8 | 0.3 | 2.9 | 0.3 | 5.6 |
| 0.35 | 7.5 | 0.35 | 5.8 | 0.35 | 5.8 | 0.35 | 2.9 | 0.35 | 5.6 |
| 0.4 | 7.5 | 0.4 | 5.8 | 0.4 | 5.8 | 0.4 | 2.9 | 0.4 | 5.6 |
| 0.45 | 7.5 | 0.45 | 5.8 | 0.45 | 5.8 | 0.45 | 2.9 | 0.45 | 5.6 |
| 0.5 | 7.5 | 0.5 | 5.8 | 0.5 | 5.8 | 0.5 | 2.9 | 0.5 | 5.6 |
| 0.55 | 7.5 | 0.55 | 5.7 | 0.55 | 5.8 | 0.55 | 2.9 | 0.55 | 5.6 |
| 0.6 | 7.5 | 0.6 | 5.7 | 0.6 | 5.8 | 0.6 | 2.9 | 0.6 | 5.6 |
| 0.65 | 7.5 | 0.65 | 5.6 | 0.65 | 5.8 | 0.65 | 2.9 | 0.65 | 5.6 |
| 0.7 | 7.5 | 0.7 | 5.4 | 0.7 | 5.8 | 0.7 | 2.9 | 0.7 | 5.6 |
| 0.75 | 7.3 | 0.75 | 5.2 | 0.75 | 5.8 | 0.75 | 2.9 | 0.75 | 5.5 |
| 0.8 | 7.0 | 0.8 | 4.9 | 0.8 | 5.8 | 0.8 | 2.7 | 0.8 | 5.2 |
| 0.85 | 6.4 | 0.85 | 4.4 | 0.85 | 5.7 | 0.85 | 2.5 | 0.85 | 4.8 |
| 0.9 | 5.4 | 0.9 | 3.6 | 0.9 | 4.9 | 0.9 | 2.2 | 0.9 | 4.1 |
| 0.95 | 3.7 | 0.95 | 2.6 | 0.95 | 3.5 | 0.95 | 1.8 | 0.95 | 2.9 |
| 1 | 1.2 | 1 | 1.2 | 1 | 1.2 | 1 | 1.2 | 1 | 1.2 |

HF-HFO-1234yf-HFC-245cb-HFO-1234zeZ-HCFO-1233zdE

| Organics 0.9 F1234yf + 0.033 F1234zeZ + 0.033 F245cb + 0.034 F1233zdE | | Organics 0.033 F1234yf + 0.9 F1234zeZ + 0.033 F245cb + 0.034 F1233zdE | | Organics 0.033 F1234yf + 0.033 F1234zeZ + 0.9 F245cb + 0.034 F1233zdE | | Organics 0.034 F1234yf + 0.033 F1234zeZ − 0.033 F245cb − 0.9 F1233zdE | | Organics 0.25 F1234yf + 0.25 F1234zeZ + 0.25 F245cb + 0.25 F1233zdE | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 2.1 | 0 | 4.5 | 0 | 1.7 | 0 | 3.7 |
| 0.05 | 7.4 | 0.05 | 3.2 | 0.05 | 5.7 | 0.05 | 2.8 | 0.05 | 4.8 |
| 0.1 | 7.4 | 0.1 | 3.2 | 0.1 | 5.7 | 0.1 | 2.8 | 0.1 | 4.8 |
| 0.15 | 7.4 | 0.15 | 3.2 | 0.15 | 5.7 | 0.15 | 2.8 | 0.15 | 4.8 |
| 0.2 | 7.4 | 0.2 | 3.2 | 0.2 | 5.7 | 0.2 | 2.8 | 0.2 | 4.8 |
| 0.25 | 7.4 | 0.25 | 3.2 | 0.25 | 5.7 | 0.25 | 2.8 | 0.25 | 4.8 |
| 0.3 | 7.4 | 0.3 | 3.2 | 0.3 | 5.7 | 0.3 | 2.8 | 0.3 | 4.8 |
| 0.35 | 7.4 | 0.35 | 3.2 | 0.35 | 5.7 | 0.35 | 2.8 | 0.35 | 4.8 |
| 0.4 | 7.4 | 0.4 | 3.2 | 0.4 | 5.7 | 0.4 | 2.8 | 0.4 | 4.8 |
| 0.45 | 7.4 | 0.45 | 3.2 | 0.45 | 5.7 | 0.45 | 2.8 | 0.45 | 4.8 |
| 0.5 | 7.4 | 0.5 | 3.2 | 0.5 | 5.7 | 0.5 | 2.8 | 0.5 | 4.8 |
| 0.55 | 7.4 | 0.55 | 3.2 | 0.55 | 5.7 | 0.55 | 2.8 | 0.55 | 4.8 |
| 0.6 | 7.4 | 0.6 | 3.2 | 0.6 | 5.7 | 0.6 | 2.8 | 0.6 | 4.9 |
| 0.65 | 7.4 | 0.65 | 3.2 | 0.65 | 5.7 | 0.65 | 2.8 | 0.65 | 4.9 |
| 0.7 | 7.4 | 0.7 | 3.2 | 0.7 | 5.7 | 0.7 | 2.8 | 0.7 | 4.9 |
| 0.75 | 7.2 | 0.75 | 3.2 | 0.75 | 5.7 | 0.75 | 2.8 | 0.75 | 4.9 |
| 0.8 | 6.9 | 0.8 | 3.0 | 0.8 | 5.7 | 0.8 | 2.7 | 0.8 | 4.7 |
| 0.85 | 6.4 | 0.85 | 2.8 | 0.85 | 5.7 | 0.85 | 2.5 | 0.85 | 4.3 |
| 0.9 | 5.4 | 0.9 | 2.5 | 0.9 | 4.9 | 0.9 | 2.2 | 0.9 | 3.7 |
| 0.95 | 3.7 | 0.95 | 2.0 | 0.95 | 3.5 | 0.95 | 1.8 | 0.95 | 2.7 |
| 1 | 1.2 | 1 | 1.2 | 1 | 1.2 | 1 | 1.2 | 1 | 1.2 |

-continued

| HF-HFO-1234yf-HFC-245cb-HCFO-1233zdE-HFO-1243zf ||||||||||
| --- | --- | --- | --- | --- | --- | --- | --- | --- | --- |
| Organics 0.9 F1234yf + 0.033 F1233zdE + 0.033 F245cb + 0.034 F1243zf || Organics 0.033 F1234yf + 0.9 F1233zdE + 0.033 F245cb + 0.034 F1243zf || Organics 0.033 F1234yf + 0.033 F1233zdE + 0.9 F245cb + 0.034 F1243zf || Organics 0.034 F1234yf + 0.033 F1233zdE + 0.033 F245cb + 0.9 F1243zf || Organics 0.25 F1234yf + 0.25 F1233zdE + 0.25 F245cb + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.8 | 0 | 4.7 | 0 | 5.7 | 0 | 4.8 |
| 0.05 | 7.5 | 0.05 | 2.9 | 0.05 | 5.8 | 0.05 | 6.7 | 0.05 | 5.9 |
| 0.1 | 7.5 | 0.1 | 2.9 | 0.1 | 5.8 | 0.1 | 6.7 | 0.1 | 5.9 |
| 0.15 | 7.5 | 0.15 | 2.9 | 0.15 | 5.8 | 0.15 | 6.7 | 0.15 | 5.9 |
| 0.2 | 7.5 | 0.2 | 2.9 | 0.2 | 5.8 | 0.2 | 6.7 | 0.2 | 5.9 |
| 0.25 | 7.5 | 0.25 | 2.9 | 0.25 | 5.8 | 0.25 | 6.7 | 0.25 | 5.9 |
| 0.3 | 7.5 | 0.3 | 2.9 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.9 |
| 0.55 | 7.5 | 0.55 | 2.9 | 0.55 | 5.8 | 0.55 | 6.7 | 0.55 | 5.9 |
| 0.6 | 7.5 | 0.6 | 2.9 | 0.6 | 5.8 | 0.6 | 6.6 | 0.6 | 5.9 |
| 0.65 | 7.5 | 0.65 | 2.9 | 0.65 | 5.8 | 0.65 | 6.6 | 0.65 | 5.9 |
| 0.7 | 7.5 | 0.7 | 2.9 | 0.7 | 5.8 | 0.7 | 6.5 | 0.7 | 5.9 |
| 0.75 | 7.3 | 0.75 | 2.9 | 0.75 | 5.8 | 0.75 | 6.3 | 0.75 | 5.8 |
| 0.8 | 7.0 | 0.8 | 2.8 | 0.8 | 5.8 | 0.8 | 6.1 | 0.8 | 5.6 |
| 0.85 | 6.5 | 0.85 | 2.6 | 0.85 | 5.8 | 0.85 | 5.6 | 0.85 | 5.1 |
| 0.9 | 5.4 | 0.9 | 2.3 | 0.9 | 5.0 | 0.9 | 4.7 | 0.9 | 4.4 |
| 0.95 | 3.8 | 0.95 | 1.8 | 0.95 | 3.5 | 0.95 | 3.4 | 0.95 | 3.1 |
| 1 | 1.2 | 1 | 1.2 | 1 | 1.2 | 1 | 1.2 | 1 | 1.2 |

| HF-HCFO-1233xf-HFC-245cb-HCFO-1233zdE-HFO-1234yf ||||||||||
| --- | --- | --- | --- | --- | --- | --- | --- | --- | --- |
| Organics 0.9 F1233xf + 0.033 F1233zdE + 0.033 F245cb + 0.034 F1234yf || Organics 0.033 F1233xf + 0.9 F1233zdE + 0.033 F245cb + 0.034 F1234yf || Organics 0.033 F1233xf + 0.033 F1233zdE + 0.9 F245cb + 0.034 F1234yf || Organics 0.034 F1233xf + 0.033 F1233zdE + 0.033 F245cb + 0.9 F1234yf || Organics 0.25 F1233xf + 0.25 F1233zdE + 0.25 F245cb + 0.25 F1234yf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 1.7 | 0 | 4.5 | 0 | 6.4 | 0 | 3.7 |
| 0.05 | 3.0 | 0.05 | 2.8 | 0.05 | 5.7 | 0.05 | 7.4 | 0.05 | 4.8 |
| 0.1 | 3.0 | 0.1 | 2.8 | 0.1 | 5.7 | 0.1 | 7.4 | 0.1 | 4.8 |
| 0.15 | 3.0 | 0.15 | 2.8 | 0.15 | 5.7 | 0.15 | 7.4 | 0.15 | 4.8 |
| 0.2 | 3.0 | 0.2 | 2.8 | 0.2 | 5.7 | 0.2 | 7.4 | 0.2 | 4.8 |
| 0.25 | 3.0 | 0.25 | 2.8 | 0.25 | 5.7 | 0.25 | 7.4 | 0.25 | 4.8 |
| 0.3 | 3.0 | 0.3 | 2.8 | 0.3 | 5.7 | 0.3 | 7.4 | 0.3 | 4.8 |
| 0.35 | 3.0 | 0.35 | 2.8 | 0.35 | 5.7 | 0.35 | 7.4 | 0.35 | 4.8 |
| 0.4 | 3.0 | 0.4 | 2.8 | 0.4 | 5.7 | 0.4 | 7.4 | 0.4 | 4.8 |
| 0.45 | 3.0 | 0.45 | 2.8 | 0.45 | 5.7 | 0.45 | 7.4 | 0.45 | 4.8 |
| 0.5 | 3.0 | 0.5 | 2.8 | 0.5 | 5.7 | 0.5 | 7.4 | 0.5 | 4.8 |
| 0.55 | 3.0 | 0.55 | 2.8 | 0.55 | 5.7 | 0.55 | 7.4 | 0.55 | 4.8 |
| 0.6 | 3.0 | 0.6 | 2.8 | 0.6 | 5.7 | 0.6 | 7.4 | 0.6 | 4.8 |
| 0.65 | 3.0 | 0.65 | 2.8 | 0.65 | 5.7 | 0.65 | 7.4 | 0.65 | 4.9 |
| 0.7 | 3.0 | 0.7 | 2.8 | 0.7 | 5.7 | 0.7 | 7.4 | 0.7 | 4.9 |
| 0.75 | 3.0 | 0.75 | 2.8 | 0.75 | 5.7 | 0.75 | 7.2 | 0.75 | 4.9 |
| 0.8 | 2.8 | 0.8 | 2.7 | 0.8 | 5.7 | 0.8 | 6.9 | 0.8 | 4.7 |
| 0.85 | 2.6 | 0.85 | 2.5 | 0.85 | 5.7 | 0.85 | 6.4 | 0.85 | 4.3 |
| 0.9 | 2.3 | 0.9 | 2.2 | 0.9 | 4.9 | 0.9 | 5.4 | 0.9 | 3.7 |
| 0.95 | 1.8 | 0.95 | 1.8 | 0.95 | 3.5 | 0.95 | 3.7 | 0.95 | 2.7 |
| 1 | 1.2 | 1 | 1.2 | 1 | 1.2 | 1 | 1.2 | 1 | 1.2 |

Example 11: Temperature and Pressure Range of Penternary Mixtures

|  | Boiling point range | |
|---|---|---|
| System with 5 compounds | Temperature ° C. | Pressure bar |
| HF-HCFO-1233xf-HFC-245cb-HCFO-1233zdE-HFO-1234zeE | 0 to 40 | ~1.0 to ~8.9 |
| HF-HCFO-1233xf-HFC-245cb-HCFO-1233zdE-HFO-1234zeZ | 0 to 40 | ~1.0 to ~8.8 |
| HF-HCFO-1233xf-HFC-245cb-HCFO-1233zdE-HFO-1243zf | 0 to 40 | ~1.0 to ~10.0 |
| HF-HCFO-1233xf-HFO-1234yf-HCFO-1233zdE-HFO-1243zf | 0 to 40 | ~1.0 to ~11.2 |
| HF-HCFO-1233xf-HCFO-1233zdE-HFO-1234zeE-HFO-1234zeZ | 0 to 40 | ~0.9 to ~8.6 |
| HF-HCFO-1233xf-HCFO-1233zdE-HFO-1234zeE-HFO-1243zf | 0 to 40 | ~1.0 to ~10.1 |
| HF-HCFO-1233xf-HCFO-1233zdE-HFO-1234zeZ-HFO-1243zf | 0 to 40 | ~1.0 to ~9.9 |
| HF-HFC-245cb-HCFO-1233zdE-HFO-1234zeE-HFO-1234zeZ | 0 to 40 | ~1.0 to ~8.9 |
| HF-HFC-245cb-HCFO-1233zdE-HFO-1234zeE-HFO-1243zf | 0 to 40 | ~1.1 to ~10.2 |
| HF-HFC-245cb-HCFO-1233zdE-HFO-1234zeZ-HFO-1243zf | 0 to 40 | ~1.0 to ~10.1 |
| HF-HCFO-1233zdE-HFO-1234zeE-HFO-1234zeZ-HFO-1243zf | 0 to 40 | ~1.0 to ~10.1 |
| HF-HCFO-1233xf-HFC-245cb-HCFO-1233zdE-HFO-1234yf | 0 to 40 | ~1.0 to ~11.2 |
| HF-HCFO-1233xf-HFO-1234yf-HFO-1234zeE-HCFO-1233zdE | 0 to 40 | ~1.0 to ~11.2 |
| HF-HCFO-1233xf-HFO-1234yf-HFO-1234zeZ-HCFO-1233zdE | 0 to 40 | ~1.0 to ~11.1 |
| HF-HFO-1234yf-HFO-1234zeE-HFO-1234zeZ-HCFO-1233zdE | 0 to 40 | ~1.0 to ~11.2 |
| HF-HFO-1234yf-HFO-1234zeE-HCFO-1233zdE-HFO-1243zf | 0 to 40 | ~1.0 to ~11.4 |
| HF-HFO-1234yf-HFO-1234zeZ-HCFO-1233zdE-HFO-1243zf | 0 to 40 | ~1.1 to ~11.2 |
| HF-HFO-1234yf-HFC-245cb-HFO-1234zeE-HCFO-1233zdE | 0 to 40 | ~1.1 to ~11.4 |
| HF-HFO-1234yf-HFC-245cb-HFO-1234zeZ-HCFO-1233zdE | 0 to 40 | ~1.0 to ~11.2 |
| HF-HFO-1234yf-HFC-245cb-HCFO-1233zdE-HFO-1243zf | 0 to 40 | ~1.1 to ~11.4 |

Example 12: Decantation Range of Penternary Mixtures

|  | Decantation ranges Mass percentage of HF | | |
|---|---|---|---|
| System with 5 compounds | Isotherm 0° C. | Isotherm 25° C. | Isotherm 40° C. |
| HF-HCFO-1233xf-HFC-245cb-HCFO-1233zdE-HFO-1234zeE | 5-75 | 5-70 | 10-60 |
| HF-HCFO-1233xf-HFC-245cb-HCFO-1233zdE-HFO-1234zeZ | 5-80 | 5-75 | 5-70 |
| HF-HCFO-1233xf-HFC-245cb-HCFO-1233zdE-HFO-1243zf | 5-75 | 5-70 | 5-65 |
| HF-HCFO-1233xf-HCFO-1233zdE-HFO-1234zeE-HFO-1234zeZ | 5-75 | 5-70 | 5-60 |
| HF-HCFO-1233xf-HCFO-1233zdE-HFO-1234zeE-HFO-1243zf | 5-75 | 5-65 | 15-45 |
| HF-HCFO-1233xf-HCFO-1233zdE-HFO-1234zeZ-HFO-1243zf | 5-75 | 5-70 | 10-60 |
| HF-HFC-245cb-HCFO-1233zdE-HFO-1234zeE-HFO-1234zeZ | 5-75 | 5-70 | 10-60 |
| HF-HFC-245cb-HCFO-1233zdE-HFO-1234zeE-HFO-1243zf | 5-75 | 10-65 | * |
| HF-HFC-245cb-HCFO-1233zdE-HFO-1234zeZ-HFO-1243zf | 5-75 | 5-70 | 10-60 |
| HF-HCFO-1233zdE-HFO-1234zeE-HFO-1234zeZ-HFO-1243zf | 5-75 | 5-65 | 15-50 |
| HF-HCFO-1233xf-HFC-245cb-HCFO-1233zdE-HFO-1234yf | 5-75 | 5-75 | 10-65 |
| HF-HCFO-1233xf-HFO-1234yf-HFO-1234zeE-HCFO-1233zdE | 5-75 | 5-65 | 10-50 |
| HF-HCFO-1233xf-HFO-1234yf-HFO-1234zeZ-HCFO-1233zdE | 5-75 | 5-70 | 10-60 |
| HF-HCFO-1233xf-HFO-1234yf-HCFO-1233zdE-HFO-1243zf | 5-75 | 5-65 | 15-45 |

|  | Decantation ranges Mass percentage of HF | | |
|---|---|---|---|
| System with 5 compounds | Isotherm 0° C. | Isotherm 25° C. | Isotherm 40° C. |
| HF-HFO-1234yf-HFO-1234zeE-HFO-1234zeZ-HCFO-1233zdE | 5-75 | 5-65 | 15-45 |
| HF-HFO-1234yf-HFO-1234zeE-HCFO-1233zdE-HFO-1243zf | 5-70 | 10-60 | * |
| HF-HFO-1234yf-HFO-1234zeZ-HCFO-1233zdE-HFO-1243zf | 5-75 | 10-65 | 15-45 |
| HF-HFO-1234yf-HFC-245cb-HFO-1234zeE-HCFO-1233zdE | 5-75 | 10-70 | * |
| HF-HFO-1234yf-HFC-245cb-HFO-1234zeZ-HCFO-1233zdE | 5-75 | 5-75 | 10-65 |
| HF-HFO-1234yf-HFC-245cb-HCFO-1233zdE-HFO-1243zf | 5-75 | 10-70 | * |

Example 13: System with Six Compounds, Isotherm at 25° C.

| HF-HCFO-1233xf-HFC-245cb-HFO-1234zeE-HFO-1234zeZ-HCFO-1233zdE | | | | | | | | | | |
|---|---|---|---|---|---|---|---|---|---|---|
| Organics 0.2 F1233xf + 0.2 F245cb + 0.2 F1243zf + 0.2 F1234zeE + 0.2 F1233zdE | | Organics 0.96 F1233xf + 0.01 F245cb + 0.01 F1233zdE + 0.01 F1234zeE + 0.01 F1234zeZ | | Organics 0.01 F1233xf + 0.96 F245cb + 0.01 F1233zdE + 0.01 F1234zeE + 0.01 F1234zeZ | | Organics 0.01 F1233xf + 0.01 F245cb + 0.01 F1233zdE + 0.96 F1234zeE + 0.01 F1234zeZ | | Organics 0.01 F1233xf + 0.01 F245cb + 0.01 F1233zdE + 0.01 F1234zeE + 0.96 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.9 | 0 | 1.6 | 0 | 4.6 | 0 | 1.4 | 0 | 1.9 |
| 0.05 | 4.0 | 0.05 | 2.7 | 0.05 | 5.7 | 0.05 | 2.5 | 0.05 | 3.0 |
| 0.1 | 4.0 | 0.1 | 2.7 | 0.1 | 5.7 | 0.1 | 2.5 | 0.1 | 3.0 |
| 0.15 | 4.0 | 0.15 | 2.7 | 0.15 | 5.7 | 0.15 | 2.5 | 0.15 | 3.0 |
| 0.2 | 4.0 | 0.2 | 2.7 | 0.2 | 5.7 | 0.2 | 2.5 | 0.2 | 3.0 |
| 0.25 | 4.0 | 0.25 | 2.7 | 0.25 | 5.7 | 0.25 | 2.5 | 0.25 | 3.0 |
| 0.3 | 4.0 | 0.3 | 2.7 | 0.3 | 5.7 | 0.3 | 2.5 | 0.3 | 3.0 |
| 0.35 | 4.0 | 0.35 | 2.7 | 0.35 | 5.7 | 0.35 | 2.5 | 0.35 | 3.0 |
| 0.4 | 4.0 | 0.4 | 2.7 | 0.4 | 5.7 | 0.4 | 2.5 | 0.4 | 3.0 |
| 0.45 | 4.0 | 0.45 | 2.7 | 0.45 | 5.7 | 0.45 | 2.5 | 0.45 | 3.0 |
| 0.5 | 4.0 | 0.5 | 2.7 | 0.5 | 5.7 | 0.5 | 2.5 | 0.5 | 3.0 |
| 0.55 | 4.0 | 0.55 | 2.7 | 0.55 | 5.7 | 0.55 | 2.5 | 0.55 | 3.0 |
| 0.6 | 4.0 | 0.6 | 2.7 | 0.6 | 5.7 | 0.6 | 2.5 | 0.6 | 3.0 |
| 0.65 | 4.0 | 0.65 | 2.7 | 0.65 | 5.7 | 0.65 | 2.5 | 0.65 | 3.0 |
| 0.7 | 4.0 | 0.7 | 2.7 | 0.7 | 5.7 | 0.7 | 2.5 | 0.7 | 3.0 |
| 0.75 | 4.0 | 0.75 | 2.7 | 0.75 | 5.7 | 0.75 | 2.5 | 0.75 | 3.0 |
| 0.8 | 3.8 | 0.8 | 2.6 | 0.8 | 5.8 | 0.8 | 2.4 | 0.8 | 2.6 |
| 0.85 | 3.5 | 0.85 | 2.4 | 0.85 | 5.8 | 0.85 | 2.2 | 0.85 | 2.6 |
| 0.9 | 3.0 | 0.9 | 2.1 | 0.9 | 5.0 | 0.9 | 2.0 | 0.9 | 2.3 |
| 0.95 | 2.3 | 0.95 | 1.7 | 0.95 | 3.5 | 0.95 | 1.7 | 0.95 | 1.9 |
| 1 | 1.2 | 1 | 1.2 | 1 | 1.2 | 1 | 1.2 | 1 | 1.2 |

| HF-HCFO-1233xf-HFC-245cb-HFO-1234zeE-HCFO-1233zdE-HFO-1243zf | | | | | | | | | | |
|---|---|---|---|---|---|---|---|---|---|---|
| Organics 0.2 F1233xf + 0.2 F245cb + 0.2 F1243zf + 0.2 F1234zeE + 0.2 F1233zdE | | Organics 0.96 F1233xf + 0.01 F1243zf + 0.01 F1234zeE + 0.01 F1233zdE | | Organics 0.01 F1233xf + 0.96 F1243zf + 0.01 F1234zeE + 0.01 F1233zdE | | Organics 0.01 F1233xf + 0.01 F1243zf + 0.96 F1234zeE + 0.01 F1233zdE | | Organics 0.01 F1233xf + 0.01 F1243zf + 0.96 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 1.7 | 0 | 4.6 | 0 | 5.8 | 0 | 1.5 |
| 0.05 | 4.9 | 0.05 | 2.8 | 0.05 | 5.8 | 0.05 | 6.7 | 0.05 | 2.6 |
| 0.1 | 4.9 | 0.1 | 2.8 | 0.1 | 5.8 | 0.1 | 6.7 | 0.1 | 2.6 |
| 0.15 | 4.9 | 0.15 | 2.8 | 0.15 | 5.8 | 0.15 | 6.7 | 0.15 | 2.6 |
| 0.2 | 4.9 | 0.2 | 2.8 | 0.2 | 5.8 | 0.2 | 6.7 | 0.2 | 2.6 |
| 0.25 | 4.9 | 0.25 | 2.8 | 0.25 | 5.8 | 0.25 | 6.7 | 0.25 | 2.6 |

-continued

| MASSFRAC HF | Organics 0.2 F1233xf + 0.2 F245cb + 0.2 F1243zf + 0.2 F1234zeZ + 0.2 F1233zdE TOTAL PRESSURE bar | MASSFRAC HF | Organics 0.96 F1233xf + 0.01 F245cb + 0.01 F1243zf + 0.01 F1234zeZ + 0.01 F1233zdE TOTAL PRESSURE bar |
|---|---|---|---|
| 0.3 | 4.9 | 0.3 | 2.8 |
| 0.35 | 4.9 | 0.35 | 2.8 |
| 0.4 | 4.9 | 0.4 | 2.8 |
| 0.45 | 4.9 | 0.45 | 2.8 |
| 0.5 | 4.9 | 0.5 | 2.8 |
| 0.55 | 4.9 | 0.55 | 2.8 |
| 0.6 | 4.9 | 0.6 | 2.8 |
| 0.65 | 4.9 | 0.65 | 2.8 |
| 0.7 | 4.9 | 0.7 | 2.8 |
| 0.75 | 4.9 | 0.75 | 2.8 |
| 0.8 | 4.7 | 0.8 | 2.8 |
| 0.85 | 4.5 | 0.85 | 2.6 |
| 0.9 | 4.1 | 0.9 | 2.4 |
| 0.95 | 3.5 | 0.95 | 2.2 |
| 1 | 2.6 | 1 | 1.7 |
|   | 1.2 |   | 1.2 |

HF-HCFO-1233xf-HFC-245cb-HFO-1234zeZ-HCFO-1233zdE-HFO-1243zf

| MASSFRAC HF | Organics 0.01 F1233xf + 0.96 F245cb + 0.01 F1243zf + 0.01 F1234zeZ + 0.01 F1233zdE TOTAL PRESSURE bar | MASSFRAC HF | Organics 0.01 F1233xf + 0.01 F245cb + 0.96 F1243zf + 0.01 F1234zeZ + 0.01 F1233zdE TOTAL PRESSURE bar | MASSFRAC HF | Organics 0.01 F1233xf + 0.01 F245cb + 0.01 F1243zf + 0.96 F1234zeZ + 0.01 F1233zdE TOTAL PRESSURE bar | MASSFRAC HF | Organics 0.01 F1233xf + 0.01 F245cb + 0.01 F1243zf + 0.01 F1234zeZ + 0.96 F1233zdE TOTAL PRESSURE bar |
|---|---|---|---|---|---|---|---|
| 0 | 4.6 | 0 | 5.7 | 0 | 1.9 | 0 | 1.4 |
| 0.05 | 5.7 | 0.05 | 6.7 | 0.05 | 3.0 | 0.05 | 2.5 |
| 0.1 | 5.7 | 0.1 | 6.7 | 0.1 | 3.0 | 0.1 | 2.5 |
| 0.15 | 5.7 | 0.15 | 6.7 | 0.15 | 3.0 | 0.15 | 2.5 |
| 0.2 | 5.7 | 0.2 | 6.7 | 0.2 | 3.0 | 0.2 | 2.5 |
| 0.25 | 5.7 | 0.25 | 6.7 | 0.25 | 3.0 | 0.25 | 2.5 |
| 0.3 | 5.8 | 0.3 | 6.7 | 0.3 | 3.0 | 0.3 | 2.5 |
| 0.35 | 5.8 | 0.35 | 6.7 | 0.35 | 3.0 | 0.35 | 2.5 |
| 0.4 | 5.8 | 0.4 | 6.7 | 0.4 | 3.0 | 0.4 | 2.5 |
| 0.45 | 5.8 | 0.45 | 6.7 | 0.45 | 3.0 | 0.45 | 2.5 |
| 0.5 | 5.8 | 0.5 | 6.7 | 0.5 | 3.0 | 0.5 | 2.5 |
| 0.55 | 5.8 | 0.55 | 6.7 | 0.55 | 3.0 | 0.55 | 2.5 |
| 0.6 | 5.8 | 0.6 | 6.6 | 0.6 | 3.0 | 0.6 | 2.5 |
| 0.65 | 5.8 | 0.65 | 6.6 | 0.65 | 3.0 | 0.65 | 2.5 |
| 0.7 | 5.8 | 0.7 | 6.5 | 0.7 | 3.0 | 0.7 | 2.5 |
| 0.75 | 5.8 | 0.75 | 6.3 | 0.75 | 3.0 | 0.75 | 2.5 |
| 0.8 | 5.8 | 0.8 | 6.0 | 0.8 | 2.9 | 0.8 | 2.4 |
| 0.85 | 5.8 | 0.85 | 5.5 | 0.85 | 2.7 | 0.85 | 2.3 |
| 0.9 | 5.0 | 0.9 | 4.7 | 0.9 | 2.3 | 0.9 | 2.0 |
| 0.95 | 3.5 | 0.95 | 3.3 | 0.95 | 1.9 | 0.95 | 1.7 |
| 1 | 1.2 | 1 | 1.2 | 1 | 1.2 | 1 | 1.2 |

-continued

HF-HCFO-1233xf-HFO-1234zeE-HFO-1234zeZ-HCFO-1233zdE-HFO-1243zf

| Organics 0.2 F1233xf + 0.2 F1243zf + 0.2 F1233zdE 0.2 F1234zeE + 0.2 F1234zeZ | | Organics 0.96 F1233xf + 0.01 F1243zf + 0.01 F1233zdE + 0.01 F1234zeE + 0.01 F1234zeZ | | Organics 0.01 F1233xf-HFO-1234zeE-HFO-1234zeZ 0.96 F1233zdE + 0.01 F1234zeE + 0.01 F1234zeZ | | Organics 0.01 F1233xf + 0.01 F1243zf + 0.96 F1234zeE + 0.01 F1234zeZ | | Organics 0.01 F1233xf + 0.01 F1243zf + 0.01 F1233zdE + 0.96 F1234zeE + 0.01 F1234zeZ | | Organics 0.01 F1233xf + 0.01 F1243zf + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.2 | 0 | 1.6 | 0 | 5.7 | 0 | 1.4 | 0 | 4.8 | 0 | 1.9 |
| 0.05 | 4.3 | 0.05 | 2.7 | 0.05 | 6.7 | 0.05 | 2.5 | 0.05 | 5.7 | 0.05 | 3.0 |
| 0.1 | 4.3 | 0.1 | 2.7 | 0.1 | 6.7 | 0.1 | 2.5 | 0.1 | 5.8 | 0.1 | 3.0 |
| 0.15 | 4.3 | 0.15 | 2.7 | 0.15 | 6.7 | 0.15 | 2.5 | 0.15 | 5.8 | 0.15 | 3.0 |
| 0.2 | 4.3 | 0.2 | 2.7 | 0.2 | 6.7 | 0.2 | 2.5 | 0.2 | 5.8 | 0.2 | 3.0 |
| 0.25 | 4.3 | 0.25 | 2.7 | 0.25 | 6.7 | 0.25 | 2.5 | 0.25 | 5.8 | 0.25 | 3.0 |
| 0.3 | 4.3 | 0.3 | 2.7 | 0.3 | 6.7 | 0.3 | 2.5 | 0.3 | 5.8 | 0.3 | 3.0 |
| 0.35 | 4.3 | 0.35 | 2.7 | 0.35 | 6.7 | 0.35 | 2.5 | 0.35 | 5.8 | 0.35 | 3.0 |
| 0.4 | 4.3 | 0.4 | 2.7 | 0.4 | 6.7 | 0.4 | 2.5 | 0.4 | 5.8 | 0.4 | 3.0 |
| 0.45 | 4.3 | 0.45 | 2.7 | 0.45 | 6.7 | 0.45 | 2.5 | 0.45 | 5.7 | 0.45 | 3.0 |
| 0.5 | 4.3 | 0.5 | 2.7 | 0.5 | 6.7 | 0.5 | 2.5 | 0.5 | 5.7 | 0.5 | 3.0 |
| 0.55 | 4.2 | 0.55 | 2.7 | 0.55 | 6.6 | 0.55 | 2.5 | 0.55 | 5.7 | 0.55 | 3.0 |
| 0.6 | 4.2 | 0.6 | 2.7 | 0.6 | 6.6 | 0.6 | 2.5 | 0.6 | 5.6 | 0.6 | 3.0 |
| 0.65 | 4.2 | 0.65 | 2.7 | 0.65 | 6.6 | 0.65 | 2.5 | 0.65 | 5.5 | 0.65 | 3.0 |
| 0.7 | 4.2 | 0.7 | 2.7 | 0.7 | 6.5 | 0.7 | 2.5 | 0.7 | 5.3 | 0.7 | 3.0 |
| 0.75 | 4.0 | 0.75 | 2.7 | 0.75 | 6.3 | 0.75 | 2.5 | 0.75 | 5.1 | 0.75 | 3.0 |
| 0.8 | 3.8 | 0.8 | 2.6 | 0.8 | 6.0 | 0.8 | 2.4 | 0.8 | 4.7 | 0.8 | 2.8 |
| 0.85 | 3.5 | 0.85 | 2.4 | 0.85 | 5.5 | 0.85 | 2.2 | 0.85 | 4.3 | 0.85 | 2.6 |
| 0.9 | 3.0 | 0.9 | 2.1 | 0.9 | 4.7 | 0.9 | 2.0 | 0.9 | 3.6 | 0.9 | 2.3 |
| 0.95 | 2.2 | 0.95 | 1.7 | 0.95 | 3.3 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HFC-245cb-HFO-1234zeE-HFO-1234zeZ-HCFO-1233zdE-HFO-1243zf

| Organics 0.2 F245cb + 0.2 F1243zf + 0.2 F1233zdE 0.2 F1234zeE + 0.2 F1234zeZ | | Organics 0.96 F245cb + 0.01 F1243zf + 0.01 F1233zdE + 0.01 F1234zeE + 0.01 F1234zeZ | | Organics 0.01 F245cb + 0.96 F1243zf + 0.01 F1233zdE + 0.01 F1234zeE + 0.01 F1234zeZ | | Organics 0.01 F245cb + 0.01 F1243zf + 0.96 F1233zdE + 0.01 F1234zeE + 0.01 F1234zeZ | | Organics 0.01 F245cb + 0.01 F1243zf + 0.01 F1233zdE + 0.96 F1234zeE + 0.01 F1234zeZ | | Organics 0.01 F245cb + 0.01 F1243zf + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 4.6 | 0 | 5.8 | 0 | 1.5 | 0 | 4.8 | 0 | 1.9 |
| 0.05 | 4.9 | 0.05 | 5.8 | 0.05 | 6.7 | 0.05 | 2.6 | 0.05 | 5.8 | 0.05 | 3.0 |
| 0.1 | 4.9 | 0.1 | 5.8 | 0.1 | 6.7 | 0.1 | 2.6 | 0.1 | 5.8 | 0.1 | 3.0 |
| 0.15 | 4.9 | 0.15 | 5.8 | 0.15 | 6.7 | 0.15 | 2.6 | 0.15 | 5.8 | 0.15 | 3.0 |
| 0.2 | 4.9 | 0.2 | 5.8 | 0.2 | 6.7 | 0.2 | 2.6 | 0.2 | 5.8 | 0.2 | 3.0 |
| 0.25 | 4.9 | 0.25 | 5.8 | 0.25 | 6.7 | 0.25 | 2.6 | 0.25 | 5.8 | 0.25 | 3.0 |
| 0.3 | 4.9 | 0.3 | 5.8 | 0.3 | 6.7 | 0.3 | 2.6 | 0.3 | 5.8 | 0.3 | 3.0 |

-continued

| Organics 0.2 F1233xf + 0.2 F1234yf + 0.2 F245cb + F1234zeE + 0.2 F1233zdE | | Organics 0.96 F1233xf + 0.01 F1234yf + 0.01 F245cb + 0.01 F1234zeE + 0.01 F1233zdE | | Organics 0.01 F1233xf + 0.96 F1234yf + 0.01 F245cb + 0.01 F1234zeE + 0.01 F1233zdE | | Organics 0.01 F1233xf + 0.01 F1234yf + 0.96 F245cb + 0.01 F1234zeE + 0.01 F1233zdE | | Organics 0.01 F1233xf + 0.01 F1234yf + 0.01 F245cb + 0.96 F1234zeE + 0.01 F1233zdE | | Organics 0.01 F1233xf + 0.01 F1234yf + 0.01 F245cb + 0.01 F1234zeE + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0.35 | 4.9 | 0.35 | 5.8 | 0.35 | 6.7 | 0.35 | 2.6 | 0.35 | 5.8 | 0.35 | 3.0 |
| 0.4 | 4.9 | 0.4 | 5.8 | 0.4 | 6.7 | 0.4 | 2.6 | 0.4 | 5.8 | 0.4 | 3.0 |
| 0.45 | 4.9 | 0.45 | 5.8 | 0.45 | 6.7 | 0.45 | 2.6 | 0.45 | 5.8 | 0.45 | 3.0 |
| 0.5 | 4.9 | 0.5 | 5.8 | 0.5 | 6.7 | 0.5 | 2.6 | 0.5 | 5.7 | 0.5 | 3.0 |
| 0.55 | 4.9 | 0.55 | 5.8 | 0.55 | 6.7 | 0.55 | 2.6 | 0.55 | 5.7 | 0.55 | 3.0 |
| 0.6 | 4.9 | 0.6 | 5.8 | 0.6 | 6.6 | 0.6 | 2.6 | 0.6 | 5.6 | 0.6 | 3.0 |
| 0.65 | 4.9 | 0.65 | 5.8 | 0.65 | 6.6 | 0.65 | 2.6 | 0.65 | 5.5 | 0.65 | 3.0 |
| 0.7 | 4.9 | 0.7 | 5.8 | 0.7 | 6.5 | 0.7 | 2.6 | 0.7 | 5.4 | 0.7 | 3.0 |
| 0.75 | 4.8 | 0.75 | 5.8 | 0.75 | 6.3 | 0.75 | 2.5 | 0.75 | 5.1 | 0.75 | 3.0 |
| 0.8 | 4.5 | 0.8 | 5.8 | 0.8 | 6.0 | 0.8 | 2.4 | 0.8 | 4.8 | 0.8 | 2.9 |
| 0.85 | 4.2 | 0.85 | 5.8 | 0.85 | 5.6 | 0.85 | 2.3 | 0.85 | 4.3 | 0.85 | 2.7 |
| 0.9 | 3.5 | 0.9 | 5.0 | 0.9 | 4.7 | 0.9 | 2.0 | 0.9 | 3.6 | 0.9 | 2.4 |
| 0.95 | 2.6 | 0.95 | 3.5 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HFO-1234zeE-HCFO-1233zdE

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|
| 0 | 3.9 | 0 | 1.7 | 0 | 6.7 | 0 | 4.6 |
| 0.05 | 5.0 | 0.05 | 2.8 | 0.05 | 7.6 | 0.05 | 5.8 |
| 0.1 | 5.0 | 0.1 | 2.8 | 0.1 | 7.6 | 0.1 | 5.8 |
| 0.15 | 5.0 | 0.15 | 2.8 | 0.15 | 7.6 | 0.15 | 5.8 |
| 0.2 | 5.0 | 0.2 | 2.8 | 0.2 | 7.6 | 0.2 | 5.8 |
| 0.25 | 5.0 | 0.25 | 2.8 | 0.25 | 7.6 | 0.25 | 5.8 |
| 0.3 | 5.0 | 0.3 | 2.8 | 0.3 | 7.6 | 0.3 | 5.8 |
| 0.35 | 5.0 | 0.35 | 2.8 | 0.35 | 7.6 | 0.35 | 5.8 |
| 0.4 | 5.0 | 0.4 | 2.8 | 0.4 | 7.6 | 0.4 | 5.8 |
| 0.45 | 5.0 | 0.45 | 2.8 | 0.45 | 7.6 | 0.45 | 5.8 |
| 0.5 | 5.0 | 0.5 | 2.8 | 0.5 | 7.6 | 0.5 | 5.8 |
| 0.55 | 5.0 | 0.55 | 2.8 | 0.55 | 7.6 | 0.55 | 5.7 |
| 0.6 | 5.0 | 0.6 | 2.8 | 0.6 | 7.6 | 0.6 | 5.6 |
| 0.65 | 5.0 | 0.65 | 2.8 | 0.65 | 7.6 | 0.65 | 5.5 |
| 0.7 | 5.1 | 0.7 | 2.8 | 0.7 | 7.6 | 0.7 | 5.4 |
| 0.75 | 5.0 | 0.75 | 2.8 | 0.75 | 7.5 | 0.75 | 5.1 |
| 0.8 | 4.7 | 0.8 | 2.6 | 0.8 | 7.1 | 0.8 | 4.8 |
| 0.85 | 4.3 | 0.85 | 2.5 | 0.85 | 6.5 | 0.85 | 4.3 |
| 0.9 | 3.7 | 0.9 | 2.2 | 0.9 | 5.5 | 0.9 | 3.6 |
| 0.95 | 2.7 | 0.95 | 1.8 | 0.95 | 3.8 | 0.95 | 2.6 |
| 1 | 1.2 | 1 | 1.2 | 1 | 1.2 | 1 | 1.2 |

| MASSFRAC HF | TOTAL PRESSURE bar |
|---|---|
| 0 | 1.5 |
| 0.05 | 2.6 |
| 0.1 | 2.6 |
| 0.15 | 2.6 |
| 0.2 | 2.6 |
| 0.25 | 2.6 |
| 0.3 | 2.6 |
| 0.35 | 2.6 |
| 0.4 | 2.6 |
| 0.45 | 2.6 |
| 0.5 | 2.6 |
| 0.55 | 2.6 |
| 0.6 | 2.6 |
| 0.65 | 2.6 |
| 0.7 | 2.6 |
| 0.75 | 2.6 |
| 0.8 | 2.6 |
| 0.85 | 2.4 |
| 0.9 | 2.3 |
| 0.95 | 2.0 |
| 1 | 1.7 |
| | 1.2 |

-continued

HF-HCFO-1233xf-HFO-1234yf-HFC-245cb-HFO-1234zeZ-HCFO-1233zdE

| Organics 0.2 F1233xf + 0.2 F1234yf + 0.2 F245cb + 0.2 F1234zeZ + 0.2 F1233zdE | | Organics 0.96 F1233xf + 0.01 F1234yf + 0.01 F245cb + 0.01 F1234zeZ + 0.01 F1233zdE | | Organics 0.01 F1233xf + 0.01 F1234yf + 0.96 F245cb + 0.01 F1234zeZ + 0.01 F1233zdE | | Organics 0.01 F1233xf + 0.01 F1234yf + 0.01 F245cb + 0.96 F1234zeZ + 0.01 F1233zdE | | Organics 0.01 F1233xf + 0.01 F1234yf + 0.01 F245cb + 0.01 F1234zeZ + 0.96 F1233zdE | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.3 | 0 | 1.6 | 0 | 6.6 | 0 | 4.6 | 0 | 1.9 |
| 0.05 | 4.4 | 0.05 | 2.8 | 0.05 | 7.6 | 0.05 | 5.8 | 0.05 | 3.0 |
| 0.1 | 4.4 | 0.1 | 2.8 | 0.1 | 7.6 | 0.1 | 5.8 | 0.1 | 3.0 |
| 0.15 | 4.4 | 0.15 | 2.8 | 0.15 | 7.6 | 0.15 | 5.8 | 0.15 | 3.0 |
| 0.2 | 4.4 | 0.2 | 2.8 | 0.2 | 7.6 | 0.2 | 5.8 | 0.2 | 3.0 |
| 0.25 | 4.4 | 0.25 | 2.8 | 0.25 | 7.6 | 0.25 | 5.8 | 0.25 | 3.0 |
| 0.3 | 4.4 | 0.3 | 2.8 | 0.3 | 7.6 | 0.3 | 5.8 | 0.3 | 3.0 |
| 0.35 | 4.4 | 0.35 | 2.8 | 0.35 | 7.6 | 0.35 | 5.8 | 0.35 | 3.0 |
| 0.4 | 4.4 | 0.4 | 2.8 | 0.4 | 7.6 | 0.4 | 5.8 | 0.4 | 3.0 |
| 0.45 | 4.4 | 0.45 | 2.8 | 0.45 | 7.6 | 0.45 | 5.8 | 0.45 | 3.0 |
| 0.5 | 4.4 | 0.5 | 2.8 | 0.5 | 7.6 | 0.5 | 5.8 | 0.5 | 3.0 |
| 0.55 | 4.4 | 0.55 | 2.8 | 0.55 | 7.6 | 0.55 | 5.8 | 0.55 | 3.0 |
| 0.6 | 4.4 | 0.6 | 2.8 | 0.6 | 7.6 | 0.6 | 5.8 | 0.6 | 3.0 |
| 0.65 | 4.5 | 0.65 | 2.8 | 0.65 | 7.6 | 0.65 | 5.8 | 0.65 | 3.0 |
| 0.7 | 4.5 | 0.7 | 2.8 | 0.7 | 7.6 | 0.7 | 5.8 | 0.7 | 3.0 |
| 0.75 | 4.5 | 0.75 | 2.8 | 0.75 | 7.6 | 0.75 | 5.8 | 0.75 | 3.0 |
| 0.8 | 4.3 | 0.8 | 2.8 | 0.8 | 7.4 | 0.8 | 5.8 | 0.8 | 2.9 |
| 0.85 | 4.0 | 0.85 | 2.6 | 0.85 | 7.1 | 0.85 | 5.8 | 0.85 | 2.7 |
| 0.9 | 3.4 | 0.9 | 2.4 | 0.9 | 6.5 | 0.9 | 5.0 | 0.9 | 2.3 |
| 0.95 | 2.5 | 0.95 | 2.2 | 0.95 | 5.5 | 0.95 | 3.5 | 0.95 | 1.9 |
| 1 | 1.2 | 1 | 1.7 | 1 | 3.8 | 1 | 1.2 | 1 | 1.2 |
|   |     |   | 1.2 |   | 1.2 |   |     |   |     |

HF-HCFO-1233xf-HFO-1234yf-HFC-245cb-HCFO-1233zdE-HFO-1243zf

| Organics 0.96 F1233xf + 0.01 F1234yf + 0.01 F245cb + 0.01 F1233zdE + 0.01 F1243zf | | Organics 0.01 F1233xf + 0.96 F1234yf + 0.01 F245cb + 0.01 F1233zdE + 0.01 F1243zf | | Organics 0.01 F1233xf + 0.01 F1234yf + 0.96 F245cb + 0.01 F1233zdE + 0.01 F1243zf | | Organics 0.01 F1233xf + 0.01 F1234yf + 0.01 F245cb + 0.96 F1233zdE + 0.01 F1243zf | | Organics 0.01 F1233xf + 0.01 F1234yf + 0.01 F245cb + 0.01 F1233zdE + 0.96 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 6.7 | 0 | 4.6 | 0 | 1.5 | 0 | 5.8 |
| 0.05 | 2.8 | 0.05 | 7.6 | 0.05 | 5.8 | 0.05 | 2.6 | 0.05 | 6.7 |
| 0.1 | 2.8 | 0.1 | 7.7 | 0.1 | 5.8 | 0.1 | 2.6 | 0.1 | 6.8 |
| 0.15 | 2.8 | 0.15 | 7.6 | 0.15 | 5.8 | 0.15 | 2.6 | 0.15 | 6.7 |
| 0.2 | 2.8 | 0.2 | 7.6 | 0.2 | 5.8 | 0.2 | 2.6 | 0.2 | 6.7 |
| 0.25 | 2.8 | 0.25 | 7.6 | 0.25 | 5.8 | 0.25 | 2.6 | 0.25 | 6.7 |
| 0.3 | 2.8 | 0.3 | 7.6 | 0.3 | 5.8 | 0.3 | 2.6 | 0.3 | 6.7 |

-continued

| MASSFRAC HF | Organics 0.2 F1233xf + 0.2 F1234yf + 0.2 F1233zdE + F1234zeE + 0.2 F1234zeZ | TOTAL PRESSURE bar | MASSFRAC HF | Organics 0.96 F1233xf + 0.01 F1234yf + 0.01 F1233zdE + 0.01 F1234zeE + 0.01 F1234zeZ | TOTAL PRESSURE bar | MASSFRAC HF | Organics 0.01 F1233xf + 0.96 F1234yf + 0.01 F1233zdE + 0.01 F1234zeE + 0.01 F1234zeZ | TOTAL PRESSURE bar |
|---|---|---|---|---|---|---|---|---|
| 0.35 | 5.3 | | 0.35 | 2.8 | | 0.35 | 7.6 | |
| 0.4 | 5.3 | | 0.4 | 2.8 | | 0.4 | 7.6 | |
| 0.45 | 5.3 | | 0.45 | 2.8 | | 0.45 | 7.6 | |
| 0.5 | 5.3 | | 0.5 | 2.8 | | 0.5 | 7.6 | |
| 0.55 | 5.3 | | 0.55 | 2.8 | | 0.55 | 7.6 | |
| 0.6 | 5.3 | | 0.6 | 2.8 | | 0.6 | 7.6 | |
| 0.65 | 5.3 | | 0.65 | 2.8 | | 0.65 | 7.6 | |
| 0.7 | 5.3 | | 0.7 | 2.8 | | 0.7 | 7.6 | |
| 0.75 | 5.2 | | 0.75 | 2.8 | | 0.75 | 7.5 | |
| 0.8 | 5.0 | | 0.8 | 2.7 | | 0.8 | 7.2 | |
| 0.85 | 4.6 | | 0.85 | 2.5 | | 0.85 | 6.6 | |
| 0.9 | 3.9 | | 0.9 | 2.2 | | 0.9 | 5.5 | |
| 0.95 | 2.8 | | 0.95 | 1.8 | | 0.95 | 3.8 | |
| 1 | 1.2 | | 1 | 1.2 | | 1 | 1.2 | |

HF-HCFO-1233xf-HFO-1234yf-HFO-1234zeE-HFO-1234zeZ-HCFO-1233zdE

| MASSFRAC HF | Organics 0.01 F1233xf + 0.01 F1234yf + 0.96 F1233zdE + 0.01 F1234zeE + 0.01 F1234zeZ | TOTAL PRESSURE bar | MASSFRAC HF | Organics 0.01 F1233xf + 0.01 F1234yf + 0.01 F1233zdE + 0.96 F1234zeE + 0.01 F1234zeZ | TOTAL PRESSURE bar | MASSFRAC HF | Organics 0.01 F1233xf + 0.01 F1234yf + 0.01 F1233zdE + 0.01 F1234zeE + 0.96 F1234zeZ | TOTAL PRESSURE bar |
|---|---|---|---|---|---|---|---|---|
| 0 | | 1.4 | 0 | | 4.8 | 0 | | 1.9 |
| 0.05 | | 2.5 | 0.05 | | 5.8 | 0.05 | | 3.0 |
| 0.1 | | 2.5 | 0.1 | | 5.8 | 0.1 | | 3.0 |
| 0.15 | | 2.5 | 0.15 | | 5.8 | 0.15 | | 3.0 |
| 0.2 | | 2.5 | 0.2 | | 5.8 | 0.2 | | 3.0 |
| 0.25 | | 2.5 | 0.25 | | 5.8 | 0.25 | | 3.0 |
| 0.3 | | 2.5 | 0.3 | | 5.8 | 0.3 | | 3.0 |
| 0.35 | | 2.5 | 0.35 | | 5.8 | 0.35 | | 3.0 |
| 0.4 | | 2.5 | 0.4 | | 5.8 | 0.4 | | 3.0 |
| 0.45 | | 2.5 | 0.45 | | 5.7 | 0.45 | | 3.0 |
| 0.5 | | 2.5 | 0.5 | | 5.7 | 0.5 | | 3.0 |
| 0.55 | | 2.5 | 0.55 | | 5.7 | 0.55 | | 3.0 |
| 0.6 | | 2.5 | 0.6 | | 5.6 | 0.6 | | 3.0 |
| 0.65 | | 2.5 | 0.65 | | 5.5 | 0.65 | | 3.0 |
| 0.7 | | 2.5 | 0.7 | | 5.3 | 0.7 | | 3.0 |
| 0.75 | | 2.5 | 0.75 | | 5.1 | 0.75 | | 3.0 |
| 0.8 | | 2.4 | 0.8 | | 4.8 | 0.8 | | 2.8 |
| 0.85 | | 2.2 | 0.85 | | 4.3 | 0.85 | | 2.6 |
| 0.9 | | 2.0 | 0.9 | | 3.6 | 0.9 | | 2.3 |
| 0.95 | | 1.7 | 0.95 | | 2.6 | 0.95 | | 1.9 |
| 1 | | 1.2 | 1 | | 1.2 | 1 | | 1.2 |

-continued

| HF-HCFO-1233xf-HFO-1234yf-HFO-1234zeE-HCFO-1233zdE-HFO-1243zf | | | | | | | | |
|---|---|---|---|---|---|---|---|---|
| Organics 0.2 F1233xf + 0.2 F1234yf + 0.2 F1243zf + 0.2 F1234zeE + 0.2 F1233zdE | | Organics 0.96 F1233xf + 0.01 F1234yf + 0.01 F1243zf + 0.01 F1234zeE + 0.01 F1233zdE | | Organics 0.01 F1233xf + 0.96 F1234yf + 0.01 F1243zf + 0.01 F1234zeE + 0.01 F1233zdE | | Organics 0.01 F1233xf + 0.01 F1234yf + 0.96 F1243zf + 0.01 F1234zeE + 0.01 F1233zdE | | Organics 0.01 F1233xf + 0.01 F1234yf + 0.01 F1243zf + 0.96 F1234zeE + 0.01 F1233zdE | | Organics 0.01 F1233xf + 0.01 F1234yf + 0.01 F1243zf + 0.01 F1234zeE + 0.96 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.7 | 0 | 6.7 | 0 | 5.8 | 0 | 4.8 | 0 | 1.5 |
| 0.05 | 5.3 | 0.05 | 2.8 | 0.05 | 7.6 | 0.05 | 6.7 | 0.05 | 5.8 | 0.05 | 2.6 |
| 0.1 | 5.3 | 0.1 | 2.8 | 0.1 | 7.6 | 0.1 | 6.7 | 0.1 | 5.8 | 0.1 | 2.6 |
| 0.15 | 5.3 | 0.15 | 2.8 | 0.15 | 7.6 | 0.15 | 6.7 | 0.15 | 5.8 | 0.15 | 2.6 |
| 0.2 | 5.3 | 0.2 | 2.8 | 0.2 | 7.6 | 0.2 | 6.7 | 0.2 | 5.8 | 0.2 | 2.6 |
| 0.25 | 5.3 | 0.25 | 2.8 | 0.25 | 7.6 | 0.25 | 6.7 | 0.25 | 5.8 | 0.25 | 2.6 |
| 0.3 | 5.3 | 0.3 | 2.8 | 0.3 | 7.6 | 0.3 | 6.7 | 0.3 | 5.8 | 0.3 | 2.6 |
| 0.35 | 5.3 | 0.35 | 2.8 | 0.35 | 7.6 | 0.35 | 6.7 | 0.35 | 5.8 | 0.35 | 2.6 |
| 0.4 | 5.3 | 0.4 | 2.8 | 0.4 | 7.6 | 0.4 | 6.7 | 0.4 | 5.8 | 0.4 | 2.6 |
| 0.45 | 5.3 | 0.45 | 2.8 | 0.45 | 7.6 | 0.45 | 6.7 | 0.45 | 5.8 | 0.45 | 2.6 |
| 0.5 | 5.3 | 0.5 | 2.8 | 0.5 | 7.6 | 0.5 | 6.7 | 0.5 | 5.8 | 0.5 | 2.6 |
| 0.55 | 5.3 | 0.55 | 2.8 | 0.55 | 7.6 | 0.55 | 6.7 | 0.55 | 5.7 | 0.55 | 2.6 |
| 0.6 | 5.3 | 0.6 | 2.8 | 0.6 | 7.6 | 0.6 | 6.6 | 0.6 | 5.6 | 0.6 | 2.6 |
| 0.65 | 5.2 | 0.65 | 2.8 | 0.65 | 7.6 | 0.65 | 6.5 | 0.65 | 5.5 | 0.65 | 2.6 |
| 0.7 | 5.1 | 0.7 | 2.8 | 0.7 | 7.6 | 0.7 | 6.3 | 0.7 | 5.4 | 0.7 | 2.6 |
| 0.75 | 5.0 | 0.75 | 2.8 | 0.75 | 7.5 | 0.75 | 6.1 | 0.75 | 5.1 | 0.75 | 2.6 |
| 0.8 | 4.7 | 0.8 | 2.6 | 0.8 | 7.1 | 0.8 | 5.6 | 0.8 | 4.8 | 0.8 | 2.4 |
| 0.85 | 4.3 | 0.85 | 2.5 | 0.85 | 6.5 | 0.85 | 4.7 | 0.85 | 4.3 | 0.85 | 2.3 |
| 0.9 | 3.6 | 0.9 | 2.2 | 0.9 | 5.5 | 0.9 | 4.7 | 0.9 | 3.6 | 0.9 | 2.0 |
| 0.95 | 2.6 | 0.95 | 1.8 | 0.95 | 3.8 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

| HF-HCFO-1233xf-HFO-1234yf-HFO-1234zeZ-HCFO-1233zdE-HFO-1243zf | | | | | | | | |
|---|---|---|---|---|---|---|---|---|
| Organics 0.2 F1233xf + 0.2 F1234yf + 0.2 F1243zf + 0.2 F1234zeZ + 0.2 F1233zdE | | Organics 0.96 F1233xf + 0.01 F1234yf + 0.01 F1243zf + 0.01 F1234zeZ + 0.01 F1233zdE | | Organics 0.01 F1233xf + 0.96 F1234yf + 0.01 F1243zf + 0.01 F1234zeZ + 0.01 F1233zdE | | Organics 0.01 F1233xf + 0.01 F1234yf + 0.96 F1243zf + 0.01 F1234zeZ + 0.01 F1233zdE | | Organics 0.01 F1233xf + 0.01 F1234yf + 0.01 F1243zf + 0.96 F1234zeZ + 0.01 F1233zdE | | Organics 0.01 F1233xf + 0.01 F1234yf + 0.01 F1243zf + 0.01 F1234zeZ + 0.96 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.6 | 0 | 1.7 | 0 | 6.6 | 0 | 5.7 | 0 | 1.9 | 0 | 1.4 |
| 0.05 | 4.7 | 0.05 | 2.8 | 0.05 | 7.6 | 0.05 | 6.7 | 0.05 | 3.0 | 0.05 | 2.6 |
| 0.1 | 4.7 | 0.1 | 2.8 | 0.1 | 7.6 | 0.1 | 6.7 | 0.1 | 3.0 | 0.1 | 2.6 |
| 0.15 | 4.7 | 0.15 | 2.8 | 0.15 | 7.6 | 0.15 | 6.7 | 0.15 | 3.0 | 0.15 | 2.6 |
| 0.2 | 4.7 | 0.2 | 2.8 | 0.2 | 7.6 | 0.2 | 6.7 | 0.2 | 3.0 | 0.2 | 2.6 |
| 0.25 | 4.7 | 0.25 | 2.8 | 0.25 | 7.6 | 0.25 | 6.7 | 0.25 | 3.0 | 0.25 | 2.6 |
| 0.3 | 4.7 | 0.3 | 2.8 | 0.3 | 7.6 | 0.3 | 6.7 | 0.3 | 3.0 | 0.3 | 2.6 |

-continued

| MASSFRAC HF | Organics 0.2 F1234yf + 0.2 F245cb + 0.2 F1233zdE + 0.2 F1234zeE + 0.2 F1234zeZ TOTAL PRESSURE bar | MASSFRAC HF | Organics 0.96 F1234yf + 0.01 F245cb + 0.01 F1233zdE + 0.01 F1234zeE + 0.01 F1234zeZ TOTAL PRESSURE bar |
|---|---|---|---|
| 0.35 | 4.7 | 0.35 | 2.8 |
| 0.4 | 4.7 | 0.4 | 2.8 |
| 0.45 | 4.7 | 0.45 | 2.8 |
| 0.5 | 4.7 | 0.5 | 2.8 |
| 0.55 | 4.7 | 0.55 | 2.8 |
| 0.6 | 4.7 | 0.6 | 2.8 |
| 0.65 | 4.7 | 0.65 | 2.8 |
| 0.7 | 4.7 | 0.7 | 2.8 |
| 0.75 | 4.7 | 0.75 | 2.8 |
| 0.8 | 4.5 | 0.8 | 2.8 |
| 0.85 | 4.3 | 0.85 | 2.6 |
| 0.9 | 3.9 | 0.9 | 2.4 |
| 0.95 | 3.4 | 0.95 | 2.2 |
|  | 2.5 |  | 1.7 |
| 1 | 1.2 | 1 | 1.2 |

HF-HFO-1234yf-HFC-245cb-HFO-1234zeE-HFO-1234zeZ-HCFO-1233zdE

| MASSFRAC HF | Organics 0.96 F1234yf + 0.01 F245cb + 0.01 F1233zdE + 0.01 F1234zeE + 0.01 F1234zeZ TOTAL PRESSURE bar | MASSFRAC HF | Organics 0.01 F1234yf + 0.01 F245cb + 0.96 F1233zdE + 0.01 F1234zeE + 0.01 F1234zeZ TOTAL PRESSURE bar | MASSFRAC HF | Organics 0.01 F1234yf + 0.01 F245cb + 0.01 F1233zdE + 0.96 F1234zeE + 0.01 F1234zeZ TOTAL PRESSURE bar | MASSFRAC HF | Organics 0.01 F1234yf + 0.01 F245cb + 0.01 F1233zdE + 0.01 F1234zeE + 0.96 F1234zeZ TOTAL PRESSURE bar |
|---|---|---|---|---|---|---|---|
| 0 | 4.6 | 0 | 1.5 | 0 | 4.8 | 0 | 1.9 |
| 0.05 | 5.8 | 0.05 | 2.6 | 0.05 | 5.8 | 0.05 | 3.0 |
| 0.1 | 5.8 | 0.1 | 2.6 | 0.1 | 5.8 | 0.1 | 3.0 |
| 0.15 | 5.8 | 0.15 | 2.6 | 0.15 | 5.8 | 0.15 | 3.0 |
| 0.2 | 5.8 | 0.2 | 2.6 | 0.2 | 5.8 | 0.2 | 3.0 |
| 0.25 | 5.8 | 0.25 | 2.6 | 0.25 | 5.8 | 0.25 | 3.0 |
| 0.3 | 5.8 | 0.3 | 2.6 | 0.3 | 5.8 | 0.3 | 3.0 |
| 0.35 | 5.8 | 0.35 | 2.6 | 0.35 | 5.8 | 0.35 | 3.0 |
| 0.4 | 5.8 | 0.4 | 2.6 | 0.4 | 5.8 | 0.4 | 3.0 |
| 0.45 | 5.8 | 0.45 | 2.6 | 0.45 | 5.8 | 0.45 | 3.0 |
| 0.5 | 5.8 | 0.5 | 2.6 | 0.5 | 5.7 | 0.5 | 3.0 |
| 0.55 | 5.8 | 0.55 | 2.6 | 0.55 | 5.7 | 0.55 | 3.0 |
| 0.6 | 5.8 | 0.6 | 2.6 | 0.6 | 5.6 | 0.6 | 3.0 |
| 0.65 | 5.8 | 0.65 | 2.6 | 0.65 | 5.5 | 0.65 | 3.0 |
| 0.7 | 5.8 | 0.7 | 2.6 | 0.7 | 5.4 | 0.7 | 3.0 |
| 0.75 | 5.8 | 0.75 | 2.5 | 0.75 | 5.1 | 0.75 | 3.0 |
| 0.8 | 5.8 | 0.8 | 2.3 | 0.8 | 4.8 | 0.8 | 2.9 |
| 0.85 | 5.8 | 0.85 | 2.0 | 0.85 | 4.3 | 0.85 | 2.7 |
| 0.9 | 5.0 | 0.9 | 1.7 | 0.9 | 3.6 | 0.9 | 2.4 |
| 0.95 | 3.5 | 0.95 | 1.2 | 0.95 | 2.6 | 0.95 | 1.9 |
| 1 | 1.2 | 1 |  | 1 | 1.2 | 1 | 1.2 |

-continued

HF-HFO-1234yf-HFC-245cb-HFO-1234zeE-HCFO-1233zdE-HFO-1243zf

| Organics 0.2 F1234yf + 0.2 F245cb + 0.2 F1243zf + 0.2 F1234zeE + 0.2 F1233zdE | | Organics 0.96 F1234yf + 0.01 F245cb + 0.01 F1243zf + 0.01 F1234zeE + 0.01 F1233zdE | | Organics 0.01 F1234yf + 0.96 F245cb + 0.01 F1243zf + 0.01 F1234zeE + 0.01 F1233zdE | | Organics 0.01 F1234yf + 0.01 F245cb + 0.96 F1243zf + 0.01 F1234zeE + 0.01 F1233zdE | | Organics 0.01 F1234yf + 0.01 F245cb + 0.01 F1243zf + 0.96 F1234zeE + 0.01 F1233zdE | | Organics 0.01 F1234xf + 0.01 F245cb + 0.01 F1243zf + 0.01 F1234zeE + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 6.7 | 0 | 4.7 | 0 | 5.8 | 0 | 4.9 | 0 | 1.5 |
| 0.05 | 5.9 | 0.05 | 7.7 | 0.05 | 5.8 | 0.05 | 6.7 | 0.05 | 5.8 | 0.05 | 2.6 |
| 0.1 | 5.9 | 0.1 | 7.7 | 0.1 | 5.8 | 0.1 | 6.8 | 0.1 | 5.8 | 0.1 | 2.6 |
| 0.15 | 5.9 | 0.15 | 7.7 | 0.15 | 5.8 | 0.15 | 6.8 | 0.15 | 5.8 | 0.15 | 2.6 |
| 0.2 | 5.9 | 0.2 | 7.7 | 0.2 | 5.8 | 0.2 | 6.8 | 0.2 | 5.8 | 0.2 | 2.6 |
| 0.25 | 5.9 | 0.25 | 7.6 | 0.25 | 5.8 | 0.25 | 6.8 | 0.25 | 5.8 | 0.25 | 2.6 |
| 0.3 | 5.9 | 0.3 | 7.6 | 0.3 | 5.8 | 0.3 | 6.8 | 0.3 | 5.8 | 0.3 | 2.6 |
| 0.35 | 5.9 | 0.35 | 7.6 | 0.35 | 5.8 | 0.35 | 6.8 | 0.35 | 5.8 | 0.35 | 2.6 |
| 0.4 | 5.9 | 0.4 | 7.7 | 0.4 | 5.8 | 0.4 | 6.8 | 0.4 | 5.8 | 0.4 | 2.6 |
| 0.45 | 5.9 | 0.45 | 7.7 | 0.45 | 5.8 | 0.45 | 6.7 | 0.45 | 5.8 | 0.45 | 2.6 |
| 0.5 | 5.9 | 0.5 | 7.7 | 0.5 | 5.8 | 0.5 | 6.7 | 0.5 | 5.8 | 0.5 | 2.6 |
| 0.55 | 5.9 | 0.55 | 7.7 | 0.55 | 5.8 | 0.55 | 6.7 | 0.55 | 5.7 | 0.55 | 2.6 |
| 0.6 | 5.9 | 0.6 | 7.7 | 0.6 | 5.8 | 0.6 | 6.7 | 0.6 | 5.7 | 0.6 | 2.6 |
| 0.65 | 5.9 | 0.65 | 7.7 | 0.65 | 5.8 | 0.65 | 6.6 | 0.65 | 5.6 | 0.65 | 2.6 |
| 0.7 | 5.9 | 0.7 | 7.6 | 0.7 | 5.8 | 0.7 | 6.5 | 0.7 | 5.4 | 0.7 | 2.6 |
| 0.75 | 5.7 | 0.75 | 7.5 | 0.75 | 5.8 | 0.75 | 6.4 | 0.75 | 5.2 | 0.75 | 2.6 |
| 0.8 | 5.4 | 0.8 | 7.2 | 0.8 | 5.8 | 0.8 | 6.1 | 0.8 | 4.8 | 0.8 | 2.6 |
| 0.85 | 5.0 | 0.85 | 6.6 | 0.85 | 5.8 | 0.85 | 5.6 | 0.85 | 4.3 | 0.85 | 2.5 |
| 0.9 | 4.2 | 0.9 | 5.5 | 0.9 | 5.0 | 0.9 | 4.8 | 0.9 | 3.6 | 0.9 | 2.3 |
| 0.95 | 3.0 | 0.95 | 3.8 | 0.95 | 3.5 | 0.95 | 3.4 | 0.95 | 2.6 | 0.95 | 2.1 |
| 1 | 1.2 | 1 | 1.2 | 1 | 1.2 | 1 | 1.2 | 1 | 1.2 | 1 | 1.7 |

HF-HFO-1234yf-HFC-245cb-HFO-1234zeZ-HCFO-1233zdE-HFO-1243zf

| Organics 0.2 F1234yf + 0.2 F245cb + 0.2 F1243zf + 0.2 F1234zeZ + 0.2 F1233zdE | | Organics 0.96 F1234yf + 0.01 F245cb + 0.01 F1243zf + 0.01 F1234zeZ + 0.01 F1233zdE | | Organics 0.01 F1234yf + 0.96 F245cb + 0.01 F1243zf + 0.01 F1234zeZ + 0.01 F1233zdE | | Organics 0.01 F1234yf + 0.01 F245cb + 0.96 F1243zf + 0.01 F1234zeZ + 0.01 F1233zdE | | Organics 0.01 F1234yf + 0.01 F245cb + 0.01 F1243zf + 0.96 F1234zeZ + 0.01 F1233zdE | | Organics 0.01 F1234yf + 0.01 F245cb + 0.01 F1243zf + 0.01 F1234zeZ + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.2 | 0 | 6.7 | 0 | 4.6 | 0 | 5.8 | 0 | 1.9 | 0 | 1.5 |
| 0.05 | 5.3 | 0.05 | 7.6 | 0.05 | 5.8 | 0.05 | 6.7 | 0.05 | 3.0 | 0.05 | 2.6 |
| 0.1 | 5.3 | 0.1 | 7.6 | 0.1 | 5.8 | 0.1 | 6.7 | 0.1 | 3.0 | 0.1 | 2.6 |
| 0.15 | 5.3 | 0.15 | 7.6 | 0.15 | 5.8 | 0.15 | 6.7 | 0.15 | 3.0 | 0.15 | 2.6 |
| 0.2 | 5.3 | 0.2 | 7.6 | 0.2 | 5.8 | 0.2 | 6.7 | 0.2 | 3.0 | 0.2 | 2.6 |
| 0.25 | 5.3 | 0.25 | 7.6 | 0.25 | 5.8 | 0.25 | 6.7 | 0.25 | 3.0 | 0.25 | 2.6 |
| 0.3 | 5.3 | 0.3 | 7.6 | 0.3 | 5.8 | 0.3 | 6.7 | 0.3 | 3.0 | 0.3 | 2.6 |

-continued

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0.35 | 5.3 | 0.35 | 7.6 | 0.35 | 5.8 | 0.35 | 6.7 | 0.35 | 3.0 | 0.35 | 2.6 |
| 0.4 | 5.3 | 0.4 | 7.6 | 0.4 | 5.8 | 0.4 | 6.7 | 0.4 | 3.0 | 0.4 | 2.6 |
| 0.45 | 5.3 | 0.45 | 7.6 | 0.45 | 5.8 | 0.45 | 6.7 | 0.45 | 3.0 | 0.45 | 2.6 |
| 0.5 | 5.3 | 0.5 | 7.6 | 0.5 | 5.8 | 0.5 | 6.7 | 0.5 | 3.0 | 0.5 | 2.6 |
| 0.55 | 5.3 | 0.55 | 7.6 | 0.55 | 5.8 | 0.55 | 6.7 | 0.55 | 3.0 | 0.55 | 2.6 |
| 0.6 | 5.3 | 0.6 | 7.6 | 0.6 | 5.8 | 0.6 | 6.7 | 0.6 | 3.0 | 0.6 | 2.6 |
| 0.65 | 5.3 | 0.65 | 7.6 | 0.65 | 5.8 | 0.65 | 6.6 | 0.65 | 3.0 | 0.65 | 2.6 |
| 0.7 | 5.3 | 0.7 | 7.6 | 0.7 | 5.8 | 0.7 | 6.5 | 0.7 | 3.0 | 0.7 | 2.6 |
| 0.75 | 5.2 | 0.75 | 7.5 | 0.75 | 5.8 | 0.75 | 6.4 | 0.75 | 3.0 | 0.75 | 2.5 |
| 0.8 | 5.0 | 0.8 | 7.2 | 0.8 | 5.8 | 0.8 | 6.1 | 0.8 | 2.9 | 0.8 | 2.3 |
| 0.85 | 4.6 | 0.85 | 6.6 | 0.85 | 5.8 | 0.85 | 5.6 | 0.85 | 2.7 | 0.85 | 2.0 |
| 0.9 | 3.9 | 0.9 | 5.5 | 0.9 | 5.0 | 0.9 | 4.7 | 0.9 | 2.4 | 0.9 | 1.7 |
| 0.95 | 2.9 | 0.95 | 3.8 | 0.95 | 3.5 | 0.95 | 3.4 | 0.95 | 1.9 | 0.95 | 1.2 |
| 1 | 1.2 | 1 | 1.2 | 1 | 1.2 | 1 | 1.2 | 1 | 1.2 | 1 | 1.2 |
| Organics 0.2 F1234yf + 0.2 F1243zf + 0.2 F1233zdE + 0.2 F1234zeE + 0.2 F1234zeZ | | Organics 0.96 F1234yf + 0.01 F1243zf + 0.01 F1233zdE + 0.01 F1234zeE + 0.01 F1234zeZ | | | | | | | | | |

HF-HFO-1234yf-HFO-1234zeE-HFO-1234zeZ-HCFO-1233zdE-HFO-1243zf

| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|
| Organics 0.01 F1234yf + 0.96 F1243zf + 0.01 F1233zdE + 0.01 F1234zeE + 0.01 F1234zeZ | | Organics 0.01 F1234yf + 0.01 F1243zf + 0.96 F1233zdE + 0.01 F1234zeE + 0.01 F1234zeZ | | Organics 0.01 F1234yf + 0.01 F1243zf + 0.01 F1233zdE + 0.96 F1234zeE + 0.01 F1234zeZ | | Organics 0.01 F1234yf + 0.01 F1243xf + 0.01 F1233zdE + 0.01 F1234zeE + 0.96 F1234zeZ | |
| 0 | 5.8 | 0 | 1.5 | 0 | 4.8 | 0 | 1.9 |
| 0.05 | 6.7 | 0.05 | 2.6 | 0.05 | 5.8 | 0.05 | 3.0 |
| 0.1 | 7.6 | 0.1 | 2.6 | 0.1 | 5.8 | 0.1 | 3.0 |
| 0.15 | 7.6 | 0.15 | 2.6 | 0.15 | 5.8 | 0.15 | 3.0 |
| 0.2 | 7.6 | 0.2 | 2.6 | 0.2 | 5.8 | 0.2 | 3.0 |
| 0.25 | 7.6 | 0.25 | 2.6 | 0.25 | 5.8 | 0.25 | 3.0 |
| 0.3 | 7.6 | 0.3 | 2.6 | 0.3 | 5.8 | 0.3 | 3.0 |
| 0.35 | 7.6 | 0.35 | 2.6 | 0.35 | 5.8 | 0.35 | 3.0 |
| 0.4 | 7.6 | 0.4 | 2.6 | 0.4 | 5.8 | 0.4 | 3.0 |
| 0.45 | 7.6 | 0.45 | 2.6 | 0.45 | 5.8 | 0.45 | 3.0 |
| 0.5 | 7.6 | 0.5 | 2.6 | 0.5 | 5.8 | 0.5 | 3.0 |
| 0.55 | 7.6 | 0.55 | 2.6 | 0.55 | 5.7 | 0.55 | 3.0 |
| 0.6 | 7.6 | 0.6 | 2.6 | 0.6 | 5.6 | 0.6 | 3.0 |
| 0.65 | 7.6 | 0.65 | 2.6 | 0.65 | 5.5 | 0.65 | 3.0 |
| 0.7 | 7.6 | 0.7 | 2.6 | 0.7 | 5.4 | 0.7 | 3.0 |
| 0.75 | 7.5 | 0.75 | 2.6 | 0.75 | 5.1 | 0.75 | 3.0 |
| 0.8 | 7.1 | 0.8 | 2.5 | 0.8 | 4.8 | 0.8 | 2.9 |
| 0.85 | 6.5 | 0.85 | 2.3 | 0.85 | 4.3 | 0.85 | 2.7 |
| 0.9 | 5.5 | 0.9 | 2.0 | 0.9 | 3.6 | 0.9 | 2.4 |
| 0.95 | 3.8 | 0.95 | 1.7 | 0.95 | 2.6 | 0.95 | 1.9 |
| 1 | 1.2 | 1 | 1.2 | 1 | 1.2 | 1 | 1.2 |

Example 14: Temperature and Pressure Range of Systems with 6 Compounds

|  | Boiling point range | |
|---|---|---|
| System with 6 compounds | Temperature ° C. | Pressure bar abs |
| HF-HCFO-1233xf-HFC-245cb-HFO-1234zeE-HFO-1234zeZ-HCFO-1233zdE | 0 to 40 | ~0.9 to ~9.0 |
| HF-HCFO-1233xf-HFC-245cb-HFO-1234zeE-HCFO-1233zdE-HFO-1243zf | 0 to 40 | ~0.9 to ~10.3 |
| HF-HCFO-1233xf-HFC-245cb-HFO-1234zeZ-HCFO-1233zdE-HFO-1243zf | 0 to 40 | ~1.0 to ~10.3 |
| HF-HCFO-1233xf-HFO-1234zeE-HFO-1234zeZ-HCFO-1233zdE-HFO-1243zf | 0 to 40 | ~0.9 to ~10.3 |
| HF-HFC-245cb-HFO-1234zeE-HFO-1234zeZ-HCFO-1233zdE-HFO-1243zf | 0 to 40 | ~0.9 to ~10.3 |
| HF-HCFO-1233xf-HFO-1234yf-HFC-245cb-HFO-1234zeE-HCFO-1233zdE | 0 to 40 | ~0.9 to ~11.6 |
| HF-HCFO-1233xf-HFO-1234yf-HFC-245cb-HFO-1234zeZ-HCFO-1233zdE | 0 to 40 | ~0.9 to ~11.5 |
| HF-HCFO-1233xf-HFO-1234yf-HFC-245cb-HCFO-1233zdE-HFO-1243zf | 0 to 40 | ~0.9 to ~11.6 |
| HF-HCFO-1233xf-HFO-1234yf-HFO-1234zeE-HFO-1234zeZ-HCFO-1233zdE | 0 to 40 | ~0.9 to ~11.5 |
| HF-HFCO-1233xf-HFO-1234yf-HFO-1234zeE-HCFO-1233zdE-HFO-1243zf | 0 to 40 | ~0.9 to ~11.6 |
| HF-HCFO-1233xf-HFO-1234yf-HFO-1234zeZ-HCFO-1233zdE-HFO-1243zf | 0 to 40 | ~0.9 to ~11.6 |
| HF-HFO-1234yf-HFC-245cb-HFO-1234zeE-HFO-1234zeZ-HCFO-1233zdE | 0 to 40 | ~0.9 to ~11.6 |
| HF-HFO-1234yf-HFC-245cb-HFO-1234zeE-HCFO-1233zdE-HFO-1243zf | 0 to 40 | ~1.0 to ~11.7 |
| HF-HFO-1234yf-HFC-245cb-HFO-1234zeZ-HCFO-1233zdE-HFO-1243zf | 0 to 40 | ~0.9 to ~11.6 |
| HF-HFO-1234yf-HFO-1234zeE-HFO-1234zeZ-HCFO-1233zdE-HFO-1243zf | 0 to 40 | ~0.9 to ~11.6 |

Example 15: Decantation Range of Systems with 6 Compounds

|  | Decantation ranges Mass percentage of HF | | |
|---|---|---|---|
| System with 6 compounds | Isotherm 0° C. | Isotherm 25° C. | Isotherm 40° C. |
| HF-HCFO-1233xf-HFC-245cb-HFO-1234zeE-HFO-1234zeZ-HCFO-1233zdE | 5-75 | 5-70 | 10-65 |
| HF-HCFO-1233xf-HFC-245cb-HFO-1234zeE-HCFO-1233zdE-HFO-1243zf | 5-75 | 5-70 | 15-50 |
| HF-HCFO-1233xf-HFC-245cb-HFO-1234zeZ-HCFO-1233zdE-HFO-1243zf | 5-75 | 5-70 | 10-65 |
| HF-HCFO-1233xf-HFO-1234zeE-HFO-1234zeZ-HCFO-1233zdE-HFO-1243zf | 5-75 | 5-65 | 10-55 |
| HF-HFC-245cb-HFO-1234zeE-HFO-1234zeZ-HCFO-1233zdE-HFO-1243zf | 5-75 | 5-70 | 15-50 |
| HF-HCFO-1233xf-HFO-1234yf-HFC-245cb-HFO-1234zeE-HCFO-1233zdE | 5-75 | 5-70 | 15-55 |
| HF-HCFO-1233xf-HFO-1234yf-HFC-245cb-HFO-1234zeZ-HCFO-1233zdE | 5-75 | 5-75 | 10-65 |
| HF-HCFO-1233xf-HFO-1234yf-HFC-245cb-HCFO-1233zdE-HFO-1243zf | 5-75 | 5-70 | 15-55 |
| HF-HCFO-1233xf-HFO-1234yf-HFO-1234zeE-HFO-1234zeZ-HCFO-1233zdE | 5-75 | 5-65 | 10-55 |
| HF-HFCO-1233xf-HFO-1234yf-HFO-1234zeE-HCFO-1233zdE-HFO-1243zf | 5-70 | 10-75 | * |
| HF-HCFO-1233xf-HFO-1234yf-HFO-1234zeZ-HCFO-1233zdE-HFO-1243zf | 5-75 | 5-70 | 10-55 |
| HF-HFO-1234yf-HFC-245cb-HFO-1234zeE-HFO-1234zeZ-HCFO-1233zdE | 5-75 | 5-70 | 15-55 |
| HF-HFO-1234yf-HFC-245cb-HFO-1234zeE-HCFO-1233zdE-HFO-1243zf | 5-75 | 10-65 | * |

-continued

| | Decantation ranges Mass percentage of HF | | |
|---|---|---|---|
| System with 6 compounds | Isotherm 0° C. | Isotherm 25° C. | Isotherm 40° C. |
| HF-HFO-1234yf-HFC-245cb-HFO-1234zeZ-HCFO-1233zdE-HFO-1243zf | 5-75 | 10-70 | 15-55 |
| HF-HFO-1234yf-HFO-1234zeE-HFO-1234zeZ-HCFO-1233zdE-HFO-1243zf | 5-70 | 10-65 | * |

Example 16: Systems with Seven Compounds, Isotherm at 25° C.

| MASSFRAC HF | Organics 0.15 F1233xf + 0.17 F245cb + 0.17 F1233zdE + 0.17 F1234zeE + 0.17 F1243zf — TOTAL PRESSURE bar | MASSFRAC HF | Organics 0.95 F1233xf + 0.01 F245cb + 0.01 F1233zdE + 0.01 F1234zeE + 0.01 F1243zf — TOTAL PRESSURE bar | MASSFRAC HF | Organics 0.01 F1233xf + 0.95 F245cb + 0.01 F1233zdE + 0.01 F1234zeE + 0.01 F1243zf — TOTAL PRESSURE bar | MASSFRAC HF | Organics 0.01 F1233xf + 0.01 F245cb + 0.95 F1233zdE + 0.01 F1234zeE + 0.01 F1243zf — TOTAL PRESSURE bar | MASSFRAC HF | Organics 0.01 F1233xf + 0.01 F245cb + 0.01 F1233zdE + 0.95 F1234zeE + 0.01 F1243zf — TOTAL PRESSURE bar | MASSFRAC HF | Organics 0.01 F1233xf + 0.01 F245cb + 0.01 F1233zdE + 0.01 F1234zeE + 0.95 F1243zf — TOTAL PRESSURE bar | MASSFRAC HF | Organics 0.01 F1233xf + 0.01 F245cb + 0.01 F1233zdE + 0.01 F1234zeE + 0.95 F1243zf — TOTAL PRESSURE bar |
|---|---|---|---|---|---|---|---|---|---|---|---|
| 0 | 3.5 | 0 | 1.7 | 0 | 4.6 | 0 | 1.5 | 0 | 4.8 | 0 | 1.9 |
| 0.05 | 4.6 | 0.05 | 2.8 | 0.05 | 5.7 | 0.05 | 2.6 | 0.05 | 5.7 | 0.05 | 3.0 |
| 0.1 | 4.6 | 0.1 | 2.8 | 0.1 | 5.7 | 0.1 | 2.6 | 0.1 | 5.8 | 0.1 | 3.0 |
| 0.15 | 4.6 | 0.15 | 2.8 | 0.15 | 5.7 | 0.15 | 2.6 | 0.15 | 5.8 | 0.15 | 3.0 |
| 0.2 | 4.6 | 0.2 | 2.8 | 0.2 | 5.7 | 0.2 | 2.6 | 0.2 | 5.8 | 0.2 | 3.0 |
| 0.25 | 4.6 | 0.25 | 2.8 | 0.25 | 5.8 | 0.25 | 2.6 | 0.25 | 5.8 | 0.25 | 3.0 |
| 0.3 | 4.6 | 0.3 | 2.8 | 0.3 | 5.8 | 0.3 | 2.6 | 0.3 | 5.8 | 0.3 | 3.0 |
| 0.35 | 4.6 | 0.35 | 2.8 | 0.35 | 5.8 | 0.35 | 2.6 | 0.35 | 5.8 | 0.35 | 3.0 |
| 0.4 | 4.6 | 0.4 | 2.8 | 0.4 | 5.8 | 0.4 | 2.6 | 0.4 | 5.8 | 0.4 | 3.0 |
| 0.45 | 4.6 | 0.45 | 2.8 | 0.45 | 5.8 | 0.45 | 2.6 | 0.45 | 5.7 | 0.45 | 3.0 |
| 0.5 | 4.6 | 0.5 | 2.8 | 0.5 | 5.8 | 0.5 | 2.6 | 0.5 | 5.7 | 0.5 | 3.0 |
| 0.55 | 4.6 | 0.55 | 2.8 | 0.55 | 5.8 | 0.55 | 2.6 | 0.55 | 5.7 | 0.55 | 3.0 |
| 0.6 | 4.6 | 0.6 | 2.8 | 0.6 | 5.8 | 0.6 | 2.6 | 0.6 | 5.6 | 0.6 | 3.0 |
| 0.65 | 4.6 | 0.65 | 2.8 | 0.65 | 5.8 | 0.65 | 2.6 | 0.65 | 5.5 | 0.65 | 3.0 |
| 0.7 | 4.6 | 0.7 | 2.8 | 0.7 | 5.8 | 0.7 | 2.6 | 0.7 | 5.3 | 0.7 | 3.0 |
| 0.75 | 4.5 | 0.75 | 2.8 | 0.75 | 5.8 | 0.75 | 2.6 | 0.75 | 5.1 | 0.75 | 3.0 |
| 0.8 | 4.2 | 0.8 | 2.6 | 0.8 | 5.8 | 0.8 | 2.4 | 0.8 | 4.8 | 0.8 | 2.9 |
| 0.85 | 3.9 | 0.85 | 2.4 | 0.85 | 5.8 | 0.85 | 2.3 | 0.85 | 4.3 | 0.85 | 2.7 |
| 0.9 | 3.3 | 0.9 | 2.2 | 0.9 | 4.9 | 0.9 | 2.0 | 0.9 | 3.6 | 0.9 | 2.4 |
| 0.95 | 2.5 | 0.95 | 1.8 | 0.95 | 3.5 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HCFO-1233zdE-HFO-1234zeE-HFO-1234zf

| MASSFRAC HF | Organics 0.15 F1233xf + 0.17 F1234yf + 0.17 F245cb + 0.17 F1233zdE + 0.17 F1234zeE + F1234zf — TOTAL PRESSURE bar | MASSFRAC HF | Organics 0.01 F1233xf + 0.95 F1234yf + 0.01 F245cb + 0.01 F1233zdE + 0.01 F1234zeE + F1234zf — TOTAL PRESSURE bar | MASSFRAC HF | Organics 0.01 F1233xf + 0.01 F1234yf + 0.95 F245cb + 0.01 F1233zdE + 0.01 F1234zeE + F1234zf — TOTAL PRESSURE bar | MASSFRAC HF | Organics 0.01 F1233xf + 0.01 F1234yf + 0.01 F245cb + 0.95 F1233zdE + 0.01 F1234zeE + F1234zf — TOTAL PRESSURE bar | MASSFRAC HF | Organics 0.01 F1233xf + 0.01 F1234yf + 0.01 F245cb + 0.01 F1233zdE + 0.95 F1234zeE + F1234zf — TOTAL PRESSURE bar | MASSFRAC HF | Organics 0.95 F1233xf + 0.01 F1234yf + 0.01 F245cb + 0.01 F1233zdE + 0.01 F1234zeE + F1234zf — TOTAL PRESSURE bar |
|---|---|---|---|---|---|---|---|---|---|---|---|
| 0 | 3.6 | 0 | 6.6 | 0 | 4.6 | 0 | 1.5 | 0 | 4.8 | 0 | 1.7 |
| 0.05 | 4.7 | 0.05 | 7.6 | 0.05 | 5.8 | 0.05 | 2.6 | 0.05 | 5.8 | 0.05 | 2.8 |
| 0.1 | 4.7 | 0.1 | 7.6 | 0.1 | 5.8 | 0.1 | 2.6 | 0.1 | 5.8 | 0.1 | 2.8 |
| 0.15 | 4.7 | 0.15 | 7.6 | 0.15 | 5.8 | 0.15 | 2.6 | 0.15 | 5.8 | 0.15 | 2.8 |
| 0.2 | 4.7 | 0.2 | 7.6 | 0.2 | 5.8 | 0.2 | 2.6 | 0.2 | 5.8 | 0.2 | 2.8 |

-continued

| MASSFRAC HF | Organics 0.15 F1233xf + 0.17 F1234yf + 0.17 F245cb + 0.17 F1233zdE + 0.17 F1234zeE + 0.17 F1243zf TOTAL PRESSURE bar | MASSFRAC HF | Organics 0.01 F1233xf + 0.95 F1234yf + 0.01 F245cb + 0.01 F1233zdE + 0.01 F1234zeE + 0.01 F1243zf TOTAL PRESSURE bar | MASSFRAC HF | Organics 0.01 F1233xf + 0.01 F1234yf + 0.95 F245cb + 0.01 F1233zdE + 0.01 F1234zeE + 0.01 F1243zf TOTAL PRESSURE bar | MASSFRAC HF | Organics 0.01 F1233xf + 0.01 F1234yf + 0.01 F245cb + 0.95 F1233zdE + 0.01 F1234zeE + 0.01 F1243zf TOTAL PRESSURE bar | MASSFRAC HF | Organics 0.01 F1233xf + 0.01 F1234yf + 0.01 F245cb + 0.01 F1233zdE + 0.95 F1234zeE + 0.01 F1243zf TOTAL PRESSURE bar | MASSFRAC HF | Organics 0.01 F1233xf + 0.01 F1234yf + 0.01 F245cb + 0.01 F1233zdE + 0.01 F1234zeE + 0.95 F1243zf TOTAL PRESSURE bar |
|---|---|---|---|---|---|---|---|---|---|---|---|
| 0 | 4.4 | 0 | 6.6 | 0 | 4.6 | 0 | 1.5 | 0 | 4.8 | 0 | 1.7 |
| 0.05 | 5.4 | 0.05 | 7.6 | 0.05 | 5.8 | 0.05 | 2.6 | 0.05 | 5.8 | 0.05 | 2.8 |
| 0.1 | 5.4 | 0.1 | 7.6 | 0.1 | 5.8 | 0.1 | 2.6 | 0.1 | 6.7 | 0.1 | 2.8 |
| 0.15 | 5.4 | 0.15 | 7.6 | 0.15 | 5.8 | 0.15 | 2.6 | 0.15 | 6.7 | 0.15 | 2.8 |
| 0.2 | 5.4 | 0.2 | 7.6 | 0.2 | 5.8 | 0.2 | 2.6 | 0.2 | 6.7 | 0.2 | 2.8 |
| 0.25 | 5.4 | 0.25 | 7.6 | 0.25 | 5.8 | 0.25 | 2.6 | 0.25 | 6.7 | 0.25 | 2.8 |
| 0.3 | 5.4 | 0.3 | 7.6 | 0.3 | 5.8 | 0.3 | 2.6 | 0.3 | 6.7 | 0.3 | 2.8 |
| 0.35 | 5.4 | 0.35 | 7.6 | 0.35 | 5.8 | 0.35 | 2.6 | 0.35 | 6.7 | 0.35 | 2.8 |
| 0.4 | 5.4 | 0.4 | 7.6 | 0.4 | 5.8 | 0.4 | 2.6 | 0.4 | 6.7 | 0.4 | 2.8 |
| 0.45 | 5.4 | 0.45 | 7.6 | 0.45 | 5.8 | 0.45 | 2.6 | 0.45 | 6.7 | 0.45 | 2.8 |
| 0.5 | 5.4 | 0.5 | 7.6 | 0.5 | 5.8 | 0.5 | 2.6 | 0.5 | 6.7 | 0.5 | 2.8 |
| 0.55 | 5.4 | 0.55 | 7.6 | 0.55 | 5.8 | 0.55 | 2.6 | 0.55 | 6.7 | 0.55 | 2.8 |
| 0.6 | 5.4 | 0.6 | 7.6 | 0.6 | 5.8 | 0.6 | 2.6 | 0.6 | 6.6 | 0.6 | 2.8 |
| 0.65 | 5.4 | 0.65 | 7.6 | 0.65 | 5.8 | 0.65 | 2.6 | 0.65 | 6.5 | 0.65 | 2.8 |
| 0.7 | 5.4 | 0.7 | 7.6 | 0.7 | 5.8 | 0.7 | 2.6 | 0.7 | 6.3 | 0.7 | 2.8 |
| 0.75 | 5.3 | 0.75 | 7.4 | 0.75 | 5.8 | 0.75 | 2.6 | 0.75 | 6.1 | 0.75 | 2.8 |
| 0.8 | 5.0 | 0.8 | 7.1 | 0.8 | 5.8 | 0.8 | 2.5 | 0.8 | 5.6 | 0.8 | 2.7 |
| 0.85 | 4.6 | 0.85 | 6.5 | 0.85 | 5.8 | 0.85 | 2.3 | 0.85 | 5.0 | 0.85 | 2.5 |
| 0.9 | 3.9 | 0.9 | 5.5 | 0.9 | 5.0 | 0.9 | 2.1 | 0.9 | 4.7 | 0.9 | 2.2 |
| 0.95 | 2.8 | 0.95 | 3.8 | 0.95 | 3.5 | 0.95 | 1.7 | 0.95 | 3.4 | 0.95 | 1.8 |
| 1 | 1.2 | 1 | 1.2 | 1 | 1.2 | 1 | 1.2 | 1 | 1.2 | 1 | 1.2 |

HF—HCFO-1233xf—HFO-1234yf—HFC-245cb—HCFO-1233zdE—HFO-1234zeE—HFO-1243zf

-continued

| MASSFRAC HF | Organics 0.15 F1233xf + 0.17 F1234yf + 0.17 F1233zdE + 0.17 F1243zf + 0.17 F1234zeE + 0.17 F1234zeZ — TOTAL PRESSURE bar | MASSFRAC HF | Organics 0.01 F1233xf + 0.95 F1234yf + 0.01 F1233zdE + 0.01 F1243zf + 0.01 F1234zeE + 0.01 F1234zeZ — TOTAL PRESSURE bar | MASSFRAC HF | Organics 0.01 F1233xf + 0.01 F1234yf + 0.95 F1233zdE + 0.01 F1243zf + 0.01 F1234zeE + 0.01 F1234zeZ — TOTAL PRESSURE bar | MASSFRAC HF | Organics 0.01 F1233xf + 0.01 F1234yf + 0.01 F1233zdE + 0.95 F1243zf + 0.01 F1234zeE + 0.01 F1234zeZ — TOTAL PRESSURE bar | MASSFRAC HF | Organics 0.01 F1233xf + 0.01 F1234yf + 0.01 F1233zdE + 0.01 F1243zf + 0.95 F1234zeE + 0.01 F1234zeZ — TOTAL PRESSURE bar | MASSFRAC HF | Organics 0.95 F1233xf + 0.01 F1234yf + 0.01 F1233zdE + 0.01 F1243zf + 0.01 F1234zeE + 0.01 F1234zeZ — TOTAL PRESSURE bar |
|---|---|---|---|---|---|---|---|---|---|---|---|
| \multicolumn{12}{c}{HF-HCFO-1233xf-HFO-1234yf-HFC-245cb-HCFO-1233zdE-HFO-1234zeZ-HFO-1234zf} | | | | | | | | | | | |
| 0 | 3.8 | 0 | 6.6 | 0 | 4.6 | 0 | 5.7 | 0 | 1.5 | 0 | 1.7 |
| 0.05 | 4.9 | 0.05 | 7.6 | 0.05 | 5.8 | 0.05 | 6.7 | 0.05 | 2.6 | 0.05 | 2.8 |
| 0.1 | 4.9 | 0.1 | 7.6 | 0.1 | 5.8 | 0.1 | 6.7 | 0.1 | 2.6 | 0.1 | 2.8 |
| 0.15 | 4.9 | 0.15 | 7.6 | 0.15 | 5.8 | 0.15 | 6.7 | 0.15 | 2.6 | 0.15 | 2.8 |
| 0.2 | 4.9 | 0.2 | 7.6 | 0.2 | 5.8 | 0.2 | 6.7 | 0.2 | 2.6 | 0.2 | 2.8 |
| 0.25 | 4.9 | 0.25 | 7.6 | 0.25 | 5.8 | 0.25 | 6.7 | 0.25 | 2.6 | 0.25 | 2.8 |
| 0.3 | 4.9 | 0.3 | 7.6 | 0.3 | 5.8 | 0.3 | 6.7 | 0.3 | 2.6 | 0.3 | 2.8 |
| 0.35 | 4.9 | 0.35 | 7.6 | 0.35 | 5.8 | 0.35 | 6.7 | 0.35 | 2.6 | 0.35 | 2.8 |
| 0.4 | 4.9 | 0.4 | 7.6 | 0.4 | 5.8 | 0.4 | 6.7 | 0.4 | 2.6 | 0.4 | 2.8 |
| 0.45 | 4.9 | 0.45 | 7.6 | 0.45 | 5.8 | 0.45 | 6.7 | 0.45 | 2.6 | 0.45 | 2.8 |
| 0.5 | 4.9 | 0.5 | 7.6 | 0.5 | 5.8 | 0.5 | 6.7 | 0.5 | 2.6 | 0.5 | 2.8 |
| 0.55 | 4.9 | 0.55 | 7.6 | 0.55 | 5.8 | 0.55 | 6.7 | 0.55 | 2.6 | 0.55 | 2.8 |
| 0.6 | 4.9 | 0.6 | 7.6 | 0.6 | 5.8 | 0.6 | 6.6 | 0.6 | 2.6 | 0.6 | 2.8 |
| 0.65 | 4.9 | 0.65 | 7.6 | 0.65 | 5.8 | 0.65 | 6.6 | 0.65 | 2.6 | 0.65 | 2.8 |
| 0.7 | 4.9 | 0.7 | 7.6 | 0.7 | 5.8 | 0.7 | 6.5 | 0.7 | 2.6 | 0.7 | 2.8 |
| 0.75 | 4.9 | 0.75 | 7.4 | 0.75 | 5.8 | 0.75 | 6.3 | 0.75 | 2.6 | 0.75 | 2.8 |
| 0.8 | 4.7 | 0.8 | 7.1 | 0.8 | 5.8 | 0.8 | 6.0 | 0.8 | 2.6 | 0.8 | 2.8 |
| 0.85 | 4.3 | 0.85 | 6.5 | 0.85 | 5.8 | 0.85 | 5.5 | 0.85 | 2.5 | 0.85 | 2.7 |
| 0.9 | 3.7 | 0.9 | 5.5 | 0.9 | 5.0 | 0.9 | 4.7 | 0.9 | 2.3 | 0.9 | 2.5 |
| 0.95 | 2.7 | 0.95 | 3.8 | 0.95 | 3.5 | 0.95 | 3.3 | 0.95 | 2.0 | 0.95 | 2.2 |
| 1 | 1.2 | 1 | 1.2 | 1 | 1.2 | 1 | 1.2 | 1 | 1.7 | 1 | 1.8 |
| | | | | | | | | | | 1 | 1.2 |
| \multicolumn{12}{c}{HF-HCFO-1233xf-HFO-1234yf-HCFO-1233zdE-HFO-1234zeE-HFO-1243zf} | | | | | | | | | | | |
| 0 | 3.9 | 0 | 6.6 | 0 | 1.5 | 0 | 5.7 | 0 | 4.8 | 0 | 1.7 |
| 0.05 | 5.0 | 0.05 | 7.6 | 0.05 | 2.6 | 0.05 | 6.7 | 0.05 | 5.8 | 0.05 | 2.8 |
| 0.1 | 4.9 | 0.1 | 7.6 | 0.1 | 2.6 | 0.1 | 6.7 | 0.1 | 5.8 | 0.1 | 2.8 |
| 0.15 | 4.9 | 0.15 | 7.6 | 0.15 | 2.6 | 0.15 | 6.7 | 0.15 | 5.8 | 0.15 | 2.8 |
| 0.2 | 4.9 | 0.2 | 7.6 | 0.2 | 2.6 | 0.2 | 6.7 | 0.2 | 5.8 | 0.2 | 2.8 |

-continued

| MASSFRAC HF | Organics 0.15 F1234yf + 0.17 F245cb + 0.17 F1233zdE + 0.17 F1234zeE + 0.17 F1243zf TOTAL PRESSURE bar | MASSFRAC HF | Organics 0.95 F1234yf + 0.01 F245cb + 0.01 F1233zdE + 0.01 F1234zeE + 0.01 F1243zf TOTAL PRESSURE bar | MASSFRAC HF | Organics 0.01 F1234yf + 0.95 F245cb + 0.01 F1233zdE + 0.01 F1234zeE + 0.01 F1243zf TOTAL PRESSURE bar | MASSFRAC HF | Organics 0.01 F1234yf + 0.01 F245cb + 0.95 F1233zdE + 0.01 F1234zeE + 0.01 F1243zf TOTAL PRESSURE bar | MASSFRAC HF | Organics 0.01 F1234yf + 0.01 F245cb + 0.01 F1233zdE + 0.95 F1234zeE + 0.01 F1243zf TOTAL PRESSURE bar | MASSFRAC HF | Organics 0.01 F1234yf + 0.01 F245cb + 0.01 F1233zdE + 0.01 F1234zeE + 0.95 F1243zf TOTAL PRESSURE bar |
|---|---|---|---|---|---|---|---|---|---|---|---|
| 0.25 | 4.9 | 0.25 | 7.6 | 0.25 | 2.6 | 0.25 | 6.7 | 0.25 | 5.8 | 0.25 | 2.8 |
| 0.3 | 4.9 | 0.3 | 7.6 | 0.3 | 2.6 | 0.3 | 6.7 | 0.3 | 5.8 | 0.3 | 2.8 |
| 0.35 | 4.9 | 0.35 | 7.6 | 0.35 | 2.6 | 0.35 | 6.7 | 0.35 | 5.8 | 0.35 | 2.8 |
| 0.4 | 4.9 | 0.4 | 7.6 | 0.4 | 2.6 | 0.4 | 6.7 | 0.4 | 5.8 | 0.4 | 2.8 |
| 0.45 | 4.9 | 0.45 | 7.6 | 0.45 | 2.6 | 0.45 | 6.7 | 0.45 | 5.8 | 0.45 | 2.8 |
| 0.5 | 4.9 | 0.5 | 7.6 | 0.5 | 2.6 | 0.5 | 6.7 | 0.5 | 5.7 | 0.5 | 2.8 |
| 0.55 | 4.9 | 0.55 | 7.6 | 0.55 | 2.6 | 0.55 | 6.7 | 0.55 | 5.7 | 0.55 | 2.8 |
| 0.6 | 4.9 | 0.6 | 7.6 | 0.6 | 2.6 | 0.6 | 6.6 | 0.6 | 5.6 | 0.6 | 2.8 |
| 0.65 | 4.9 | 0.65 | 7.6 | 0.65 | 2.6 | 0.65 | 6.5 | 0.65 | 5.5 | 0.65 | 2.8 |
| 0.7 | 4.8 | 0.7 | 7.6 | 0.7 | 2.6 | 0.7 | 6.3 | 0.7 | 5.3 | 0.7 | 2.8 |
| 0.75 | 4.7 | 0.75 | 7.4 | 0.75 | 2.6 | 0.75 | 6.0 | 0.75 | 5.1 | 0.75 | 2.8 |
| 0.8 | 4.4 | 0.8 | 7.1 | 0.8 | 2.5 | 0.8 | 6.0 | 0.8 | 4.8 | 0.8 | 2.6 |
| 0.85 | 4.0 | 0.85 | 6.5 | 0.85 | 2.3 | 0.85 | 5.5 | 0.85 | 4.3 | 0.85 | 2.5 |
| 0.9 | 3.4 | 0.9 | 5.5 | 0.9 | 2.0 | 0.9 | 4.7 | 0.9 | 3.6 | 0.9 | 2.2 |
| 0.95 | 2.5 | 0.95 | 3.8 | 0.95 | 1.7 | 0.95 | 3.3 | 0.95 | 2.6 | 0.95 | 1.8 |
| 1 | 1.2 | 1 | 1.2 | 1 | 1.2 | 1 | 1.2 | 1 | 1.2 | 1 | 1.2 |

HF-HFO-1234yf-HFC-245cb-HCFO-1233zdE-HFO-1234zeE-HFO-1243zf

| MASSFRAC HF | Organics 0.01 F1234yf + 0.95 F245cb + 0.01 F1233zdE + 0.01 F1234zeE + 0.01 F1243zf TOTAL PRESSURE bar | MASSFRAC HF | Organics 0.01 F1234yf + 0.01 F245cb + 0.95 F1233zdE + 0.01 F1234zeE + 0.01 F1243zf TOTAL PRESSURE bar | MASSFRAC HF | Organics 0.01 F1234yf + 0.01 F245cb + 0.01 F1233zdE + 0.95 F1234zeE + 0.01 F1243zf TOTAL PRESSURE bar | MASSFRAC HF | Organics 0.01 F1234yf + 0.01 F245cb + 0.01 F1233zdE + 0.01 F1234zeE + 0.95 F1243zf TOTAL PRESSURE bar | MASSFRAC HF | Organics 0.01 F1234yf + 0.01 F245cb + 0.01 F1233zdE + 0.01 F1234zeE + 0.01 F1243zf TOTAL PRESSURE bar |
|---|---|---|---|---|---|---|---|---|---|
| 0 | 4.6 | 0 | 1.5 | 0 | 4.8 | 0 | 5.8 | 0 | 2.0 |
| 0.05 | 5.8 | 0.05 | 2.6 | 0.05 | 5.8 | 0.05 | 6.7 | 0.05 | 3.1 |
| 0.1 | 5.8 | 0.1 | 2.6 | 0.1 | 5.8 | 0.1 | 6.7 | 0.1 | 3.1 |
| 0.15 | 5.8 | 0.15 | 2.6 | 0.15 | 5.8 | 0.15 | 6.7 | 0.15 | 3.1 |
| 0.2 | 5.8 | 0.2 | 2.6 | 0.2 | 5.8 | 0.2 | 6.7 | 0.2 | 3.1 |
| 0.25 | 5.8 | 0.25 | 2.6 | 0.25 | 5.8 | 0.25 | 6.7 | 0.25 | 3.1 |
| 0.3 | 5.8 | 0.3 | 2.6 | 0.3 | 5.8 | 0.3 | 6.7 | 0.3 | 3.1 |
| 0.35 | 5.8 | 0.35 | 2.6 | 0.35 | 5.8 | 0.35 | 6.7 | 0.35 | 3.1 |
| 0.4 | 5.8 | 0.4 | 2.6 | 0.4 | 5.8 | 0.4 | 6.7 | 0.4 | 3.1 |
| 0.45 | 5.8 | 0.45 | 2.6 | 0.45 | 5.8 | 0.45 | 6.7 | 0.45 | 3.1 |
| 0.5 | 5.8 | 0.5 | 2.6 | 0.5 | 5.8 | 0.5 | 6.7 | 0.5 | 3.1 |
| 0.55 | 5.8 | 0.55 | 2.6 | 0.55 | 5.7 | 0.55 | 6.7 | 0.55 | 3.1 |
| 0.6 | 5.8 | 0.6 | 2.6 | 0.6 | 5.6 | 0.6 | 6.6 | 0.6 | 3.1 |
| 0.65 | 5.8 | 0.65 | 2.6 | 0.65 | 5.5 | 0.65 | 6.5 | 0.65 | 3.1 |
| 0.7 | 5.8 | 0.7 | 2.6 | 0.7 | 5.4 | 0.7 | 6.3 | 0.7 | 3.1 |
| 0.75 | 5.8 | 0.75 | 2.6 | 0.75 | 5.1 | 0.75 | 6.1 | 0.75 | 3.1 |
| 0.8 | 5.8 | 0.8 | 2.5 | 0.8 | 4.8 | 0.8 | 5.6 | 0.8 | 2.9 |
| 0.85 | 5.8 | 0.85 | 2.3 | 0.85 | 4.3 | 0.85 | 4.7 | 0.85 | 2.7 |
| 0.9 | 5.0 | 0.9 | 2.1 | 0.9 | 3.6 | 0.9 | 3.4 | 0.9 | 2.4 |
| 0.95 | 3.5 | 0.95 | 1.7 | 0.95 | 2.6 | 0.95 | — | 0.95 | 1.9 |
| 1 | 1.2 | 1 | 1.2 | 1 | 1.2 | 1 | 1.2 | 1 | 1.2 |

-continued

| | HF-HCFC-1233zdE-HCFC-244bb-HFC-245fa-Trifluoropropyne-HFO-1225yeZ-HFO-1225zc | | | | | |
|---|---|---|---|---|---|---|
| MASSFRAC HF | Organics 0.15 F1233zdE + 0.17 F244bb + 0.17 F245fa + 0.17TFP + 0.17 F1225yeZ + 0.17 F1225zc TOTAL PRES bar | Organics 0.95 F1233zdE + 0.01 F244bb + 0.01 F245fa + 0.01 TFP + 0.01 F1225yeZ + 0.01 F1225zc TOTAL PRES bar | Organics 0.01 F1233zdE + 0.95 F244bb + 0.01 F245fa + 0.01 TFP + 0.01 F1225yeZ + 0.01 F1225zc TOTAL PRES bar | Organics 0.01 F1233zdE + 0.01 F244bb + 0.95 F245fa + 0.01 TFP + 0.01 F1225yeZ + 0.01 F1225zc TOTAL PRES bar | Organics 0.01 F1233zdE + 0.01 F244bb + 0.01 F245fa + 0.95 TFP + 0.01 F1225yeZ + 0.01 F1225zc TOTAL PRES bar | Organics 0.01 F1233zdE + 0.01 F244bb + 0.01 F245fa + 0.01 TFP + 0.95 F1225yeZ + 0.01 F1225zc TOTAL PRES bar | Organics 0.01F1233zdE + 0.01 F244bb + 0.01 F245fa + 0.01 TFP + 0.01 F1225yeZ + 0.95 F1225zc TOTAL PRES bar |
| 0 | 4.8 | 1.5 | 0.9 | 1.7 | 11.3 | 5.1 | 5.3 |
| 0.05 | 5.9 | 2.6 | 2.1 | 2.8 | 12.1 | 6.2 | 6.2 |
| 0.1 | 5.9 | 2.6 | 2.1 | 2.8 | 12.0 | 6.2 | 6.3 |
| 0.15 | 5.8 | 2.6 | 2.1 | 2.8 | 11.9 | 6.2 | 6.3 |
| 0.2 | 5.8 | 2.6 | 2.1 | 2.8 | 11.8 | 6.2 | 6.3 |
| 0.25 | 5.8 | 2.6 | 2.1 | 2.8 | 11.7 | 6.2 | 6.2 |
| 0.3 | 5.8 | 2.6 | 2.1 | 2.8 | 11.6 | 6.2 | 6.2 |
| 0.35 | 5.8 | 2.6 | 2.1 | 2.8 | 11.5 | 6.2 | 6.2 |
| 0.4 | 5.8 | 2.6 | 2.0 | 2.8 | 11.5 | 6.2 | 6.2 |
| 0.45 | 5.8 | 2.6 | 2.0 | 2.8 | 11.4 | 6.2 | 6.2 |
| 0.5 | 5.7 | 2.6 | 2.0 | 2.8 | 11.5 | 6.2 | 6.2 |
| 0.55 | 5.7 | 2.6 | 2.0 | 2.8 | 11.5 | 6.2 | 6.2 |
| 0.6 | 5.7 | 2.6 | 2.0 | 2.8 | 11.5 | 6.2 | 6.1 |
| 0.65 | 5.6 | 2.6 | 2.0 | 2.8 | 11.5 | 6.2 | 6.0 |
| 0.7 | 5.6 | 2.6 | 2.0 | 2.8 | 11.6 | 6.1 | 5.8 |
| 0.75 | 5.4 | 2.6 | 2.0 | 2.8 | 11.3 | 5.9 | 5.6 |
| 0.8 | 5.1 | 2.5 | 2.0 | 2.7 | 10.5 | 5.6 | 5.2 |
| 0.85 | 4.7 | 2.3 | 1.8 | 2.5 | 8.9 | 5.0 | 4.6 |
| 0.9 | 3.9 | 2.1 | 1.8 | 2.2 | 8.9 | 4.2 | 3.8 |
| 0.95 | 2.8 | 1.7 | 1.6 | 1.8 | 6.0 | 3.0 | 2.7 |
| 1 | 1.2 | 1.2 | 1.2 | 1.2 | 1.2 | 1.2 | 1.2 |

Example 17: Temperature and Pressure Range of Systems with 7 Compounds

| System with 7 compounds | Boiling point range | |
|---|---|---|
| | Temperature ° C. | Pressure bar abs |
| HC-HCFO-1233xf-HFC-245cb-HCFO-1233zdE-HFO-1234zeE-HFO-1234zeZ-HFO-1243zf | 0 to 40 | ~0.9 to ~10.3 |
| HF-HCFO-1233xf-HFO-1234yf-HFC-245cb-HCFO-1233zdE-HFO-1234zeE-HFO-1234zeZ | 0 to 40 | ~0.9 to ~11.5 |
| HF-HCFO-1233xf-HFO-1234yf-HFC-245cb-HCFO-1233zdE-HFO-1234zeE-HFO-1243zf | 0 to 40 | ~1.0 to ~11.6 |
| HF-HCFO-1233xf-HFO-1234yf-HFC-245cb-HCFO-1233zdE-HFO-1234zeZ-HFO-1243zf | 0 to 40 | ~0.9 to ~11.5 |
| HF-HCFO-1233xf-HFO-1234yf-HCFO-1233zdE-HFO-1234zeE-HFO-1234zeZ-HFO-1243zf | 0 to 40 | ~0.9 to ~11.5 |
| HF-HFO-1234yf-HFC-245b-HCFO-1233zdE-HFO-1234zeE-HFO-1234zeZ-HFO-1243zf | 0 to 40 | ~1.0 to ~11.6 |
| HF-HCFC-1233zdE-HCFC-244bb-HFC-245fa-Trifluoropropyne-HFO-1225yeZ-HFO-1225zc | 0 to 40 | ~0.7 to ~17.5 |

Example 18: Decantation Range of Systems with 7 Compounds

| System with 7 compounds | Decantation ranges Mass percentage of HF Temperature | | |
|---|---|---|---|
| | 0° C. | 25° C. | 40° C. |
| HC-HCFO-1233xf-HFC-245cb-HCFO-1233zdE-HFO-1234zeE-HFO-1234zeZ-HFO-1243zf | 5-75 | 5-70 | 10-55 |
| HF-HCFO-1233xf-HFO-1234yf-HFC-245cb-HCFO-1233zdE-HFO-1234zeE-HFO-1234zeZ | 5-75 | 5-70 | 10-60 |
| HF-HCFO-1233xf-HFO-1234yf-HFC-245cb-HCFO-1233zdE-HFO-1234zeE-HFO-1243zf | 5-75 | 10-65 | 20 |
| HF-HCFO-1233xf-HFO-1234yf-HFC-245cb-HCFO-1233zdE-HFO-1234zeZ-HFO-1243zf | 5-70 | 5-70 | 10-60 |
| HF-HCFO-1233xf-HFO-1234yf-HCFO-1233zdE-HFO-1234zeE-HFO-1234zeZ-HFO-1243zf | 5-75 | 10-65 | 15-45 |
| HF-HFO-1234yf-HFC-245b-HCFO-1233zdE-HFO-1234zeE-HFO-1234zeZ-HFO-1243zf | 5-75 | 10-65 | * |
| HF-HCFC-1233zdE-HCFC-244bb-HFC-245fa-Trifluoropropyne-HFO-1225yeZ-HFO-1225zc | 5-75 | 5-70 | 10-60 |

Example 19: Systems with 8 Compounds

HF-HCFO-1233xf-HFO-1234yf-HFC-245cb-HCFO-1233zdE-HFO-1234zeE-HFO-1234zeZ-HFO-1243zf

| Organics 0.01 F1233xf + 0.94 F245cb + 0.01 F1233zdE + 0.01 F1234zeE + 0.01 F1234zeZ + 0.01 F1243zf | | Organics 0.01 F1233xf + 0.01 F1234yf + 0.94 F245cb + 0.01 F1233zdE + 0.01 F1234zeE + 0.01 F1234zeZ + 0.01 F1243zf | | Organics 0.01 F1233xf + 0.01 F1234yf + 0.01 F245cb + 0.94 F1334zdE + 0.01 F1234zeE + 0.01 F1234zeZ + 0.01 F1243zf | | Organics 0.01 F1233xf + 0.01 F1234yf + 0.01 F245cb + 0.01 F1233zdE + 0.94 F1234zeE + 0.01 F1234zeZ + 0.01 F1243zf | | Organics 0.01 F1233xf + 0.01 F1234yf + 0.01 F245cb + 0.01 F1233zdE + F1234zeE + 0.94 F1234zeZ + 0.01 F1243zf | | Organics 0.01 F1233xf + 0.01 F1234yf + 0.01 F245cb + 0.01 F1233zdE + F1234zeE + 0.94 F1234zeZ + 0.01 F1243zf | | Organics 0.16 F1234yf + 0.14 F1233xf + 0.14 F245cb + 0.14 F1233zdE + 0.14 F1234zeE + 0.14 F1234zeZ + 0.14 F1243zf | |
|---|---|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 4.6 | 0 | 1.5 | 0 | 4.8 | 0 | 2.0 | 0 | 5.7 | 0 | 3.9 |
| 0.05 | 7.6 | 0.05 | 5.8 | 0.05 | 2.6 | 0.05 | 5.8 | 0.05 | 3.1 | 0.05 | 6.7 | 0.05 | 5.0 |
| 0.1 | 7.6 | 0.1 | 5.8 | 0.1 | 2.6 | 0.1 | 5.8 | 0.1 | 3.1 | 0.1 | 6.7 | 0.1 | 5.0 |
| 0.15 | 7.6 | 0.15 | 5.8 | 0.15 | 2.6 | 0.15 | 5.8 | 0.15 | 3.1 | 0.15 | 6.7 | 0.15 | 5.0 |
| 0.2 | 7.6 | 0.2 | 5.8 | 0.2 | 2.6 | 0.2 | 5.8 | 0.2 | 3.1 | 0.2 | 6.7 | 0.2 | 5.0 |
| 0.25 | 7.6 | 0.25 | 5.8 | 0.25 | 2.6 | 0.25 | 5.8 | 0.25 | 3.1 | 0.25 | 6.7 | 0.25 | 5.0 |
| 0.3 | 7.6 | 0.3 | 5.8 | 0.3 | 2.6 | 0.3 | 5.8 | 0.3 | 3.1 | 0.3 | 6.7 | 0.3 | 5.0 |
| 0.35 | 7.6 | 0.35 | 5.8 | 0.35 | 2.6 | 0.35 | 5.8 | 0.35 | 3.1 | 0.35 | 6.7 | 0.35 | 5.0 |
| 0.4 | 7.6 | 0.4 | 5.8 | 0.4 | 2.6 | 0.4 | 5.8 | 0.4 | 3.1 | 0.4 | 6.7 | 0.4 | 5.0 |
| 0.45 | 7.6 | 0.45 | 5.8 | 0.45 | 2.6 | 0.45 | 5.8 | 0.45 | 3.1 | 0.45 | 6.7 | 0.45 | 5.0 |
| 0.5 | 7.6 | 0.5 | 5.8 | 0.5 | 2.6 | 0.5 | 5.8 | 0.5 | 3.1 | 0.5 | 6.7 | 0.5 | 5.0 |
| 0.55 | 7.6 | 0.55 | 5.8 | 0.55 | 2.6 | 0.55 | 5.7 | 0.55 | 3.1 | 0.55 | 6.7 | 0.55 | 5.0 |
| 0.6 | 7.6 | 0.6 | 5.8 | 0.6 | 2.6 | 0.6 | 5.7 | 0.6 | 3.1 | 0.6 | 6.7 | 0.6 | 5.0 |
| 0.65 | 7.6 | 0.65 | 5.8 | 0.65 | 2.6 | 0.65 | 5.6 | 0.65 | 3.1 | 0.65 | 6.6 | 0.65 | 5.0 |
| 0.7 | 7.5 | 0.7 | 5.8 | 0.7 | 2.6 | 0.7 | 5.5 | 0.7 | 3.1 | 0.7 | 6.5 | 0.7 | 5.0 |
| 0.75 | 7.4 | 0.75 | 5.8 | 0.75 | 2.6 | 0.75 | 5.4 | 0.75 | 3.1 | 0.75 | 6.3 | 0.75 | 4.9 |
| 0.8 | 7.1 | 0.8 | 5.8 | 0.8 | 2.6 | 0.8 | 5.1 | 0.8 | 3.1 | 0.8 | 6.0 | 0.8 | 4.6 |
| 0.85 | 6.5 | 0.85 | 5.8 | 0.85 | 2.5 | 0.85 | 4.8 | 0.85 | 2.9 | 0.85 | 5.5 | 0.85 | 4.2 |
| 0.9 | 5.5 | 0.9 | 5.0 | 0.9 | 2.3 | 0.9 | 4.3 | 0.9 | 2.7 | 0.9 | 4.7 | 0.9 | 3.6 |
| 0.95 | 3.8 | 0.95 | 3.5 | 0.95 | 2.1 | 0.95 | 3.6 | 0.95 | 2.4 | 0.95 | 3.3 | 0.95 | 2.6 |
| 1 | 1.2 | 1 | 1.2 | 1 | 1.7 | 1 | 2.6 | 1 | 1.9 | 1 | 1.2 | 1 | 1.2 |

-continued

| MASSFRAC HF | Organics 0.94 F1233xf + 0.01 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.94 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.94 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.94 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.94 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.94 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.01 F1234zeZ + 0.94 F244bb TOTAL PRESSURE bar | Organics 0.16 F1233xf + 0.14 F1234yf + 0.14 F245cb + 0.14 F1233zdE + 0.14 F1234zeE + 0.14 F1234zeZ + 0.14 F244bb TOTAL PRESSURE bar |
|---|---|---|---|---|---|---|---|---|
| 0 | 1.7 | 6.6 | 4.5 | 1.5 | 4.8 | 1.9 | 0.8 | 3.2 |
| 0.05 | 2.8 | 7.5 | 5.7 | 2.6 | 5.7 | 3.0 | 2.0 | 4.3 |
| 0.1 | 2.8 | 7.5 | 5.7 | 2.6 | 5.7 | 3.0 | 2.0 | 4.3 |
| 0.15 | 2.8 | 7.5 | 5.7 | 2.6 | 5.7 | 3.0 | 2.0 | 4.3 |
| 0.2 | 2.8 | 7.5 | 5.7 | 2.6 | 5.7 | 3.0 | 2.0 | 4.3 |
| 0.25 | 2.8 | 7.5 | 5.7 | 2.6 | 5.7 | 3.0 | 2.0 | 4.3 |
| 0.3 | 2.8 | 7.5 | 5.7 | 2.6 | 5.7 | 3.0 | 2.0 | 4.3 |
| 0.35 | 2.8 | 7.5 | 5.7 | 2.6 | 5.7 | 3.0 | 2.0 | 4.3 |
| 0.4 | 2.8 | 7.5 | 5.7 | 2.6 | 5.7 | 3.0 | 2.0 | 4.3 |
| 0.45 | 2.8 | 7.5 | 5.7 | 2.6 | 5.7 | 3.0 | 2.0 | 4.3 |
| 0.5 | 2.8 | 7.5 | 5.7 | 2.6 | 5.7 | 3.0 | 2.0 | 4.3 |
| 0.55 | 2.8 | 7.5 | 5.7 | 2.6 | 5.7 | 3.0 | 2.0 | 4.2 |
| 0.6 | 2.8 | 7.5 | 5.7 | 2.6 | 5.6 | 3.0 | 2.0 | 4.2 |
| 0.65 | 2.8 | 7.5 | 5.7 | 2.6 | 5.6 | 3.0 | 2.0 | 4.2 |
| 0.7 | 2.8 | 7.5 | 5.7 | 2.6 | 5.5 | 3.0 | 2.0 | 4.2 |
| 0.75 | 2.8 | 7.4 | 5.7 | 2.6 | 5.3 | 3.0 | 2.0 | 4.2 |
| 0.8 | 2.6 | 7.0 | 5.7 | 2.4 | 5.1 | 2.9 | 1.9 | 4.0 |
| 0.85 | 2.4 | 6.5 | 5.7 | 2.3 | 4.7 | 2.7 | 1.9 | 3.7 |
| 0.9 | 2.2 | 5.4 | 4.9 | 2.0 | 4.3 | 2.4 | 1.8 | 3.2 |
| 0.95 | 1.8 | 3.8 | 3.5 | 1.7 | 3.6 | 1.9 | 1.6 | 2.4 |
| 1 | 1.2 | 1.2 | 1.2 | 1.2 | 2.6 | 1.2 | 1.2 | 1.2 |

Table header spanning: HF-HFO-1234yf-HFC-245cb-HCFO-1233xf-HFO-1234zeE-HFO-1234zeZ-HCFO-1233zdE-HCFC-244bb -continued HF-HFO-1234yf-HFC-245cb-HCFO-1233xf-HFO-1234zeE-HFO-1234zeZ-HCFO-1233zdE-Trifluoropropyne

| MASSFRAC HF | Organics 0.16 F1234yf + 0.14 F245cb + 0.14 F1233xf + 0.14 F1234zeE + 0.14 F1234zeZ + 0.14 F1233zdE + 0.14 TPF TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 TPF TOTAL PRESSURE bar |
|---|---|---|---|---|---|---|---|
| 0 | 5.0 | 6.7 | 4.7 | 1.8 | 4.9 | 2.0 | 1.6 |
| 0.05 | 6.0 | 7.6 | 5.8 | 2.9 | 5.8 | 3.1 | 2.7 |
| 0.1 | 6.0 | 7.6 | 5.8 | 2.9 | 5.9 | 3.1 | 2.7 |
| 0.15 | 6.0 | 7.6 | 5.8 | 2.9 | 5.9 | 3.1 | 2.7 |
| 0.2 | 6.0 | 7.6 | 5.8 | 2.9 | 5.9 | 3.1 | 2.7 |
| 0.25 | 6.0 | 7.6 | 5.8 | 2.9 | 5.8 | 3.1 | 2.7 |
| 0.3 | 6.0 | 7.6 | 5.8 | 2.9 | 5.8 | 3.1 | 2.7 |
| 0.35 | 6.0 | 7.6 | 5.8 | 2.9 | 5.8 | 3.1 | 2.7 |
| 0.4 | 6.0 | 7.6 | 5.8 | 2.9 | 5.8 | 3.1 | 2.7 |
| 0.45 | 6.0 | 7.6 | 5.8 | 2.9 | 5.8 | 3.1 | 2.7 |
| 0.5 | 6.0 | 7.6 | 5.8 | 2.9 | 5.8 | 3.1 | 2.7 |
| 0.55 | 6.0 | 7.6 | 5.8 | 2.9 | 5.8 | 3.1 | 2.7 |
| 0.6 | 6.0 | 7.6 | 5.8 | 2.9 | 5.7 | 3.1 | 2.7 |
| 0.65 | 6.0 | 7.6 | 5.8 | 2.9 | 5.6 | 3.1 | 2.7 |
| 0.7 | 6.0 | 7.6 | 5.8 | 2.9 | 5.4 | 3.1 | 2.7 |
| 0.75 | 5.9 | 7.5 | 5.8 | 2.9 | 5.2 | 3.1 | 2.7 |
| 0.8 | 5.6 | 7.1 | 5.8 | 2.8 | 4.9 | 3.0 | 2.6 |
| 0.85 | 5.1 | 6.6 | 5.8 | 2.6 | 4.4 | 2.8 | 2.4 |
| 0.9 | 4.3 | 5.5 | 5.0 | 2.2 | 3.6 | 2.4 | 2.1 |
| 0.95 | 3.1 | 3.8 | 3.5 | 1.8 | 2.6 | 1.9 | 1.7 |
| 1 | 1.2 | 1.2 | 1.2 | 1.2 | 1.2 | 1.2 | 1.2 |

-continued

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F245fa TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F245fa TOTAL PRESSURE bar | HF-HFO-1234yf-HFC-245cb-HCFO-1233xf-HFO-1234zeE-HFO-1234zeZ-HCFO-1233zdE-HFC-245fa Organics 0.01 F1234yf + 0.94 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F245fa TOTAL PRESSURE bar |
|---|---|---|---|---|---|---|---|
| 0 | 3.4 | 6.6 | 4.5 | 1.7 | 4.8 | 1.9 | 1.5 | 1.6 |
| 0.05 | 4.5 | 7.5 | 5.7 | 2.8 | 5.7 | 3.0 | 2.6 | 2.8 |
| 0.1 | 4.5 | 7.5 | 5.7 | 2.8 | 5.7 | 3.0 | 2.6 | 2.8 |
| 0.15 | 4.5 | 7.5 | 5.7 | 2.8 | 5.7 | 3.0 | 2.6 | 2.8 |
| 0.2 | 4.5 | 7.5 | 5.7 | 2.8 | 5.7 | 3.0 | 2.6 | 2.8 |
| 0.25 | 4.5 | 7.5 | 5.7 | 2.8 | 5.7 | 3.0 | 2.6 | 2.8 |
| 0.3 | 4.5 | 7.5 | 5.7 | 2.8 | 5.7 | 3.0 | 2.6 | 2.8 |
| 0.35 | 4.5 | 7.5 | 5.7 | 2.8 | 5.7 | 3.0 | 2.6 | 2.8 |
| 0.4 | 4.5 | 7.5 | 5.7 | 2.8 | 5.7 | 3.0 | 2.6 | 2.8 |
| 0.45 | 4.5 | 7.5 | 5.7 | 2.8 | 5.7 | 3.0 | 2.6 | 2.8 |
| 0.5 | 4.5 | 7.5 | 5.7 | 2.8 | 5.7 | 3.0 | 2.6 | 2.8 |
| 0.55 | 4.5 | 7.5 | 5.7 | 2.8 | 5.7 | 3.0 | 2.6 | 2.8 |
| 0.6 | 4.5 | 7.5 | 5.7 | 2.8 | 5.6 | 3.0 | 2.6 | 2.8 |
| 0.65 | 4.5 | 7.5 | 5.7 | 2.8 | 5.5 | 3.0 | 2.6 | 2.8 |
| 0.7 | 4.5 | 7.5 | 5.7 | 2.8 | 5.3 | 3.0 | 2.6 | 2.8 |
| 0.75 | 4.4 | 7.4 | 5.7 | 2.8 | 5.1 | 3.0 | 2.6 | 2.8 |
| 0.8 | 4.2 | 7.1 | 5.8 | 2.6 | 4.7 | 2.9 | 2.5 | 2.7 |
| 0.85 | 3.9 | 6.5 | 5.7 | 2.5 | 4.3 | 2.7 | 2.3 | 2.5 |
| 0.9 | 3.3 | 5.4 | 4.9 | 2.2 | 3.6 | 2.4 | 2.0 | 2.2 |
| 0.95 | 2.4 | 3.8 | 3.5 | 1.8 | 2.6 | 1.9 | 1.7 | 1.8 |
| 1 | 1.2 | 1.2 | 1.2 | 1.2 | 1.2 | 1.2 | 1.2 | 1.2 |

-continued

HF-HFO-1234yf-HFC-245cb-HCFO-1233xf-HFO-1234zeE-HFO-1234zeZ-HCFO-1233zdE-HFO-1225yeZ

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225yeZ TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225yeZ TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225yeZ TOTAL PRESSURE bar |
|---|---|---|---|---|---|---|---|---|
| 0 | 3.8 | 6.6 | 4.6 | 1.7 | 4.8 | 1.9 | 1.5 | 5.1 |
| 0.05 | 4.9 | 7.6 | 5.8 | 2.8 | 5.8 | 3.0 | 2.6 | 6.1 |
| 0.1 | 4.9 | 7.6 | 5.8 | 2.8 | 5.8 | 3.0 | 2.6 | 6.1 |
| 0.15 | 4.9 | 7.6 | 5.8 | 2.8 | 5.8 | 3.0 | 2.6 | 6.1 |
| 0.2 | 4.9 | 7.5 | 5.8 | 2.8 | 5.8 | 3.0 | 2.6 | 6.1 |
| 0.25 | 4.9 | 7.6 | 5.8 | 2.8 | 5.8 | 3.0 | 2.6 | 6.1 |
| 0.3 | 4.9 | 7.6 | 5.8 | 2.8 | 5.8 | 3.0 | 2.6 | 6.1 |
| 0.35 | 4.9 | 7.6 | 5.8 | 2.8 | 5.8 | 3.0 | 2.6 | 6.1 |
| 0.4 | 4.9 | 7.6 | 5.8 | 2.8 | 5.8 | 3.0 | 2.6 | 6.1 |
| 0.45 | 4.9 | 7.6 | 5.8 | 2.8 | 5.7 | 3.0 | 2.6 | 6.1 |
| 0.5 | 4.9 | 7.6 | 5.8 | 2.8 | 5.7 | 3.0 | 2.6 | 6.1 |
| 0.55 | 4.9 | 7.6 | 5.8 | 2.8 | 5.6 | 3.0 | 2.6 | 6.1 |
| 0.6 | 4.9 | 7.6 | 5.8 | 2.8 | 5.5 | 3.0 | 2.6 | 6.1 |
| 0.65 | 4.9 | 7.5 | 5.8 | 2.8 | 5.3 | 3.0 | 2.6 | 6.0 |
| 0.7 | 5.0 | 7.4 | 5.8 | 2.8 | 5.1 | 3.0 | 2.6 | 5.8 |
| 0.75 | 4.8 | 7.1 | 5.8 | 2.7 | 4.8 | 2.9 | 2.5 | 5.5 |
| 0.8 | 4.6 | 6.5 | 5.8 | 2.5 | 4.3 | 2.7 | 2.3 | 5.0 |
| 0.85 | 4.2 | 5.5 | 4.9 | 2.2 | 3.6 | 2.4 | 2.1 | 4.2 |
| 0.9 | 3.6 | 3.8 | 3.5 | 1.8 | 2.6 | 1.9 | 1.7 | 2.9 |
| 0.95 | 2.6 | | | | | | | |
| 1 | 1.2 | 1.2 | 1.2 | 1.2 | 1.2 | 1.2 | 1.2 | 1.2 |

-continued

| | HF-HFO-1234yf-HFC-245cb-HCFO-1233xf-HFO-1234zeE-HFO-1234zeZ-HCFC-1233zdE-HFO-1225zc | | | | | | |
|---|---|---|---|---|---|---|---|
| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225zc TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225zc TOTAL PRESSURE bar | Organics 0.01 F1234yf + 0.01 F245cb + 0.01 F1233xf + 0.94 F1234zeE + 0.01 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225zc TOTAL PRESSURE bar |
| 0 | 3.9 | 6.6 | 4.6 | 1.7 | 4.8 | 1.9 | 1.5 | 5.2 |
| 0.05 | 4.9 | 7.6 | 5.8 | 2.8 | 5.8 | 3.0 | 2.6 | 6.2 |
| 0.1 | 4.9 | 7.6 | 5.8 | 2.8 | 5.8 | 3.0 | 2.6 | 6.2 |
| 0.15 | 4.9 | 7.6 | 5.8 | 2.8 | 5.8 | 3.0 | 2.6 | 6.2 |
| 0.2 | 4.9 | 7.6 | 5.8 | 2.8 | 5.8 | 3.0 | 2.6 | 6.2 |
| 0.25 | 4.9 | 7.6 | 5.8 | 2.8 | 5.8 | 3.0 | 2.6 | 6.2 |
| 0.3 | 4.9 | 7.6 | 5.8 | 2.8 | 5.8 | 3.0 | 2.6 | 6.2 |
| 0.35 | 4.9 | 7.6 | 5.8 | 2.8 | 5.8 | 3.0 | 2.6 | 6.2 |
| 0.4 | 4.9 | 7.6 | 5.8 | 2.8 | 5.8 | 3.0 | 2.6 | 6.2 |
| 0.45 | 4.9 | 7.6 | 5.8 | 2.8 | 5.8 | 3.0 | 2.6 | 6.2 |
| 0.5 | 4.9 | 7.6 | 5.8 | 2.8 | 5.7 | 3.0 | 2.6 | 6.1 |
| 0.55 | 4.9 | 7.6 | 5.8 | 2.8 | 5.7 | 3.0 | 2.6 | 6.1 |
| 0.6 | 4.9 | 7.6 | 5.8 | 2.8 | 5.6 | 3.0 | 2.6 | 6.0 |
| 0.65 | 4.9 | 7.6 | 5.8 | 2.8 | 5.5 | 3.0 | 2.6 | 5.9 |
| 0.7 | 4.9 | 7.5 | 5.8 | 2.8 | 5.3 | 3.0 | 2.6 | 5.8 |
| 0.75 | 4.8 | 7.4 | 5.8 | 2.8 | 5.1 | 3.0 | 2.6 | 5.5 |
| 0.8 | 4.6 | 7.1 | 5.8 | 2.7 | 4.8 | 2.9 | 2.5 | 5.1 |
| 0.85 | 4.2 | 6.5 | 5.8 | 2.5 | 4.3 | 2.7 | 2.3 | 4.6 |
| 0.9 | 3.5 | 5.5 | 4.9 | 2.2 | 3.6 | 2.4 | 2.1 | 3.8 |
| 0.95 | 2.6 | 3.8 | 3.5 | 1.8 | 2.6 | 1.9 | 1.7 | 2.7 |
| 1 | 1.2 | 1.2 | 1.2 | 1.2 | 1.2 | 1.2 | 1.2 | 1.2 |

Example 20: Temperature and Pressure Range of System with 8 Compounds

| System with 8 compounds | Boiling point range | |
|---|---|---|
| | Temperature ° C. | Pressure bar abs |
| HF-HCFO-1233xf-HFO-1234yf-HFC-245cb-HCFO-1233zdE-HFO-1234zeE-HFO-1234zeZ-HFO-1243zf | 0 to 40 | ~1.0~11.5 |
| HF-HFO-1234yf-HFC-245cb-HCFO-1233xf-HFO-1234zeE-HFO-1234zeZ-HCFO-1233zdE-HCFC-244bb | 0 to 40 | ~0.7 to ~11.5 |
| HF-HFO-1234yf-HFC-245cb-HCFO-1233xf-HFO-1234zeE-HFO-1234zeZ-HCFO-1233zdE-Trifluoropropyne | 0 to 40 | ~1.0 to ~17.4 |
| HF-HFO-1234yf-HFC-245cb-HCFO-1233xf-HFO-1234zeE-HFO-1234zeZ-HCFO-1233zdE-HFC-245fa | 0 to 40 | ~0.9 to ~11.5 |
| HF-HFO-1234yf-HFC-245cb-HCFO-1233xf-HFO-1234zeE-HFO-1234zeZ-HCFO-1233zdE-HFO-1225yeZ | 0 to 40 | ~1.0 to ~11.5 |
| HF-HFO-1234yf-HFC-245cb-HCFO-1233xf-HFO-1234zeE-HFO-1234zeZ-HCFC-1233zdE-HFO-1225zc | 0 to 40 | ~1.0 to ~11.5 |

Example 21: Decantation Ranges of System with 8 Compounds

| System with 8 compounds | Decantation ranges Mass percentage of HF Temperature | | |
|---|---|---|---|
| | 0° C. | 25° C. | 40° C. |
| HF-HCFO-1233xf-HFO-1234yf-HFC-245cb-HCFO-1233zdE-HFO-1234zeE-HFO-1234zeZ-HFO-1243zf | 5-75% | 5-70% | 15-50% |
| HF-HFO-1234yf-HFC-245cb-HCFO-1233xf-HFO-1234zeE-HFO-1234zeZ-HCFO-1233zdE-HCFC-244bb | 5-80 | 5-75 | 5-70 |
| HF-HFO-1234yf-HFC-245cb-HCFO-1233xf-HFO-1234zeE-HFO-1234zeZ-HCFO-1233zdE-Trifluoropropyne | 5-75 | 10-65 | * |
| HF-HFO-1234yf-HFC-245cb-HCFO-1233xf-HFO-1234zeE-HFO-1234zeZ-HCFO-1233zdE-HFC-245fa | 5-75 | 5-70 | 10-60 |
| HF-HFO-1234yf-HFC-245cb-HCFO-1233xf-HFO-1234zeE-HFO-1234zeZ-HCFO-1233zdE-HFO-1225yeZ | 5-75 | 5-70 | 15-55 |
| HF-HFO-1234yf-HFC-245cb-HCFO-1233xf-HFO-1234zeE-HFO-1234zeZ-HCFC-1233zdE-HFO-1225zc | 5-75 | 5-65 | 15-50 |

Example 22: Systems with 13 Compounds

| | HF-HFO-1234yf-HFC-245cb-HCFO-1233xf-HCFO-1233zdE-HFO-1234zeE- HFO-1234zeZ-HFC-1243zf-HCFC-244bb-TFP-HFC-245fa-HFO-1225yeZ-HFO-1225zc | | | | |
|---|---|---|---|---|---|
| MASSFRAC HF | Organics 0.087 F1234yf + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.01 F1233zdE + 0.89 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
| 0 | 4.5 | 6.5 | 1.9 | 4.8 | 1.7 |
| 0.05 | 5.6 | 7.5 | 3.0 | 5.8 | 2.9 |
| 0.1 | 5.6 | 7.5 | 3.0 | 5.8 | 2.8 |
| 0.15 | 5.6 | 7.5 | 3.0 | 5.8 | 2.8 |
| 0.2 | 5.6 | 7.5 | 3.0 | 5.8 | 2.8 |

-continued

HF-HFO-1234yf-HFC-245cb-HCFO-1233xf-HCFO-1233zdE-HFO-1234zeE- HFO-1234zeZ-HFC-1243zf-HCFC-244bb-TFP-HFC-245fa-HFO-1225yeZ-HFO-1225zc

| MASSFRAC HF | Organics 0.087 F1234yf + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.01 F1233zdE + 0.89 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
|---|---|---|---|---|---|
| 0.25 | 5.6 | 7.5 | 3.0 | 5.8 | 2.8 |
| 0.3 | 5.6 | 7.5 | 3.0 | 5.0 | 2.8 |
| 0.35 | 5.6 | 7.5 | 3.0 | 5.8 | 2.8 |
| 0.4 | 5.6 | 7.5 | 3.0 | 5.8 | 2.8 |
| 0.45 | 5.5 | 7.5 | 3.0 | 5.8 | 2.8 |
| 0.5 | 5.5 | 7.5 | 3.0 | 5.8 | 2.8 |
| 0.55 | 5.5 | 7.5 | 3.0 | 5.7 | 2.8 |
| 0.6 | 5.5 | 7.5 | 3.0 | 5.6 | 2.8 |
| 0.65 | 5.5 | 7.5 | 3.0 | 5.5 | 2.8 |
| 0.7 | 5.4 | 7.5 | 3.0 | 5.4 | 2.8 |
| 0.75 | 5.3 | 7.3 | 3.0 | 5.2 | 2.8 |
| 0.8 | 5.1 | 7.0 | 2.8 | 4.8 | 2.7 |
| 0.85 | 4.6 | 6.4 | 2.6 | 4.3 | 2.5 |
| 0.9 | 3.9 | 5.4 | 2.3 | 3.6 | 2.2 |
| 0.95 | 2.8 | 3.7 | 1.8 | 2.6 | 1.6 |
| 1 | 1.2 | 1.2 | 1.2 | 1.2 | 1.2 |

Example 23: Temperature and Pressure Range of System with 13 Compounds

| | Boiling point range | |
|---|---|---|
| System with 13 compounds | Temperature ° C. | Pressure bar abs |
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeA-HFO-1225zc | 0 to 40 | ~0.7 ~18.0 |

Example 24: Decantation Ranges of System with 13 Compounds

| | Decantation ranges Mass percentage of HF Temperature | | |
|---|---|---|---|
| System with 13 compounds | 0° C. | 25° C. | 40° C. |
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 5-75% | 10-70% | 15-60% |

The invention claimed is:

1. An azeotropic or quasi-azeotropic composition consisting essentially of hydrogen fluoride and E-3,3,3-trifluoro-1-chloropropene, wherein the composition has from 5% to 70% by weight of hydrogen fluoride and from 95% to 30% by weight of E-3,3,3-trifluoro-1-chloropropene.

2. The composition as claimed in claim 1, wherein the composition is azeotropic.

3. The composition as claimed in claim 1, wherein the composition is quasi-azeotropic, wherein the pressure difference between the pressure at the dew point and the pressure at the bubble formation point is less than or equal to 5%, on the basis of the pressure at the bubble formation point.

4. The composition as claimed in claim 1, wherein the boiling point of this composition is between 0 and 40° C. at a pressure of between 0.9 and 4 bar absolute.

5. The composition as claimed in claim 1, wherein the composition has from 10% to 65% by weight of hydrogen fluoride and from 90% to 35% by weight of E-3,3,3-trifluoro-1-chloropropene, the boiling point of this composition is between 0 and 40° C. at a pressure of between 0.9 and 4 bar absolute.

6. The composition as claimed in claim 1, wherein the composition consists of hydrogen fluoride and E-3,3,3-trifluoro-1-chloropropene.

7. The composition as claimed in claim 6, wherein the composition is azeotropic.

8. The composition as claimed in claim 6, wherein the composition is quasi-azeotropic, wherein the pressure difference between the pressure at the dew point and the pressure at the bubble formation point is less than or equal to 5%, on the basis of the pressure at the bubble formation point.

9. The composition as claimed in claim 6, wherein the boiling point of this composition is between 0 and 40° C. at a pressure of between 0.9 and 4 bar absolute.

10. The composition as claimed in claim 6, wherein the composition has from 10% to 65% by weight of hydrogen fluoride and from 90% to 35% by weight of E-3,3,3-trifluoro-1-chloropropene, the boiling point of this composition is between 0 and 40° C. at a pressure of between 0.9 and 4 bar absolute.

* * * * *